(12) United States Patent
Sumi

(10) Patent No.: US 7,775,980 B2
(45) Date of Patent: Aug. 17, 2010

(54) DISPLACEMENT MEASUREMENT METHOD AND APPARATUS, STRAIN MEASUREMENT METHOD AND APPARATUS, ELASTICITY AND VISCO-ELASTICITY CONSTANTS MEASUREMENT APPARATUS, AND THE ELASTICITY AND VISCO-ELASTICITY CONSTANTS MEASUREMENT APPARATUS-BASED TREATMENT APPARATUS

(76) Inventor: Chikayoshi Sumi, Yourcourt Tokorozawa Kusunoki-dai 303, 3-18-6, Kusunoki-dai, Tokorozawa-shi, Saitama 359-0037 (JP)

( * ) Notice: Subject to any disclaimer, the term of this patent is extended or adjusted under 35 U.S.C. 154(b) by 1155 days.

(21) Appl. No.: 11/312,591

(22) Filed: Dec. 21, 2005

(65) Prior Publication Data
US 2006/0184020 A1 Aug. 17, 2006

(51) Int. Cl.
*A61B 8/00* (2006.01)
(52) U.S. Cl. .................. 600/442; 600/449; 600/437
(58) Field of Classification Search .......... 600/437–472
See application file for complete search history.

(56) References Cited

U.S. PATENT DOCUMENTS 5,460,178 A 10/1995 Hudon et al.
6,508,768 B1 * 1/2003 Hall et al. .................. 600/443

FOREIGN PATENT DOCUMENTS

JP 7-55775 A 3/1995
WO WO 99/17660 A1 4/1999

OTHER PUBLICATIONS

Sumi, Chikayoshi, Effectiveness of ultrasonic strain measurement-based tissue shear modulus imaging—Toward realization of clinical system for combined diagnosis and treatment; Technical Report of IEICE; MBE2001-31 (Jun. 2001); (Partial translation of p. 92, left column, second paragraph).

(Continued)

*Primary Examiner*—Brian Casler
*Assistant Examiner*—John F Ramirez
(74) *Attorney, Agent, or Firm*—Sughrue Mion, PLLC

(57) ABSTRACT

The present invention provides elastic constant and visco elastic constant measurement apparatus etc. for measuring in the ROI in living tissues elastic constants such as shear modulus, Poisson's ratio, Lame constants, etc., visco elastic constants such as visco shear modulus, visco Poisson's ratio, visco Lame constants, etc. and density even if there exist another mechanical sources and uncontrollable mechanical sources in the object. The elastic constant and visco elastic constant measurement apparatus is equipped with means of data storing 2 (storage of deformation data measured in the ROI 7 etc.) and means of calculating elastic and visco elastic constants 1 (calculator of shear modulus etc. at arbitrary point in the ROI from measured strain tensor data etc.), the means of calculating elastic and visco elastic constants numerically determines elastic constants etc. from the first order partial differential equations relating elastic constants etc. and strain tensor etc.

10 Claims, 26 Drawing Sheets

OTHER PUBLICATIONS

Chikayoshi Sume, et al., Phantom Experiment on Estimation of Shear Modulus Distribution in Soft Tissue From Ultrasonic Measurment of Displacement Vector Field., IEICE Trans. Fundamentals, vol. E78-A, No. 12, Dec. 12, 1995, pp. 1655-1664.

Chikayoshi Sume, memeber, IEEE, Fine Elasticity Imaging Utilizing the Iterative RF-Echo Phase Matching Method, IEEE, Transactions on Ultrasonics, and Frequency Control, vol. 46 No. 1, Jan. 1999, pp. 158-166.

Hahn, Stefan L., Multidimensional Complex Signals with Single-Orthant Spectra, Proceeding of the IEEE, vol. 80, No. 8, Aug. 1992.

* cited by examiner

FIG.2
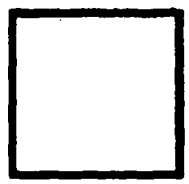
ULTRASOUND
OSCILLATOR
1D ARRAYED ULTRASOUND OSCILLATORS
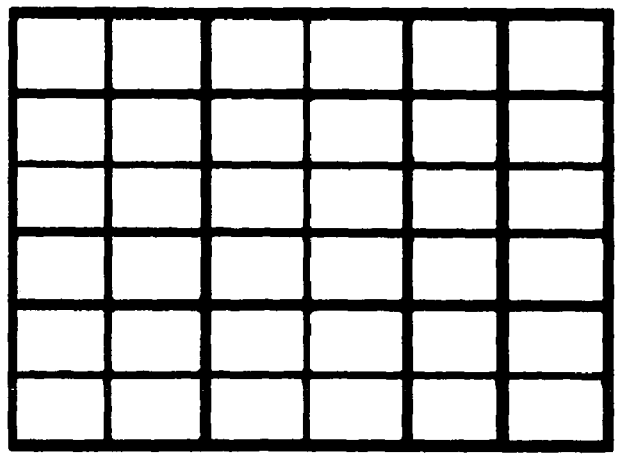
2D ARRAYED ULTRASOUND OSCILLATORS

FIG.10

METHOD 1-1 (METHOD 2-1, METHOD 3-1) : START OF MEASUREMENT
OF DISPLACEMENT VECTOR DISTRIBUTION d(x,y,z) IN SOI, ROI

↓

PROCESS 0: START OF ESTIMATION OF DISPLACEMENT VECTOR
d(x,y,z) AT POINT (x,y,z)
i =1

↓

PROCESS 1: PHASE MATCHING USING i-1TH ESTIMATE di-1
(d0: INITIAL VALUE)

↓

PROCESS 2: ESTIMATE OF RESIDUAL DISPLACEMENT VECTOR UI
FROM PHASE OF CROSS-SPECTRUM UTILIZING
LEAST-SQUARES METHOD
TO COPE WITH LARGE DISPLACEMENT:
  (i)   UNWRAP OF PHASE
  (ii)  UTILIZATION OF CROSS-CORRELATION METHOD
  (iii) THIN OUT ULTRASOUND DATA

↓

PROCESS 3: UPDATE OF ESTIMATE OF DISPLACEMENT VECTOR:
di = di-1 + ui

↓

PROCESS 4: MAKE SPATIAL RESOLUTION HIGH ?
    YES: MAKE LOCAL REGION SIZE SMALL
    NO:  LEAVE LOCAL REGION SIZE

↓

PROCESS 5: TERMINATE OF ITERATIVE ESTIMATION ?
    YES: MOVE TO ANOTHER POINT (x.y.z)  => PROCESS 6
    NO:  i = i + 1                      => PROCESS 1

↓

PROCESS 6: FINISH ESTIMATING AT ALL POINTS IN SOI, ROI ?
    YES => END
    NO  => PROCESS 0

METHOD 1-2 (METHOD 2-2, METHOD 3-2) : START OF MEASUREMENT
OF DISPLACEMENT VECTOR DISTRIBUTION d(x,y,z) IN SOI, ROI
(i = 1)

---

PROCESS 1: AT EACH POINT (x,y,z) IN SOI, ROI
- PROCESS 1 OF METHOD 1-1 (2-1, 3-1):
    PHASE MATCHING USING (SMOOTHED) i-1TH ESTIMATE $d_{i-1}$
    ($d_0$: INITIAL VALUE)
- PROCESS 2 OF METHOD 1-1 (2-1, 3-1):
    ESTIMATE OF RESIDUAL DISPLACEMENT VECTOR $u_i$

---

PROCESS 2: UPDATE OF ESTIMATE
          OF DISPLACEMENT VECTOR DISTRIBUTION:
- $d_i(x,y,z)$ = (SMOOTHED) $d_{i-1}(x,y,z)$ + $u_i(x,y,z)$
- SMOOTHING OF $d_i(x,y,z)$
    [LOW PASS FILTERING, MEDIAN FILTERING]

---

PROCESS 3: MAKE SPATIAL RESOLUTION HIGH ?
        YES: MAKE LOCAL REGION SIZE SMALL
        NO:  LEAVE LOCAL REGION SIZE

---

PROCESS 4: TERMINATE OF ITERATIVE ESTIMATION ?
        YES:              => END
        NO:  i = i + 1    => PROCESS 1

METHOD 1-3 (METHOD 2-3, METHOD 3-3) : START OF MEASUREMENT
OF DISPLACEMENT VECTOR DISTRIBUTION d(x,y,z) IN SOI, ROI
(i = 1)

---

PROCESS 1: AT EACH POINT (x,y,z) IN SOI, ROI
- PROCESS 1 OF METHOD 1-1 (2-1, 3-1):
    PHASE MATCHING USING (SMOOTHED) I-1TH ESTIMATE DI-1
    (D0: INITIAL VALUE)
- PROCESS 2 OF METHOD 1-1 (2-1, 3-1):
    ESTIMATE OF RESIDUAL DISPLACEMENT VECTOR UI
- POSSIBILITY OF DIVERGENCE OF PHASE MATCHING
  IN SOI, ROI?
            YES  =>  PROCESS 2
            NO:  =>  METHOD 1-1 (2-1, 3-1)

---

PROCESS 2: UPDATE OF ESTIMATE
            OF DISPLACEMENT VECTOR DISTRIBUTION:
- di(x,y,z) = (SMOOTHED) di-1(x,y,z) + ui(x,y,z)
- SMOOTHING OF di(x,y,z)
        [LOW PASS FILTERING, MEDIAN FILTERING]
    OVER SOI, ROI,
  OR OVER SPACE, REGION CENTERED ON THE SPACE, REGION
    WHERE THE POSSIBILITY IS DETECTED

---

PROCESS 3: MAKE SPATIAL RESOLUTION HIGH ?
        YES: MAKE LOCAL REGION SIZE SMALL
        NO:  LEAVE LOCAL REGION SIZE

---

PROCESS 4: TERMINATE OF ITERATIVE ESTIMATION ?
        YES:              => END
        NO:  i = i + 1    => PROCESS 1

METHOD 1-4 (METHOD 2-4, METHOD 3-4): START OF MEASUREMENT
OF DISPLACEMENT VECTOR DISTRIBUTION d(x,y,z) IN SOI, ROI
(i = 1)

---

↓

PROCESS 1: AT EACH POINT (x,y,z) IN SOI, ROI
- PROCESS 1 OF METHOD 1-1 (2-1, 3-1):
    PHASE MATCHING USING (SMOOTHED) i-1TH ESTIMATE $d_{i-1}$
    ($d_0$: INITIAL VALUE)
- ESTIMATE OF RESIDUAL DISPLACEMENT VECTOR
  DISTRIBUTION $u_i(x,y,z)$ UTILIZING LEAST-SQUARES
  METHOD, REGULARIZATION METHOD
    TO COPE WITH LARGE DISPLACEMENT:
        (i)   UNWRAP OF PHASE
        (ii)  UTILIZATION OF CROSS-CORRELATION METHOD
        (iii) THIN OUT ULTRASOUND DATA

↓

PROCESS 2: UPDATE OF ESTIMATE
            OF DISPLACEMENT VECTOR DISTRIBUTION:
- $d_i(x,y,z)$ = (SMOOTHED) $d_{i-1}(x,y,z)$ + $u_i(x,y,z)$
- OCCASIONALLY, SMOOTHING OF $d_i(x,y,z)$
        [LOW PASS FILTERING, MEDIAN FILTERING]

↓

PROCESS 3: MAKE SPATIAL RESOLUTION HIGH ?
        YES: MAKE LOCAL REGION SIZE SMALL
        NO:  LEAVE LOCAL REGION SIZE

↓

PROCESS 4: TERMINATE OF ITERATIVE ESTIMATION ?
        YES:              => END
        NO:  i = i + 1    => PROCESS 1

METHOD 1-5 (METHOD 2-5, METHOD 3-5): START OF MEASUREMENT OF DISPLACEMENT VECTOR DISTRIBUTION d(x,y,z) IN SOI, ROI (i = 1)

---

PROCESS 1: AT EACH POINT (x,y,z) IN SOI, ROI
- PROCESS 1 OF METHOD 1-1 (2-1, 3-1):
    PHASE MATCHING USING (SMOOTHED) i-1TH ESTIMATE $d_{i-1}$ ($d_0$: INITIAL VALUE)
- ESTIMATE OF RESIDUAL DISPLACEMENT VECTOR DISTRIBUTION $u_i(x,y,z)$ UTILIZING LEAST-SQUARES METHOD, REGULARIZATION METHOD
- POSSIBILITY OF DIVERGENCE OF PHASE MATCHING IN SOI, ROI?
    YES ⇒ PROCESS 2
    NO: ⇒ METHOD 1-1 (2-1, 3-1)

---

PROCESS 2: UPDATE OF ESTIMATE
        OF DISPLACEMENT VECTOR DISTRIBUTION:
- $d_i(x,y,z)$ = (SMOOTHED) $d_{i-1}(x,y,z) + u_i(x,y,z)$
- OCCASIONALLY, SMOOTHING OF $d_i(x,y,z)$
    [LOW PASS FILTERING, MEDIAN FILTERING]

---

PROCESS 3: MAKE SPATIAL RESOLUTION HIGH ?
    YES: MAKE LOCAL REGION SIZE SMALL
    NO: LEAVE LOCAL REGION SIZE

---

PROCESS 4: TERMINATE OF ITERATIVE ESTIMATION ?
    YES:            ⇒ END
    NO: i = i + 1   ⇒ PROCESS 1

FIG.21

```
START OF MEASUREMENT OF DISPLACEMENT VECTOR DISTRIBUTION
IN SOI, ROI
TARGET OF METHOD 4-1, METHOD 5-1: SPACE OF INTEREST (SOI)
TARGET OF METHOD 6-1: REGION OF INTEREST (ROI)
```

↓

```
PROCESS 1: AT EACH ROI OR LINE OF INTEREST
    2D DISPLACEMENT VECTOR MEASUREMENT IN 2D ROI
            (METHOD 2-1 OR 2-2 OR 2-3 OR 2-4 OR 2-5)
  OR
    ONE DIRECTION DISPLACEMENT COMPONENT DISTRIBUTION IN
    1D ROI (METHOD 3-1 OR 3-2 OR 3-3 OR 3-4 OR 3-5)
```

↓

```
MEASUREMENT OVER SOI, ROI
```

START OF MEASUREMENT OF DISPLACEMENT VECTOR DISTRIBUTION
$d(x,y,z)$ IN SOI, ROI ($i = 1$)
METHOD 4-2 BASED ON METHOD 2-2 (2D DISPLACEMENT VECTOR
    MEASUREMENT IN 2D ROI)
METHOD 5-2 BASED ON METHOD 3-2 (ONE DIRECTION
    DISPLACEMENT COMPONENT DISTRIBUTION IN 1D ROI)
METHOD 6-2 BASED ON METHOD 3-2

---

PROCESS 1:
TARGET OF METHOD 4-2, METHOD 5-2: SPACE OF INTEREST (SOI)
TARGET OF METHOD 6-2: REGION OF INTEREST (ROI)

AT EACH POINT $(x,y,z)$ IN SOI, ROI
    PROCESS 1 OF METHOD 2-1, 3-1:
        PHASE MATCHING USING (SMOOTHED) $i$-1TH ESTIMATE
        $d_{i-1}(x,y,z)$ ($d_0(x,y,z)$: INITIAL VALUE)
    ESTIMATE OF RESIDUAL DISPLACEMENT VECTOR $u_i(x,y,z)$
THUS, RESIDUAL DISPLACEMENT VECTOR DISTRIBUTION
$u_i(x,y,z)$ IS OBTAINED IN SOI, ROI.

---

PROCESS 2: UPDATE OF ESTIMATE
          OF DISPLACEMENT VECTOR DISTRIBUTION:
- $d_i(x,y,z)$ = (SMOOTHED) $d_{i-1}(x,y,z)$ + $u_i(x,y,z)$
- SMOOTHING OF $d_i(x,y,z)$
    [LOW PASS FILTERING, MEDIAN FILTERING]

---

PROCESS 3: MAKE SPATIAL RESOLUTION HIGH ?
        YES: MAKE LOCAL REGION SIZE SMALL
        NO: LEAVE LOCAL REGION SIZE

---

PROCESS 4: TERMINATE OF ITERATIVE ESTIMATION ?
    YES:          => END
    NO: $i = i + 1$  => PROCESS 1

STARY OF MEASUREMENT OF DISPLACEMENT VECTOR DISTRIBUTION
$d(x,y,z)$ IN SOI, ROI ($i = 1$)
METHOD 4-3 BASED ON METHOD 2-3 (2D DISPLACEMENT VECTOR
    MEASUREMENT IN 2D ROI)
METHOD 5-3 BASED ON METHOD 3-3 (ONE DIRECTION
    DISPLACEMENT COMPONENT DISTRIBUTION IN 1D ROI)
METHOD 6-3 BASED ON METHOD 3-3

---

PROCESS 1:
   TARGET OF METHOD 4-3, METHOD 5-3: SPACE OF INTEREST (SOI)
   TARGET OF METHOD 6-3: REGION OF INTEREST (ROI)

· AT EACH POINT $(x,y,z)$ IN SOI, ROI

PROCESS 1 OF METHOD 2-1, 3-1:
     PHASE MATCHING USING (SMOOTHED) $i-1$TH ESTIMATE
     $d_{i-1}(x,y,z)$ ($d_0(x,y,z)$: INITIAL VALUE)
   ESTIMATE OF RESIDUAL DISPLACEMENT VECTOR $u_i(x,y,z)$
   THUS, RESIDUAL DISPLACEMENT VECTOR DISTRIBUTION
   $u_i(x,y,z)$ IS OBTAINED IN SOI, ROI.

·POSSIBILITY OF DIVERGENCE OF PHASE MATCHING
   IN SOI, ROI?
        YES => PROCESS 2
        NO:  => METHOD 4-1 (5-1, 6-1)

---

PROCESS 2: UPDATE OF ESTIMATE
          OF DISPLACEMENT VECTOR DISTRIBUTION:

· $d_i(x,y,z)$ = (SMOOTHED) $d_{i-1}(x,y,z) + u_i(x,y,z)$

· SMOOTHING OF $d_i(x,y,z)$
     [LOW PASS FILTERING, MEDIAN FILTERING]

---

PROCESS 3: MAKE SPATIAL RESOLUTION HIGH ?
      YES: MAKE LOCAL REGION SIZE SMALL
      NO:  LEAVE LOCAL REGION SIZE

---

PROCESS 4: TERMINATE OF ITERATIVE ESTIMATION ?
     YES:           => END
     NO:  $i = i + 1$ => PROCESS 1

FIG.24

START OF MEASUREMENT OF DISPLACEMENT VECTOR DISTRIBUTION
$d(x,y,z)$ IN SOI, ROI ($i = 1$)
METHOD 4-4 BASED ON METHOD 2-4 (2D DISPLACEMENT VECTOR
    MEASUREMENT IN 2D ROI)
METHOD 5-4 BASED ON METHOD 3-4 (ONE DIRECTION
    DISPLACEMENT COMPONENT DISTRIBUTION IN 1D ROI)
METHOD 6-4 BASED ON METHOD 3-4

↓

PROCESS 1:
· AT EACH POINT $(x,y,z)$ IN SOI, ROI
    PROCESS 1 OF METHOD 2-1, 3-1:
        PHASE MATCHING USING (SMOOTHED) i-1TH ESTIMATE
        $d_{i-1}(x,y,z)$ ($d_0(x,y,z)$: INITIAL VALUE)
· ESTIMATE OF RESIDUAL DISPLACEMENT VECTOR
    DISTRIBUTION $u_i(x,y,z)$ IN SOI, ROI UTILIZING
    LEAST-SQUARES METHOD, REGULARIZATION METHOD

↓

PROCESS 2: UPDATE OF ESTIMATE
        OF DISPLACEMENT VECTOR DISTRIBUTION:
· $d_i(x,y,z)$ = (SMOOTHED) $d_{i-1}(x,y,z)$ + $u_i(x,y,z)$
· OCCASIONALLY, SMOOTHING OF $d_i(x,y,z)$
    [LOW PASS FILTERING, MEDIAN FILTERING]

↓

PROCESS 3: MAKE SPATIAL RESOLUTION HIGH ?
    YES: MAKE LOCAL REGION SIZE SMALL
    NO:  LEAVE LOCAL REGION SIZE

↓

PROCESS 4: TERMINATE OF ITERATIVE ESTIMATION ?
    YES:                => END
    NO:  $i = i + 1$    => PROCESS 1

START OF MEASUREMENT OF DISPLACEMENT VECTOR DISTRIBUTION
d(x,y,z) IN SOI, ROI (i = 1)
METHOD 4-5 BASED ON METHOD 2-5 (2D DISPLACEMENT VECTOR
    MEASUREMENT IN 2D ROI)
METHOD 5-5 BASED ON METHOD 3-5 (ONE DIRECTION
    DISPLACEMENT COMPONENT DISTRIBUTION IN 1D ROI)
METHOD 6-5 BASED ON METHOD 3-5

---

PROCESS 1:
- AT EACH POINT (x,y,z) IN SOI, ROI
   PROCESS 1 OF METHOD 2-1, 3-1:
     PHASE MATCHING USING (SMOOTHED) i-1TH ESTIMATE
     $d_{i-1}(x,y,z)$ ($d_0(x,y,z)$: INITIAL VALUE)
- ESTIMATE OF RESIDUAL DISPLACEMENT VECTOR
   DISTRIBUTION $u_i(x,y,z)$ IN SOI, ROI UTILIZING
   LEAST-SQUARES METHOD, REGULARIZATION METHOD
- POSSIBILITY OF DIVERGENCE OF PHASE MATCHING
   IN SOI, ROI?
        YES => PROCESS 2
        NO:  => METHOD 4-1 (5-1, 6-1)

---

PROCESS 2: UPDATE OF ESTIMATE
        OF DISPLACEMENT VECTOR DISTRIBUTION:
- $d_i(x,y,z)$ = (SMOOTHED) $d_{i-1}(x,y,z)$ + $u_i(x,y,z)$
- OCCASIONALLY, SMOOTHING OF $d_i(x,y,z)$
   [LOW PASS FILTERING, MEDIAN FILTERING]

---

PROCESS 3: MAKE SPATIAL RESOLUTION HIGH ?
      YES: MAKE LOCAL REGION SIZE SMALL
      NO:  LEAVE LOCAL REGION SIZE

---

PROCESS 4: TERMINATE OF ITERATIVE ESTIMATION ?
     YES:            => END
     NO: i = i + 1  => PROCESS 1

DISPLACEMENT MEASUREMENT METHOD AND APPARATUS, STRAIN MEASUREMENT METHOD AND APPARATUS, ELASTICITY AND VISCO-ELASTICITY CONSTANTS MEASUREMENT APPARATUS, AND THE ELASTICITY AND VISCO-ELASTICITY CONSTANTS MEASUREMENT APPARATUS-BASED TREATMENT APPARATUS

BACKGROUND OF THE INVENTION

1. Field of the Invention

The present invention relates to an apparatus and method for low-destructively (low-invasively) measuring mechanical properties within object such as structures, substances, materials, living tissues (liver, prostate, breast, etc.). For instance, measured can be, due to applied stress and/or vibration by arbitrary mechanical sources, generated displacement vector, strain tensor, strain rate tensor, acceleration vector, or velocity vector, etc. within the body. Furthermore, from these measured deformation data, following constants can be measured, elastic constants such as shear modulus, Poisson's ratio, etc., visoc elastic constants such as visco shear modulus, visco Poisson's ratio, etc., delay times or relaxation times relating these elastic constants and visco elastic constants, or density.

On typical applied field, i.e., medical field, such as ultrasonic diagnosis, nuclear magnetic resonance diagnosis, light diagnosis, radio therapeutics, the present method and apparatus can be applied for monitoring tissue degeneration, i.e., treatment effectiveness. Otherwise, on structures, substances, materials, living tissues, measured static and/or dynamic mechanical properties can be utilized for evaluation, examination, diagnosis, etc.

2. Description of a Related Art

For instance, on medical field (liver, prostate, breast, etc.), lesions are proposed to be treated by cryotherapy, or by applying radioactive ray, high intensity focus ultrasound, laser, electromagnetic RF wave, micro wave, etc. In these cases, the treatment effectiveness is proposed to be monitored. Moreover, chemotherapy (anti-cancer drag etc.) effectiveness is also proposed to be monitored. For instance, on radiotherapy etc., the treatment effectiveness can be confirmed by low-invasively measuring degeneration (including temperature change) of the lesion. Otherwise, due to applied stress to the tissue part of interest including lesions, generated deformations and deformation changes are measured, from which the pathological state of the tissue is evaluated such as elastic constants etc. Thus, based on the measured distinct pathological state, the part of interest is diagnosed, or treatment effectiveness is observed.

Temperature is known to have high correlations with elastic constants, visco elastic constants, delay times or relaxation times relating elastic constants and visco elastic constants, and density, etc. Therefore, by measuring the following constants, temperature distribution can be measured, i.e., elastic constants such as shear modulus, Poisson's ratio, etc., visco elastic constants such as visco shear modulus, visco Poisson's ratio, etc., delay times or relaxation times relating these elastic constants and visco elastic constants, or density.

In the past, elastic constants and visco elastic constants have been measured by applying stress at many points and by measuring the responses such as stresses and strains. That is, stress meter and strain meter are used, and sensitivity analysis is numerically performed with utilization of finite difference method or finite element method. Otherwise, in addition to elastic constants, visco elastic constants such as visco shear modulus, visco Poisson's ratio, etc. has been also measured by estimating the shear wave propagation velocity generated by applying vibrations.

As other monitoring techniques, temperature distribution is measured by evaluating nuclear magnetic resonance frequency, electric impedance, ultrasound velocity, etc. However, to measure temperature, these techniques need other relating physical properties of the target tissue. If degeneration occurs on the part of region, the relating physical properties also change; thus resulting severe limitations of the temperature measurement.

Other disadvantage is that the past measurement technique needs many independent deformation fields generated by mechanical sources outside the target body. However, if there exist internal mechanical sources or mechanical sources are uncontrollable, the technique becomes unavailable. That is, the past technique needs all information about mechanical sources, such as positions, force directions, force magnitudes, etc. Moreover, the technique needs stress data and strain data at the target body surface, and needs whole body model (finite difference method or finite element method). Furthermore, low are spatial resolutions of measured elastic constants and visco elastic constants from shear wave velocity.

On the other hand, medical ultrasound diagnosis apparatus can low-invasively image tissue distribution by converting ultrasonic echo signals (echo signals) to image, after transmitting ultrasonic pulses to target tissue and receiving the echo signals at ultrasound transducer. Thus, by ultrasonically measuring tissue displacements generated due to arbitrary mechanical sources, or by measuring generated tissue strains, tissue elastic constants, etc., differences of between lesion and normal tissue can be observed low-invasively. For instance, measured within the body can be, due to applied stress and/or vibration by arbitrary mechanical sources, generated displacement vector, strain tensor, strain rate tensor, acceleration vector, velocity vector, etc. Furthermore, from these measured deformation data, following constants can be measured, elastic constants such as shear modulus, Poisson's ratio, etc., visco elastic constants such as visco shear modulus, visco Poisson's ratio, etc., delay times or relaxation times relating these elastic constants and visco elastic constants, or density.

Then, in the past, tissue displacement has been proposed to be measured to low-invasively diagnose tissue and lesion by evaluating the echo signal changes of more than one time transmitting signal. From the measured displacement distribution, strain distribution is obtained, by which distribution of pathological state of tissue has been proposed to be diagnosed (Japanese Patent Application Publication JP-A-7-55775, JP-A-2001-518342). Specifically, 3 dimensional (3D), 2D, or 1D region of interest (ROI) are set in the target body, and distributions of three, two, or one displacement component are measured, from which in addition to strain tensor distribution, elastic constant distributions, etc. are also numerically obtained.

In addition to ultrasound transducer, as the displacement (strain) sensor, utilized can be known contact or non-contact sensors such as electromagnetic wave (including light) detector etc. As mechanical sources, compressor and vibrator can be, transducer-mounted apparatuses, not transducer-mounted ones, internal heart motion, respiratory motion. If ROI is deformed by ultrasound transmitted from sensor, there may not need other mechanical sources except for the sensor. In addition to the stationary elastic constants, difference of the tissue pathological state includes dynamic changes of elastic constants and temperature due to treatment.

However, as the classical tissue displacement measurement methods assume tissue being deformed only in the axial (beam) direction, when tissue also moves in lateral (scan) direction, the classical method has low axial measurement accuracy. That is, the displacement was determined only by 1D axial processing of ultrasound echo signals (hereafter, echo signal includes rf echo signal, quadrate detection signal, envelop detection signal, and complex signal).

Recently, displacement accuracy is improved by us through development of 2D displacement vector measurement method, i.e., phase gradient estimation method of the 2D echo cross-spectrum based on so-called the 2D cross-correlation processing and the least squares processing. This method can suitably cope with internal, uncontrollable mechanical sources (e.g., heart motion, respiratory motion, blood vessel motion, body motion, etc.).

However, strictly speaking, measurement accuracy of actual 3D tissue displacement becomes low because the method can measure by 2D processing of echo signals two displacement components or by 1D processing one displacement component.

Particularly, as lateral component of echo signal has a narrow bandwidth and has no carrier frequency, lateral displacement measurement accuracy and spatial resolution are much lower compared with axial ones. Thus, the low lateral measurement accuracy degrades the 3D displacement vector measurement and the 3D strain tensor measurement.

Furthermore, when large displacement needs to be handled, before estimating the gradient of the cross-spectrum phase, the phase must be unwrapped, or the displacement must be coarsely estimated by cross-correlation method as multiples of sampling intervals. Thus, measurement process had become complex one.

SUMMARY OF THE INVENTION

The first purpose of the present invention is to provide an apparatus and method for low-destructively measuring mechanical properties within object such as structures, substances, materials, living tissues (liver, prostate, breast, etc.), even if there exists internal, or uncontrollable mechanical sources. The first purpose of the present invention is, for instance, for diagnosing and monitoring treatment effectiveness on living tissue, to provide the measurement technique of following constants, elastic constants such as shear modulus, Poisson's ratio, etc., visco elastic constants such as visco shear modulus, visco Poisson's ratio, etc., delay times or relaxation times relating these elastic constants and visco elastic constants, or density.

The second purpose of the present invention is to provide the low-invasive treatment technique with utilization of low-invasive measurement of the following constants, elastic constants such as shear modulus, Poisson's ratio, etc., visco elastic constants such as visco shear modulus, visco Poisson's ratio, etc., delay times or relaxation times relating these elastic constants and visco elastic constants, or density.

The third purpose of the present invention is to improve measurement accuracy of displacement vector distribution generated in 3D, 2D (including or not including beam direction), or 1D (beam direction or scan direction) ROI in the target body when estimating gradient of the echo cross-spectrum phase. Cross-spectrum can be also estimated by Fourier's transform of echo cross-correlation function.

The fourth purpose of the present invention is to simplify calculation process into one without unwrapping the cross-spectrum phase nor utilizing cross-correlation method; thus reducing calculation amount and shortening calculation time.

The fifth purpose of the present invention is to improve measurement accuracy of lateral displacements (orthogonal directions to beam direction).

In the preferred embodiment of the present invention, above-described purposes are achieved.

All the displacement measurement methods related to the present invention allow measuring local displacement vector or local displacement vector components from the phases of the ultrasound echo signals acquired from the target as the responses to more than one time transmitted ultrasound.

One method measures the displacement vector component from the gradient of the cross-spectrum phase evaluated from echo signals acquired at two different time, i.e., before and after tissue deformation. The 3D processing yields from 3D cross-spectrum phase $\theta(\omega x,\omega y,\omega z)$ accurate measurements of 3D displacement vectors $((d=(dx,dy,dz)^T)$ in 3D ROI, and consequently, results in measurements of the more accurate displacement vector components compared with corresponding ones measured by 2D processing (2D cross-spectrum phase: $\theta(\omega x,\omega y)$, or $\theta(\omega y,\omega z)$, or $\theta(\omega x,\omega z)$) and 1D processing (1D cross-spectrum phase: $\theta(\omega x)$, or $\theta(\omega y)$, or $\theta(\omega z)$).

When measuring displacement from the gradient of the echo cross-spectrum phase, to result the more accurate measurement accuracy, the least squares method can be applied with utilization as the weight function of the squares of the cross-spectrum usually normalized by the cross-spectrum power, where, to stabilize the measurement, the regularization method can be applied, by which a priori information can be incorporated, i.e., about within the ROI the magnitude of the unknown displacement vector, spatial continuity and differentiability of the unknown displacement vector distribution, etc. The regularization parameter depends on time-space dimension of the ROI, direction of the unknown displacement component, position of the unknown displacement vector, etc. Otherwise, directional independent regularization utilize the mechanical properties of tissue (e.g., incompressibility) and compatibility conditions of displacement vector distribution and displacement component distribution.

The displacement measurement apparatus related to the present invention can be equipped with the following means: displacement (strain) sensor (transducer to transmit ultrasounds to the target, and detect echo signals generated in the target), relative position controller and relative direction controller between the sensor and the target, means of transmitting/receiving (transmitter of driving signals to the sensor, and receiver of the echo signals detected at the sensor), means of data processing (controller of the driving signals of the means of transmitting, and processor of the received echo signals of means of receiving), and means of data storing (storage of echo signals, measured deformation data).

The means of data processing also measures the local displacement vector or the local displacement vector components utilizing the stated displacement measurement methods from the phases of the ultrasound echo signals acquired from the target as the responses to more than one time transmitted ultrasound.

The strain tensor measurement apparatus related to the first point of view of the present invention can be equipped with the displacement measurement apparatus, and the means of data processing can yield strain tensor components by spatial differential filtering with suitable cut off frequency in spatial domain or frequency domain the measured 3D, or 2D displacement vector components, or measured one direction displacement component in the 3D, 2D, or 1D ROI. The means of data processing can also yield strain rate tensor components, acceleration vector components, or velocity vector components by time differential filtering with suitable cut off frequency in time domain or frequency domain the measured time series of displacement components, or strain components.

The strain tensor measurement method related to the present invention also allow directly measuring the local strain tensor or the local strain tensor components from the phases of the ultrasound echo signals acquired from the target as the responses to more than one time transmitted ultrasound.

The strain tensor measurement apparatus related to the second point of view of the present invention can be equipped with the following means: displacement (strain) sensor (transducer to transmit ultrasounds to the target, and detect echo signals generated in the target), relative position controller and relative direction controller between the sensor and the target, means of transmitting/receiving (transmitter of driving signals to the sensor, and receiver of the echo signals detected at the sensor), means of data processing (controller of the driving signals of the means of transmitting, and processor of the received echo signals of means of receiving), and means of data storing (storage of echo signals, measured deformation data).

The means of data processing also directly measures the local strain tensor or the local strain tensor components utilizing the stated direct strain measurement methods from the phases of the ultrasound echo signals acquired from the target as the responses to more than one time transmitted ultrasound.

The elasticity and visco-elasticity constants measurement apparatus related to the first point of view of the present invention can be equipped with the following means: means of data storing (storage of at least one of strain tensor data, strain rate tensor data, acceleration vector data, elastic constants, visco elastic constants, or density measured in the ROI set in the target), and means of calculating elastic and visco elastic constants (calculator of at least one of elastic constants, visco elastic constants, or density of arbitrary point in the ROI from at least one of the measured strain tensor data, strain rate tensor data, or acceleration vector data).

The means of calculating elastic and visco elastic constants numerically determines at least one of the elastic constants, visco elastic constants, or density from the first order partial differential equations relating at least one of the elastic constants, visco elastic constants, or density to at least one of the strain tensor data, strain rate tensor data, acceleration vector data. Time delays or relaxation times can also be determined by ratio of the corresponding elastic constant and visco elastic constant.

The elasticity and visco-elasticity constants measurement apparatus related to the second point of view of the present invention can be equipped with the following means: means of data storing (storage of at least one of strain tensor data, strain rate tensor data, acceleration vector data, elastic constants, visco elastic constants, or density measured in the ROI including lesions), means of calculating elastic and visco elastic constants (calculator of at least one of elastic constants, visco elastic constants, or density of arbitrary point in the ROI from at least one of the measured strain tensor data, strain rate tensor data, or acceleration vector data), and means of output of degeneration information on parts including the lesions (output means of degeneration information based on calculated at least one of the elastic constants, visco elastic constants, or density).

The means of calculating elastic and visco elastic constants numerically determines at least one of the elastic constants, visco elastic constants, or the density from the first order partial differential equations relating at least one of the elastic constants, visco elastic constants, or density to at least one of the strain tensor data, strain rate tensor data, acceleration vector data.

The elasticity and visco-elasticity constants measurement apparatus-based treatment apparatus related to the present invention can be equipped with the following means: treatment transducer arrayed with more than one oscillator, means (circuit) of treatment transmitting (transmitter of driving signals to each oscillator of the treatment transducer array), diagnosis transducer arrayed with more than one oscillator, means (circuit) of diagnosis transmitting (transmitter of driving signals to each oscillator of the diagnosis transducer array), means (circuit) of receiving (receiver of the echo signals detected at the oscillators of the transducers and matcher of the echo signals based on their phases), means of calculating elastic and visco elastic constants (calculator of at least one of elastic constants, visco elastic constants, or density from the matched echo signals), means of output of degeneration information on parts including the lesions (output means of degeneration information based on calculated at least one of the elastic constants, visco elastic constants, or density), controller of the means (circuit) of treatment transmitting, means (circuit) of diagnosis transmitting, means (circuit) of receiving, and means of calculating elastic and visco elastic constants, and the input means of commands and conditions into the controller.

The controller is not only equipped with functions for controlling the means (circuit) of diagnosis transmitting and means (circuit) of receiving based on the commands and the conditions, but also with functions for deforming the ROI in the target based on the commands and the conditions, and for controlling the means (circuit) of treatment transmitting to control the treatment ultrasound beam transmitted from the treatment transducer based on the commands and the conditions.

The means of calculating elastic and visco elastic constants obtains the matched echo signals in the ROI based on the commands given from the controller, and calculates at least one of strain tensor data, strain rate tensor data, or acceleration vector data in the ROI, and subsequently calculates from these deformation data at least one of elastic constants, visco elastic constants, or density in the ROI. Here, controlled of treatment ultrasound beam may be beam focus position, treatment interval, ultrasound beam power, ultrasound beam strength, transmit term, beam shape (apodization), etc. The oscillators may serve both as treatment ones and diagnosis ones.

BRIEF DESCRIPTION OF THE DRAWING

FIG. 2 shows illustration of a displacement (strain) sensor applicable to the present invention;

FIG. 10 shows flowchart of method of 3D displacement vector distribution in 3D space (method 1-1), of method of 2D displacement vector distribution in 2D region (method 2-1), of method of one direction displacement component distribution in 1D region (method 3-1);

FIG. 11 shows flowchart of method of 3D displacement vector distribution in 3D space (method 1-2), of method of 2D displacement vector distribution in 2D region (method 2-2), of method of one direction displacement component distribution in 1D region (method 3-2);

FIG. 12 shows flowchart of method of 3D displacement vector distribution in 3D space (method 1-3), of method of 2D displacement vector distribution in 2D region (method 2-3), of method of one direction displacement component distribution in 1D region (method 3-3);

FIG. 13 shows flowchart of method of 3D displacement vector distribution in 3D space (method 1-4), of method of 2D displacement vector distribution in 2D region (method 2-4), of method of one direction displacement component distribution in 1D region (method 3-4);

FIG. 14 shows flowchart of method of 3D displacement vector distribution in 3D space (method 1-5), of method of 2D displacement vector distribution in 2D region (method 2-5), of method of one direction displacement component distribution in 1D region (method 3-5);

FIG. 21 shows flowchart of method of 2D displacement vector distribution in 3D space (method 4-1), of method of one direction displacement component distribution in 3D space (method 5-1), and of method of one direction displacement component distribution in 2D region (method 6-1);

FIG. 22 shows flowchart of method of 2D displacement vector distribution in 3D space (method 4-2), of method of one direction displacement component distribution in 3D space (method 5-2), and of method of one direction displacement component distribution in 2D region (method 6-2);

FIG. 23 shows flowchart of method of 2D displacement vector distribution in 3D space (method 4-3), of method of one direction displacement component distribution in 3D space (method 5-3), and of method of one direction displacement component distribution in 2D region (method 6-3);

FIG. 24 shows flowchart of method of 2D displacement vector distribution in 3D space (method 4-4), of method of one direction displacement component distribution in 3D space (method 5-4), and of method of one direction displacement component distribution in 2D region (method 6-4);

FIG. 25 shows flowchart of method of 2D displacement vector distribution in 3D space (method 4-5), of method of one direction displacement component distribution in 3D space (method 5-5), and of method of one direction displacement component distribution in 2D region (method 6-5);

DESCRIPTION OF THE PREFERRED EMBODIMENTS

The following is explanation in detail of conduct forms of the present invention with referring to figures.

Figure 1:
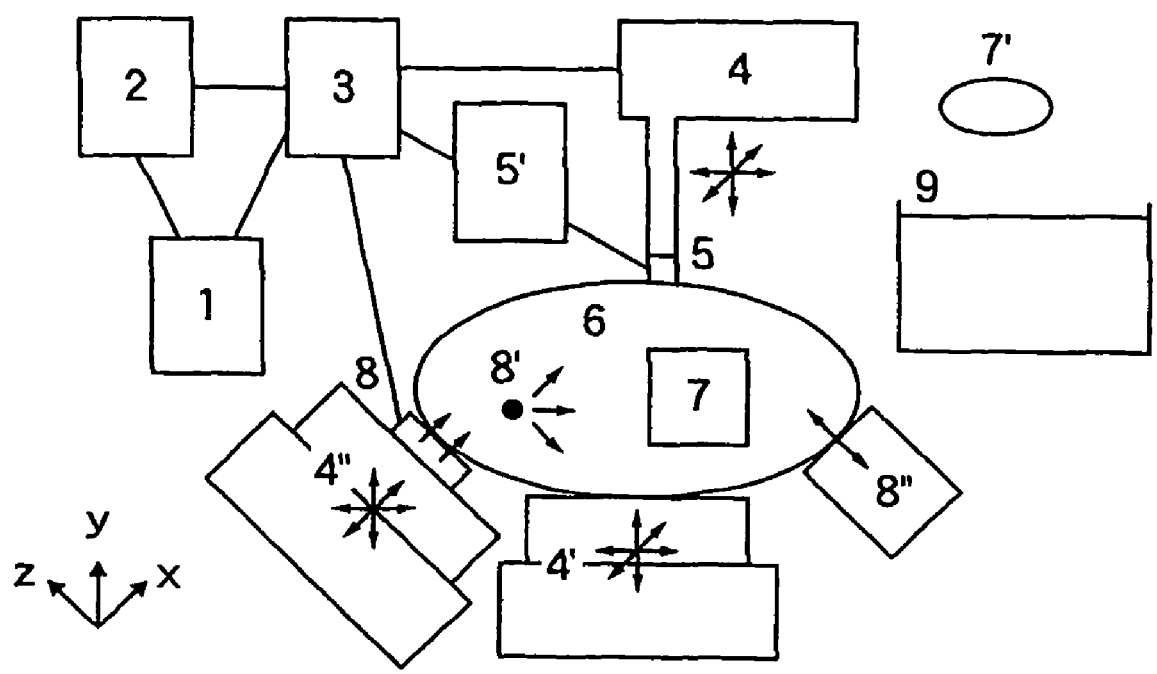
FIG. 1 shows a schematic representation of a global frame of displacement vector and strain tensor measurement apparatus, and elasticity and visco-elasticity constants measurement apparatus, related to one of conduct forms of the present invention.

FIG. 1 shows a schematic representation of a global frame of displacement vector and strain tensor measurement apparatus, and elasticity and visco-elasticity constants measurement apparatus, related to one of conduct forms of the present invention. This apparatus measures in 3D, 2D, or 1D ROI 7 set in measurement object 6 displacement vector component distributions, strain tensor component distributions, their time-space partial derivative distributions, etc. to obtain strain tensor field, strain rate tensor field, acceleration vector etc., from which this apparatus measures following constant distributions, i.e., elastic constants such as shear modulus, Poisson's ratio, etc., visco elastic constants such as visco shear modulus, visco Poisson's ratio, etc., delay times or relaxation times relating these elastic constants and visco elastic constants, or density.

As shown in FIG. 1, displacement (strain) sensor 5 can be directly contacted to object surface, or suitable medium can be put between the sensor and the object. On this conduct form, as the displacement (strain) sensor, ultrasound transducer is used. The transducer may have 1D or 2D array of oscillators.

Distance between the object 6 and the displacement (strain) sensor 5 can be mechanically controlled by position controller 4. Moreover, relative distance between the object 6 and the displacement (strain) sensor 5 can be mechanically controlled by position controller 4'. Ultrasound transmitter (ultrasound pulser) 5' is equipped to drive the displacement (strain) sensor 5, and 5' also serves as output controller, i.e., receiver with amplifier of echo signals detected at the displacement (strain) sensor 5. Furthermore, mechanical source

8 can be equipped to actively apply static compression, vibration, etc., and mechanical position controller 4', can be also equipped.

Output echo signals of output controller 5' are stored at storage 2 passing through measurement controller 3. The echo signals stored at storage 2 are read out by data processor 1, and displacement vector component distributions (time series) or strain tensor component distributions (time series) are directly calculated and obtained of arbitrary time in the ROI 7, and further calculated and obtained are as their time-space partial derivatives, i.e., strain tensor component distributions (time series), strain rate tensor component distributions (time series), acceleration vector component distributions (time series), etc. That is, when displacement vector component distributions are calculated of the ROI 7, strain tensor component distributions (time series) are obtained by implementing 3D, 2D, or 1D spatial differential filter to the obtained displacement vector component distributions (time series). The cut off frequencies of all the filters used in the present invention can be set different values freely at each point at each time in each spatio-temporal direction as those of usual filters. The acceleration vector component distributions (time series) are obtained by implementing time differential filter twice to the measured displacement vector component distributions (time series). The strain rate tensor component distributions (time series) are obtained by implementing spatial differential filter to the velocity vector component distributions (time series) obtained by implementing time differential filter to the displacement vector component distributions (time series), or by implementing time differential filter once to the measured strain tensor component distributions (time series). Moreover, when strain tensor component distributions (time series) are directly calculated of the ROI 7 and obtained, strain rate tensor component distributions (times series) are obtained by implementing time differential filter to the measured strain tensor component distributions (time series). Furthermore, this data processor 1 calculates following constant distributions, i.e., elastic constants such as shear modulus, Poisson's ratio, etc., visco elastic constants such as visco shear modulus, visco Poisson's ratio, etc., delay times or relaxation times relating these elastic constants and visco elastic constants, or density from the measured distributions of strain tensor components (time series), strain rate tensor components (time series), acceleration vector components (time series), etc. These calculated results are stored at the storage 2.

The measurement controller 3 controls the data processor 1, the position controller 4 and 4", and the transmitting/output controller 5'. The position controller 4' is not utilized when the object 6 is spatially fixed. When displacement (strain) sensor 5 is electronic scan type, position controller 4 is not always utilized. That is, it may be possible to measure without mechanical scanning. The displacement (strain) sensor 5 may be contacted on the object 6, or may not. That is, the displacement (strain) sensor 5 and the object 6 may be dipped in or immersed in water tank, for instance, when monitoring the treatment effectiveness of High Intensity Focus Ultrasound (HIFU).

Figure 3:
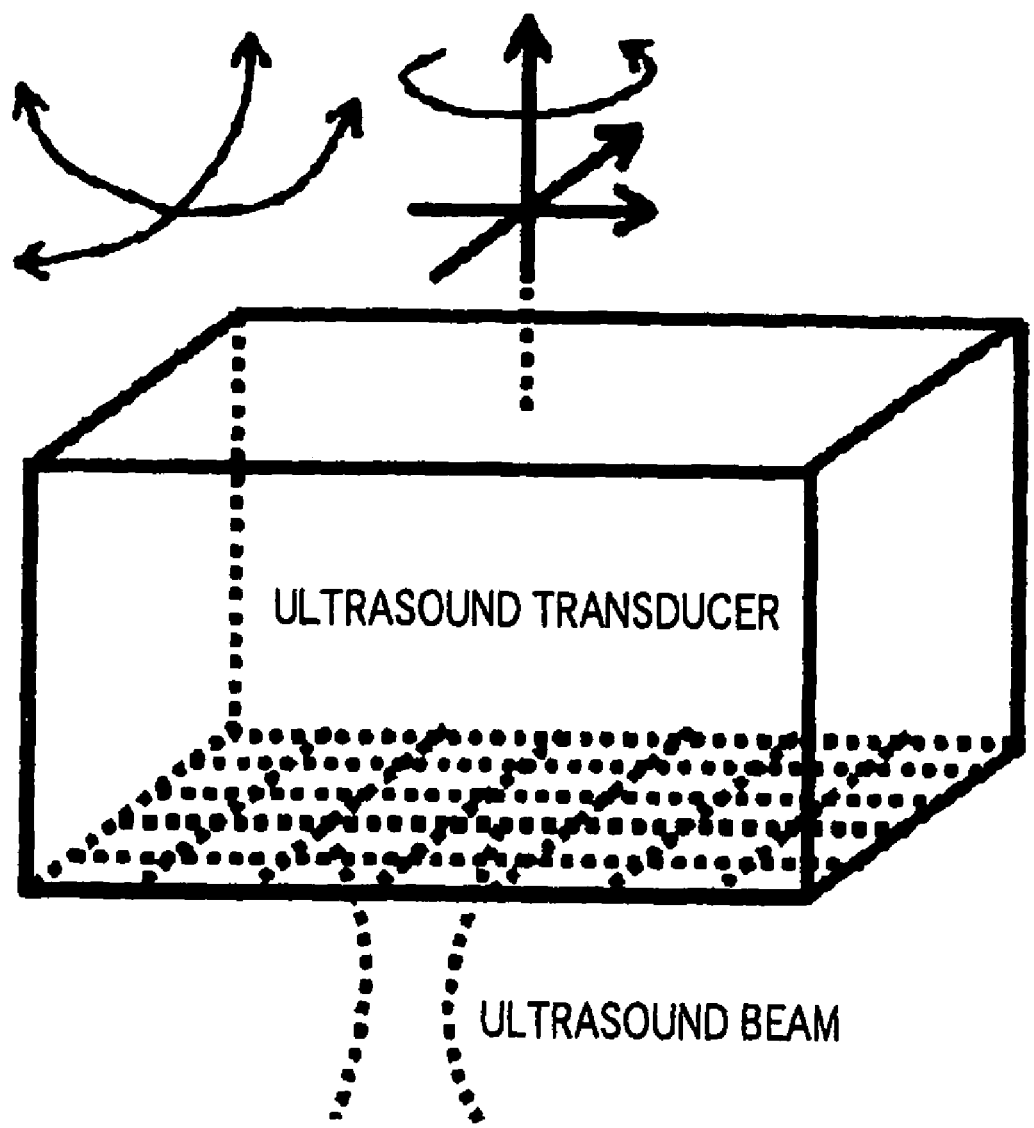
FIG. 3 shows illustration of mechanical scan movements of the displacement (strain) sensor.

The position controller 4 mechanically controls the relative position between the displacement (strain) sensor 5 and the object 6. Specifically, the position controller 4 realizes vertical, horizon, turn, and fan direction scan movements (FIG. 3). The output of the transmitting/output controller 5' is also stored at storage 2 successively or with given time intervals. The data processor 1 controls the transmitting/output controller 5', and acquires the echo's basic wave components, n-th harmonic wave components (n equals from 2 to N), or all the components in 3D, 2D, or 1D ROI 7, and implements below-described data processing to yield displacement data, strain data, strain rate data, or acceleration data, and stores measured these data in the storage 2.

The transmitting/output controller 5' and the data processor 1 obeys the commands of measurement controller 3, and carry out synthetic aperture processing, e.g., transmitting fixed focusing process, multi-transmitting fixed focusing process, receiving dynamic focusing process, etc. Furthermore, the transmitting/output controller 5' and the data processor 1 carry out apodization process of ultrasound signals, i.e., weighting process on each ultrasound transmitted/received at each oscillator to sharpen the synthesized ultrasound beam, and carry out beam steering process to acquire the echo signals of 3D, 2D, or 1D ROI.

Next explanation is in detail about displacement and strain measurement apparatus related to conduct forms of the present invention.

On this conduct form, as the displacement (strain) sensor 5, the following type ultrasound transducers can be utilized, i.e., 2D array being mechanical scan possible, 2D array being electronic scan possible, 1D array being mechanical scan possible, and 1D array being electronic scan possible.

On this conduct form, synthetic aperture can be performed. Also beam steering can be performed. When beam steering is performed, measured displacement component distributions and strain tensor component distributions are spatially interporated, after which these measured displacement component distributions (time series) and strain tensor component distributions (time series) are time-spatially differentiated to yield strain tensor component distributions (time series), strain rate tensor component distributions (time series), acceleration vector component distributions (time series), and velocity vector component distributions (time series).

Figure 4:
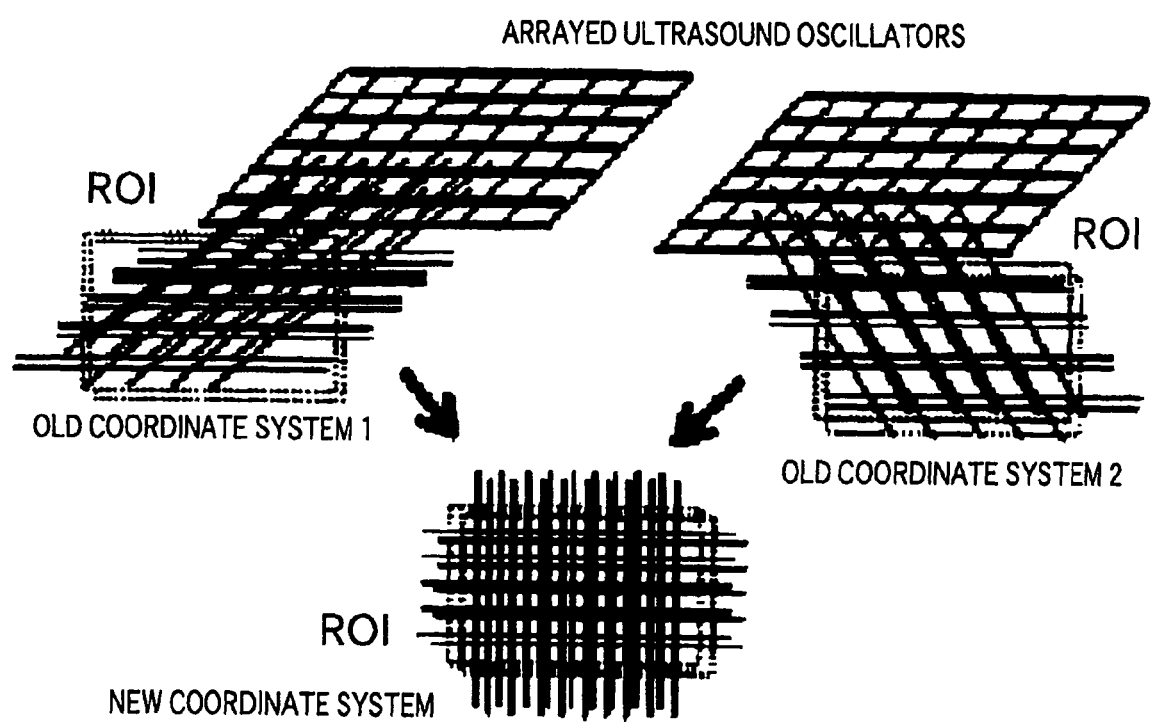
FIG. 4 shows illustration of beam steering, and spatial interporation of measured two displacement vector component distributions.
Figure 5:
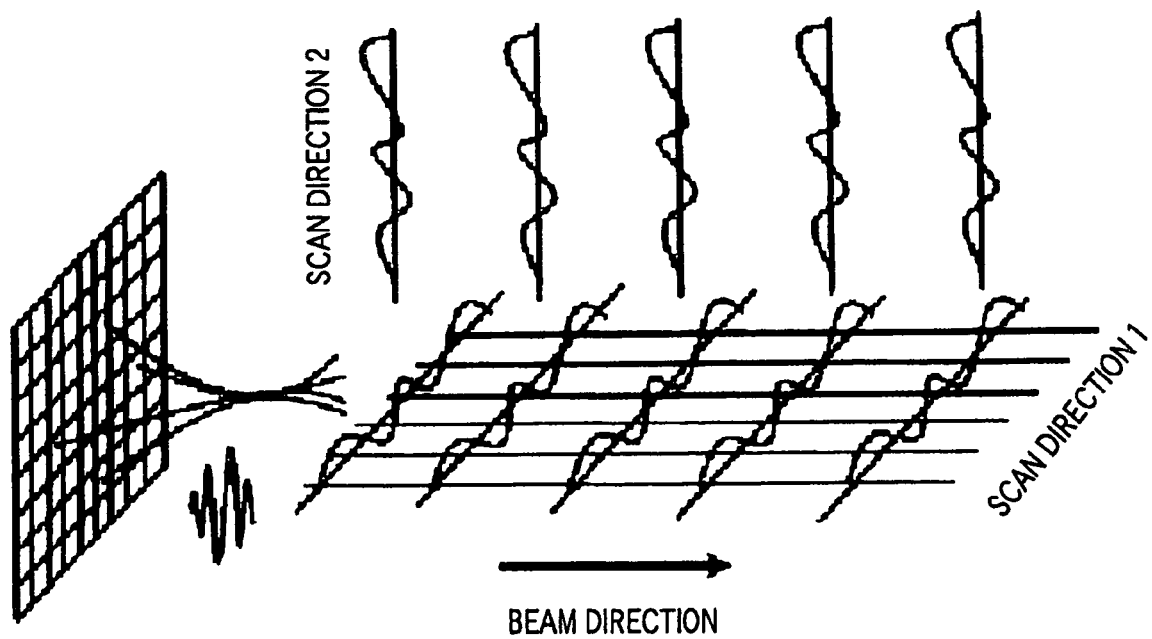
FIG. 5 shows illustration of transmitted beams whose amplitudes are sine modulated in scan directions.
Figure 6:
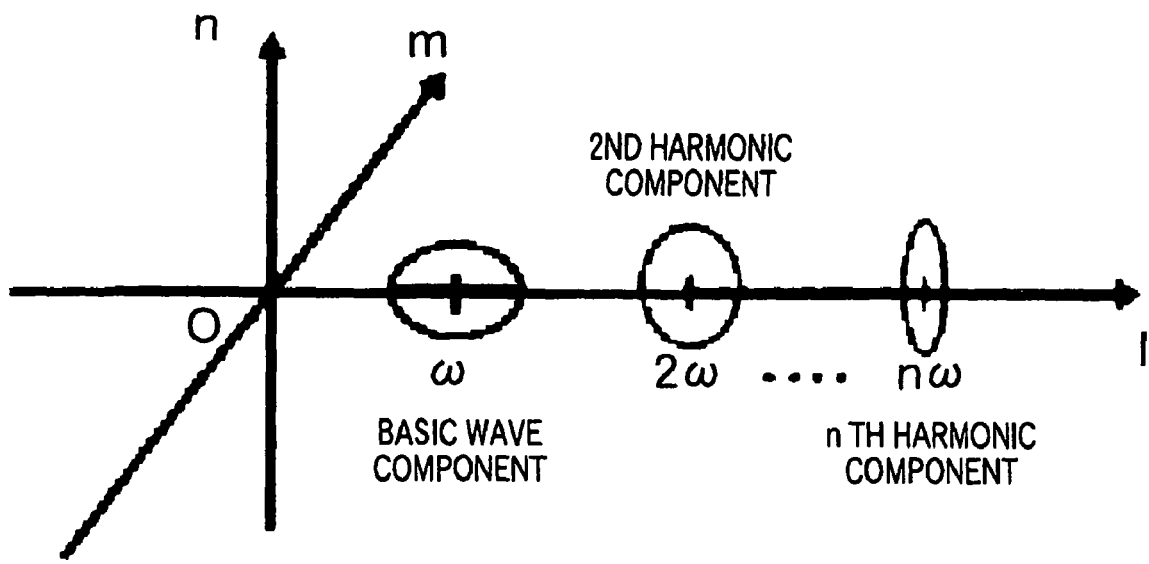
FIG. 6 shows illustration of a basic (n=1) wave component and n-th harmonic wave components (n equals from 2 to N) of ultrasound echo signal.

As measurement of the beam direction is considerably accurate compared with that of the orthogonal scan direction, to yield high accuracy displacement vector measurement, mechanical scan and/or beam steering can be performed. That is, echo data frames are acquired by performing mechanical scan and/or beam steering such that ultrasound beams are transmitted in three different directions when measuring 3D displacement vector, and in two different directions when measuring 2D displacement vector. From two echo data frames acquired by transmitting the ultrasound beams in same direction, accurately the distribution of displacement component in beam direction is measured, by which accurate 3D or 2D displacement vector distribution can be obtained (e.g., FIG. 4).

However, to obtain the final displacement vector distribution, displacement vector distributions on the different old discrete coordinates must be converted to ones on one new discrete coordinate. That is, by interporating the displacement component distribution measured on the old discrete coordinate, the displacement component can be obtained at the point of the new discrete coordinate. Concretely, displacement component distribution is Fourier's transformed, which is multiplied with complex exponential such that the phase is shifted. Thus, realized is spatial shifting of the displacement component distribution.

On this conduct form, amplitudes of transmitted beams can be sine modulated in scan directions.

The sine modulation frequency is better to be higher. However, as this modulation shifts in frequency domain in scan direction the band determined by beam width, based on the sampling theorem the modulation frequency needs to be set such that the highest frequency becomes less than the half of the sampling frequency determined by beam pitch. Thus, improved is measurement accuracy of displacement component distribution in scan direction being orthogonal to beam direction.

Based on these processes, obtained ultrasound echo signals in 3D, 2D, or 1D ROI can be effectively utilized, i.e., basic wave components, harmonic wave components (The carrier frequency higher, improved is measurement accuracy of displacement component in beam direction. The carrier frequency higher, the beam width narrower. Thus, as the bandwidth in scan direction is wider compared with the basic component wave, also improved is measurement accuracy of displacement component in scan direction.), or all the wave components due to low SNRs of only harmonic wave components.

That is, below-described displacement and strain measurement methods can utilize the ultrasound echo signals, or only extracted the basic wave components, or only extracted the n-th harmonic wave components (n equals from 2 to N), or these combinations (methods from 1-1 to 1-5, from 2-1 to 2-5, from 3-1 to 3-5, from 4-1 to 4-5, from 5-1 to 5-5, from 6-1 to 6-5.).

These stated displacement and strain measurement methods base on iteratively updating the displacement estimate utilizing the estimated remaining error data (estimated residual displacement data). The initial estimate is set based on the a priori knowledge about measurement target, i.e., displacement distribution, strain distribution, strain rate distribution, acceleration distribution, or velocity distribution. Finally obtained are accurate displacement vector distribution (time series), displacement vector component distributions (time series), strain tensor distribution (time series), strain tensor component distributions (time series), strain rate tensor distribution (time series), strain rate tensor component distributions (time series), acceleration vector distribution (time series), acceleration vector component distributions (time series), velocity vector distribution (time series), or velocity vector component distributions (time series).

However, when stressing on real-time processing, measurement can be finished only with the once estimation.

During iterative estimation of the displacement vector and residual displacement vector, when estimation errors are detected a priori as the points of time-space magnitude and time-space continuity, for instance, the estimates can be cut by compulsion such that the estimates range from the given smallest value to the given largest value, or such that the difference between the estimates of the neighboring points settle within the given ranges.

On these stated iterative displacement and strain measurement methods, all the methods for estimating the residual displacement vector component or the displacement vector component utilize as the index the phases of the ultrasound echo signals acquired at more than one time. First of all, one of these methods is used to explain the iterative methods, i.e., the method estimating displacement from the gradient of the phase of the cross-spectrum of ultrasound echo signals acquired twice.

The displacement and strain measurement methods can be implemented each on extracted the basic wave signals and the n-th harmonic wave components (n equals from 2 to N). In this case, the final measurement result can be obtained as the mean displacement data weighted by the power ratio of the cross-spectrums etc.

In addition, when measuring the displacement from the gradient of the cross-spectrum phase utilizing least squares method, data processor also utilize the regularization method based on the a priori knowledge, which improves stability, accuracy, and spatial resolutions of the measurement of the displacement vector distribution, or the displacement vector component distributions.

In the past, when large displacement needs to be handled, before estimating the gradient of the cross-spectrum phase, the phase had been unwrapped, or the displacement had been coarsely estimated by cross-correlation method. Thus, measurement procedure had become complex one. To cope with these complexity, the measurement procedure is made simpler without these processes by introducing process of thinning out data and process of remaking data interval original. Thus, implemented soft amount and calculation time are reduced. Occasionally, the regularization may not be performed.

However, as other method, before estimating the gradient of the cross-spectrum phase, the phase can also be unwrapped, or the displacement can also be coarsely estimated by cross-correlation method. Also in this case, when measuring the local displacement from the gradient of the cross-spectrum phase, a priori knowledge about the displacement distribution in the ROI can be incorporated by utilizing the regularization method, where the least squares method utilizes as the weight function the squares of the cross-spectrum usually normalized by the cross-spectrum power. Freely, when estimating the gradient of the cross-spectrum phase, acquired ultrasound echo signals can be thinned out in each direction with constant intervals.

These cases handles the gradient of the local 3D, 2D or 1D cross-spectrum phase evaluated on 3D, 2D, or 1D ultrasound echo signals acquired at more than one time from 3D space, 2D or 1D region in the object. Stably measured with high accuracy and high spatial resolutions are 3D displacement vector component distributions in the 3D SOI (space of interest), 2D displacement vector component distributions in the 2D ROI, one direction displacement component distribution in the 1D ROI, 2D displacement vector component distributions or one direction displacement component distribution in the 3D SOI, or one direction displacement component distribution in the 2D ROI.

The displacement and strain measurement apparatus of the present invention measures in the 3D SOI, 2D, or 1D ROI in the object the displacement vector distribution, the strain tensor distribution, the strain rate tensor distribution, the acceleration vector distribution, velocity vector distribution, etc. from ultrasound echo signals measured in 3D SOI, 2D, or 1D ROI (referred to 3D, 2D, 1D ultrasound echo signals). The displacement and strain measurement apparatus can be equipped with:

displacement (strain) sensor (ultrasound transducer), relative position controller and relative direction controller between the sensor and the target (vertical, horizon, turn, and fan direction scan movements), transmitter (ultrasound pulser)/output controller (receiver and amplifier), means of data processing (synthetic aperture process: transmitting fixed focusing process, multi-transmitting fixed focusing process, receiving dynamic focusing process etc., apodization), means of data storing (storage of echo signals), means of (signal) data processing (calculation of displacement vector distribution, strain tensor distribution, strain rate tensor distribution, acceleration vector distribution, velocity vector distribution, etc.), and means of data storing (storage of the displacement vector distribution, strain tensor distribution, strain rate tensor distribution, acceleration vector distribution, velocity vector distribution, etc.).

In this case, the means of data processing can yield strain tensor components by implementing spatial 3D, 2D, or 1D differential filter with cut off frequency or multiplying Fourier's transform of the differential filter in frequency domain to 3D displacement vector component distributions in the 3D SOI (space of interest), 2D displacement vector component distributions in the 2D ROI, one direction displacement component distribution in the 1D ROI, 2D displacement vector component distributions or one direction displacement component distribution in the 3D SOI, or one direction displacement component distribution in the 2D ROI. Moreover, by implementing time differential filter with cut off frequency or multiplying Fourier's transform of the differential filter in frequency domain to time series of these, the strain rate tensor component distributions, acceleration vector component distributions, velocity vector component distributions. Moreover, the strain rate tensor component distributions can be obtained from directly measured strain tensor component distributions.

The displacement and strain measurement apparatus can be also equipped with static compressor or vibrator as mechanical source to generate at least one strain tensor field (one displacement vector field) in the 3D SOI, 2D, or 1D ROI in the object. On this case, generated due to body motion (heart motion, blood vessel motion, respiratory), the strain tensor field (displacement vector field) can be also measured in the 3D SOI, 2D, or 1D ROI in the object.

The following ultrasound transducer type can be utilized, i.e., ultrasound oscillator being mechanical scan possible, electronic scan type 2D ultrasound oscillator array (being mechanical scan possible), and 1D ultrasound oscillator array (being mechanical scan possible). Thus, echo signal is synthesized one. When the displacement (strain) sensor is contacted on the object, the contact part can be come mechanical source. That is, the displacement (strain) sensor also serves as compressor or vibrator. When the part of lesion is dipped in or immersed in water tank to carry out treatment with High Intensity Focus Ultrasound (HIFU), the object can be non-contactly measured by dipping in or immersing the displacement (strain) sensor as well in water tank.

Moreover, when the displacement (strain) sensor is directly contacted to object surface as mechanical source to stably measure elastic constant distributions and visco elastic constant distributions, suitable reference medium can be put between the sensor and the object. In this case, the reference medium can also be mounted (installed) on the transducer.

Basically, the means of data processing can yield strain tensor component distributions, stain rate tensor component distributions, acceleration vector component distributions, or velocity vector component distributions from the obtained deformation data utilizing the displacement (strain) sensor from synthesized ultrasound echo in 3D SOI, 2D or 1D ROI, i.e., 3D displacement vector component distributions in the 3D SOI, 2D displacement vector component distributions in the 2D ROI, one direction displacement component distribution in the 1D ROI, 2D displacement vector component distributions or one direction displacement component distribution in the 3D SOI, or one direction displacement component distribution in the 2D ROI. Moreover, the strain rate tensor component distributions can be obtained from directly measured strain tensor component distributions.

In this case, the means of data processing can yield displacement component distributions and strain tensor component distributions from ultrasound echo signals acquired in each dimensional ROI with beam steering as well as synthetic aperture processing, from which obtained can be strain tensor component distributions, strain rate tensor component distributions, acceleration vector component distributions, and velocity vector component distributions.

Moreover, in this case, the means of data processing can yield displacement component distributions and strain tensor component distributions from ultrasound echo basic wave components, ultrasound echo harmonic wave components, or all the ultrasound echo components, from which obtained can be strain tensor component distributions, strain rate tensor component distributions, acceleration vector component distributions, and velocity vector component distributions.

Here, the sine modulation frequency is better to be higher. However, as this modulation shifts in scan direction in frequency domain the band determined by beam width, based on the sampling theorem the modulation frequency needs to be set such that the highest frequency becomes less than the half of the sampling frequency determined by beam pitch.

Furthermore, ultrasound echo signals can be acquired by combining the processing, i.e., synthetic aperture processing, beam steering, sine modulation of transmitted beams' amplitudes in scan directions. In this case, measured can be displacement vector component distribution from ultrasound echo basic wave components, ultrasound echo harmonic wave components, or all the ultrasound echo components.

When utilizing below-described displacement and strain measurement methods, as measurement of the beam direction is considerably accurate compared with that of the orthogonal scan direction, to yield high accuracy displacement measurements, mechanical scan and/or beam steering are performed. That is, echo data frames are acquired under object's pre- and post-deformation by performing mechanical scan and/or beam steering such that ultrasound beams are transmitted in three different directions when measuring 3D displacement vector, and in two different directions when measuring 2D displacement vector. From two echo data frames acquired by transmitting the ultrasound beams in same direction, accurately the distribution of displacement component in beam direction is measured, by which accurate 3D or 2D displacement vector distribution is obtained. To obtain the final displacement vector distribution, displacement vector distributions on the different old discrete coordinates must be converted to ones on one new discrete coordinate. That is, by interporating the displacement component distribution measured on the old discrete coordinate, the displacement component can be obtained at the point of the new discrete coordinate. Concretely, displacement component distribution is Fourier's transformed, which is multiplied with complex exponential such that the phase is shifted. Thus, realized is spatial shifting of the displacement component distribution. Strain tensor component distributions can be obtained from these displacement measurement data. Moreover, from these time series, obtained can be strain tensor rate component distributions, acceleration vector component distributions, velocity vector component distributions. Other displacement measurement methods and strain measurement methods can be also applied to the ultrasound echo time series data in similar ways.

Next explanation is in detail about displacement and strain measurement algorithm related to conduct forms of the present invention. The means of data processing 1 always carries out the below-explained calculation process or their combination, or as occasion demands.

(1) Calculation process of 3D displacement vector component distribution in 3D ROI (below-described methods from 1-1 to 1-5)
(2) Calculation process of 2D displacement vector component distribution in 2D ROI (below-described methods from 2-1 to 2-5)

(3) Calculation process of 1D (one direction) displacement component distribution in 1D ROI (below-described methods from 3-1 to 3-5)
(4) Calculation process of 2D displacement vector component distribution in 3D ROI (below-described methods from 4-1 to 4-5)
(5) Calculation process of 1D (one direction) displacement component distribution in 3D ROI (below-described methods from 5-1 to 5-5)
(6) Calculation process of 1D (one direction) displacement component distribution in 2D ROI (below-described methods from 6-1 to 6-5)

When beam steering is performed, at means data processing 1, measured displacement vector component distributions are spatially interporated.

With respect to displacement component distributions and strain component distributions obtained through the above calculation processes, means of data processing 1 performs differentiation such that the followings are obtained, i.e., at each time strain tensor component distributions, strain gradient component distributions, strain rate tensor component distributions, strain rate gradient component, acceleration vector component distributions, or velocity vector distributions. These calculated results are stored at storage 2. Moreover, these calculated results are displayed on display apparatus such as CRT (color or gray scaled) in real-time or in quasi real-time.

As static or motion image, or time course (difference) image, etc., the followings can be displayed, i.e., displacement vector distribution, displacement vector component distributions, strain tensor component distributions, strain gradient component distributions, strain rate tensor component distributions, strain rate gradient component, acceleration vector component distributions, or velocity vector component distributions. At arbitrary points the values and their graph (time course) can also be displayed. For instance, by utilizing ultrasound diagnosis apparatus, spatial variations of bulk modulus and density of tissues can be displayed in real-time. Thus, the above-described static or motion image, or time course image of the displacement vector distribution, etc. can also be superimposed and displayed on the ultrasound image. The followings can be displayed in vector style as well, i.e., the displacement vector distribution, acceleration vector, velocity vector.

The following is explanation in detail of displacement measurement and calculation processes.

Figure 7:
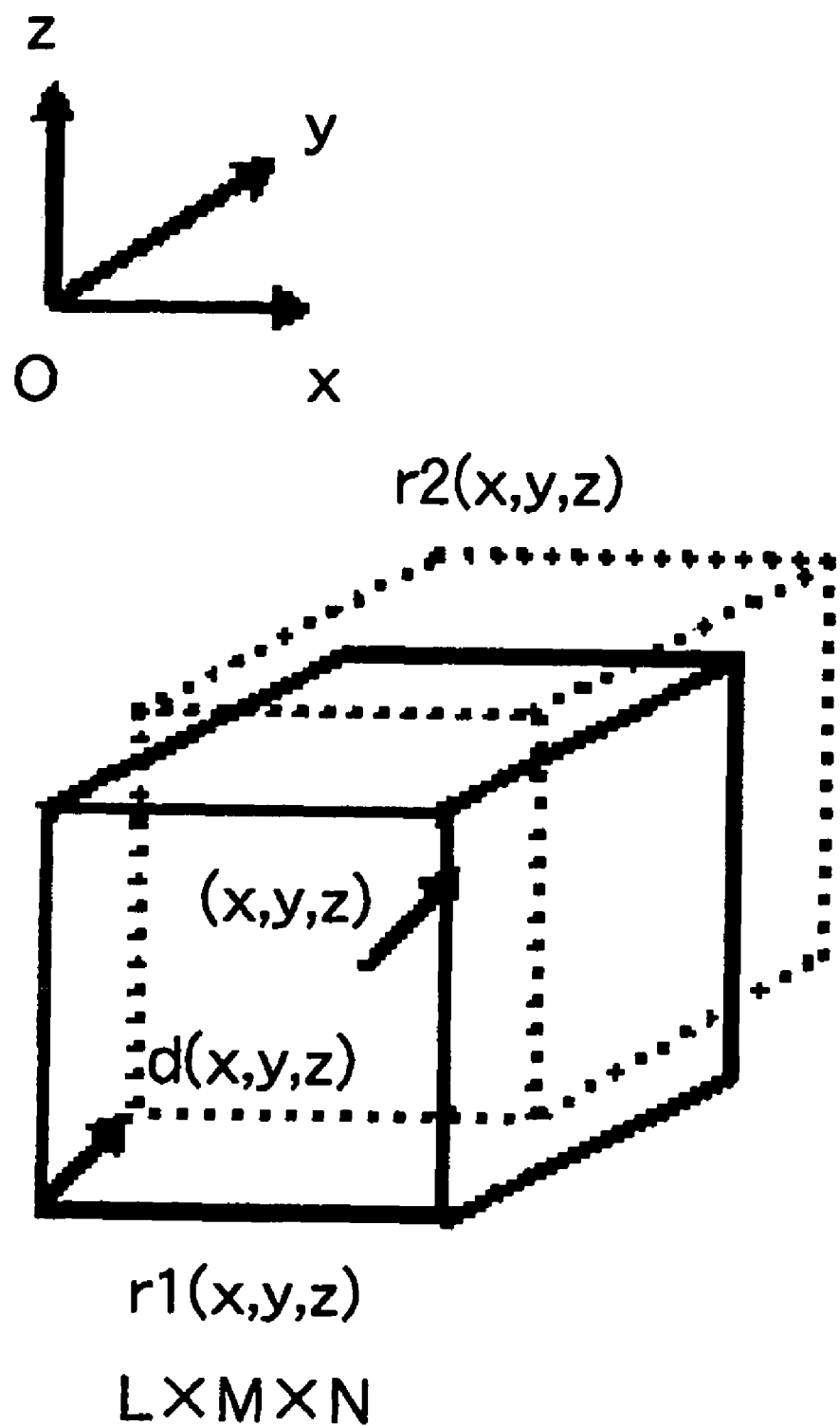
FIG. 7 shows illustration of a local 3D space centered on a point (x,y,z) in 3D ROI in pre-deformation ultrasound echo signal space, and the shifted one in post-deformation ultrasound echo signal space.
Figure 8:
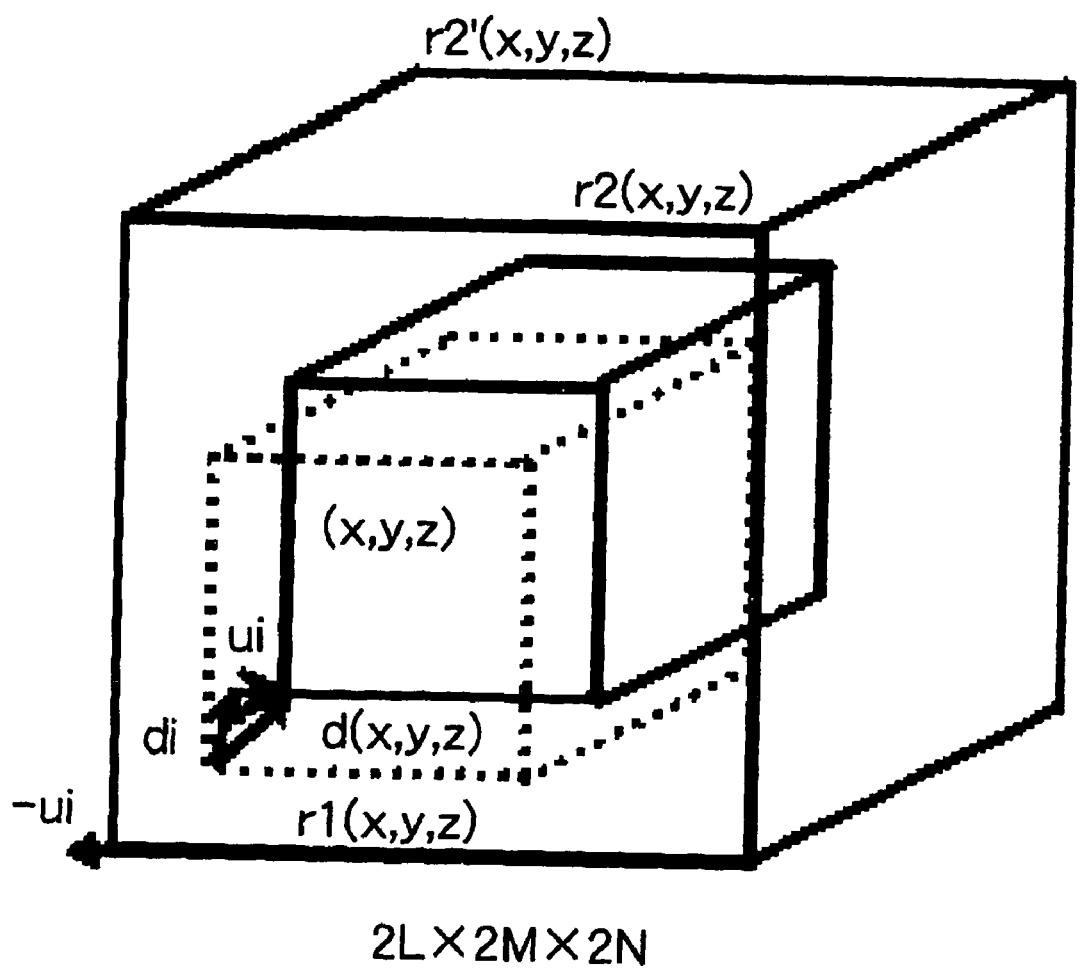
FIG. 8 shows illustration as the example of searching for local 3D ultrasound echo signal by phase matching in searching space set in post-deformation ultrasound echo signal space. That is, the corresponding local signal is searched for using pre-deformation local echo signal.
Figure 9:
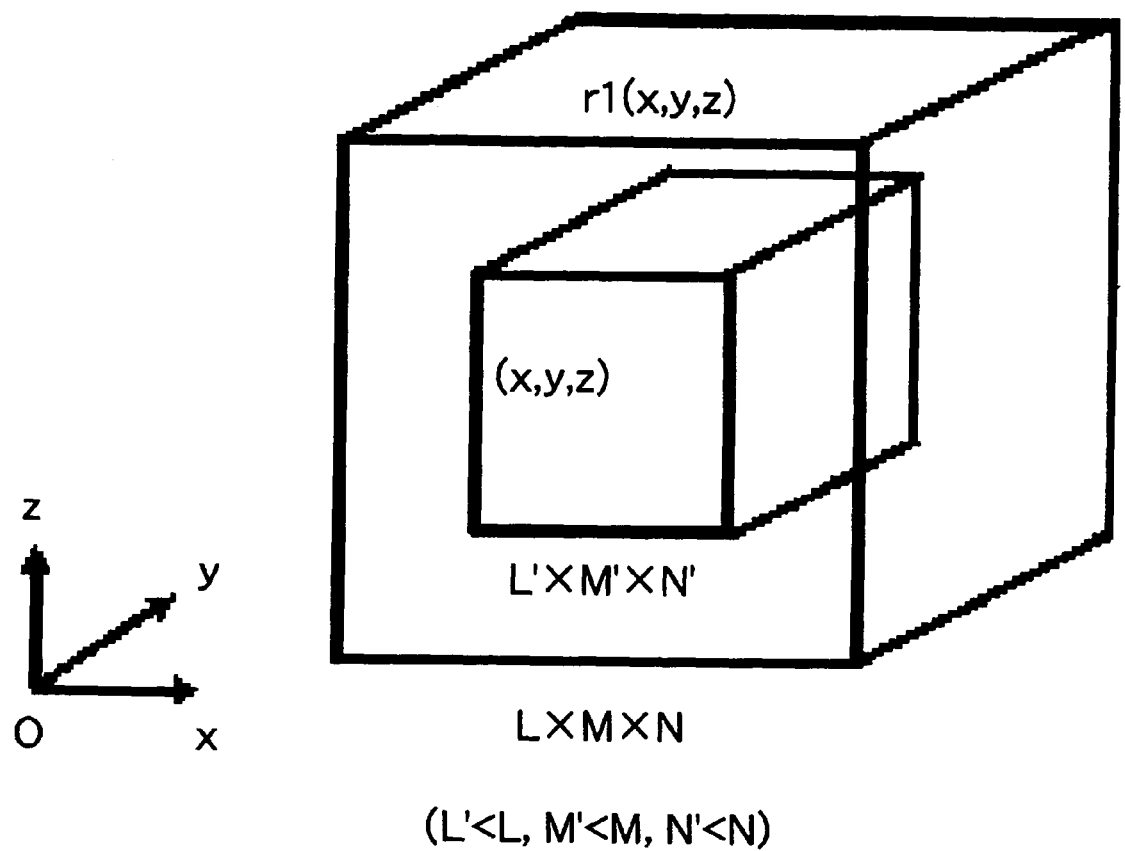
FIG. 9 shows illustration to make 3D displacement vector distribution high spatial resolution, i.e., to make local space small.

(I) Method 1: Measurement of 3D Displacement Vector Distribution 3D displacement vector distribution can be measured in 3D SOI 7 in the Cartesian coordinate system. 3D ultrasound echo signals are acquired under pre-deformation and post-deformation. These echo signals are processed by the below-described methods 1-1, 1-2, 1-3, 1-4, and 1-5. That is, as shown in FIG. 7, local space is set at each point in the pre- and post-deformation 3D echo signal, and as shown in FIG. 8, the corresponding local space is iteratively searched for in the SOI 7 using the local phase characteristics as the index. In this searching scheme, the estimated residual displacement vector is used to update the previously estimated displacement vector. When the estimated residual displacement vector satisfies with prescribed condition, the local space size is made small (FIG. 9). Thus, accurate 3D displacement vector measurement is realized. Here, sampling intervals are $\Delta x$, $\Delta y$, $\Delta z$ respectively in the x, y, and z-axes.

[Method 1-1]

The procedure of the method 1-1 is shown in FIG. 10. The processes from 1 to 5 yields 3D displacement vector $d(x,y,z)$ $[=(dx(x,y,z), dy(x,y,z), dz(x,y,z))^T]$ of arbitrary point $(x,y,z)$ in 3D SOI from pre- and post-deformation local 3D echo signals $r_1(l,m,n)$ and $r_2(l,m,n)$ $[0 \leq l \leq L-1, 0 \leq m \leq M-1, 0 \leq n \leq N-1]$ centered on $(x,y,z)$ of pre- and post-deformation 3D echo signals $r_1(x,y,z)$ and $r_2(x,y,z)$. M, and N should be determined such that $\Delta xL$, $\Delta yM$, $\Delta zN$ are respectively at least 4 times longer than corresponding displacement components $|dx(x,y,z)|$, $|dy(x,y,z)|$, $|dz(x,y,z)|$.

(Process 1: Phase Matching at the Point $(x,y,z)$)

Phase matching is performed to obtain i-th estimate $d^i(x,y,z)$ $[=(d^i x(x,y,z), d^i y(x,y,z), d^i z(x,y,z))^T]$ of the 3D displacement vector $d(x,y,z)$ $[=(dx(x,y,z), dy(x,y,z), dz(x,y,z))^T]$.

Searching space is set in the post-deformation echo signal space $r_2(x,y,z)$, being centered on the local space $[0 \leq l \leq L-1, 0 \leq m \leq M-1, 0 \leq n \leq N-1]$ centered on $(x,y,z)$ and being twice longer than the corresponding length, in order to update the i-1 th estimate $d^{i-1}(x,y,z)$ $[=(d^{i-1}x(x,y,z), d^{i-1}y(x,y,z), d^{i-1}z(x,y,z))^T]$ of the 3D displacement vector $d(x,y,z)$ $[=(dx(x,y,z), dy(x,y,z), dz(x,y,z))^T]$, where $$d^0(x,y,z) = d(x,y,z). \tag{1}$$

The phase of the post-deformation local echo signal is matched to pre-deformation local echo signal by multiplying $$\exp\left\{ j\frac{2\pi}{L}\frac{d_x^{i-1}(x,y,z)}{\Delta x}l + j\frac{2\pi}{M}\frac{d_y^{i-1}(x,y,z)}{\Delta y}m + j\frac{2\pi}{N}\frac{d_z^{i-1}(x,y,z)}{\Delta z}n \right\} \tag{2}$$

to 3D Fourier's transform of this searching space echo signal $r'_2(l,m,n)$ $[0 \leq l \leq 2L-1, 0 \leq m \leq 2M-1, 0 \leq n \leq 2N-1]$ using i-th estimate $d^{i-1}(x,y,z)$, or by multiplying $$\exp\left\{ j\frac{2\pi}{L}\frac{\hat{u}_x^{i-1}(x,y,z)}{\Delta x}l + j\frac{2\pi}{M}\frac{\hat{u}_y^{i-1}(x,y,z)}{\Delta y}m + j\frac{2\pi}{N}\frac{\hat{u}_z^{i-1}(x,y,z)}{\Delta z}n \right\} \tag{2'}$$

to 3D Fourier's transform of the i-1 th phase-matched searching space echo signal $r''^{i-1}_2(l,m,n)$ using the estimate $\hat{u}^{i-1}(x,y,z)$ $[=(\hat{u}_x^{i-1}(x,y,z), \hat{u}_y^{i-1}(x,y,z), \hat{u}_z^{i-1}(x,y,z))^T]$ $[\hat{u}^0(x,y,z)=0$ (zero vector)] of the vector $u^{i-1}(x,y,z)$ $[=(u^{i-1}_x(x,y,z), u^{i-1}_y(x,y,z), u^{i-1}_z(x,y,z))^T]$.

By carrying out inverse Fourier's transform of this product, post-deformation echo signal $r'_2(l,m,n)$ is obtained at the center of the searching space echo signal $r''_2(l,m,n)$, which is used at i-th stage to estimate 3D displacement vector $d(x,y,z)$ $[=(dx(x,y,z), dy(x,y,z), dz(x,y,z))^T]$.

Alternatively, the phase of the pre-deformation local echo signal can be matched to post-deformation local echo signal in a similar way. That is, 3D Fourier's transform of the searching space echo signal $r'_1(l,m,n)$ $[0 \leq l \leq 2L-1, 0 \leq m \leq 2M-1, 0 \leq n \leq 2N-1]$ centered on the point $(x,y,z)$ in the pre-deformation echo signal space is multiplied with $$\exp\left\{ -j\frac{2\pi}{L}\frac{d_x^{i-1}(x,y,z)}{\Delta x}l - j\frac{2\pi}{M}\frac{d_y^{i-1}(x,y,z)}{\Delta y}m - j\frac{2\pi}{N}\frac{d_z^{i-1}(x,y,z)}{\Delta z}n \right\}, \tag{2''}$$

or 3D Fourier's transform of the i-1 th phase-matched searching space echo signal $r''^{i-1}_1(l,m,n)$ is multiplied with $$\exp\left\{-j\frac{2\pi}{L}\frac{\hat{u}_x^{i-1}(x,y,z)}{\Delta x}l - j\frac{2\pi}{M}\frac{\hat{u}_y^{i-1}(x,y,z)}{\Delta y}m - j\frac{2\pi}{N}\frac{\hat{u}_z^{i-1}(x,y,z)}{\Delta z}n\right\}. \quad (2''')$$

(Process 2: Estimation of 3D Residual Displacement Vector at the Point (x,y,z))

Local 3D echo cross-spectrum is evaluated from the 3D Fourier's transforms of the pre-deformation local 3D ultrasound echo signal $r_1(l,m,n)$ and phase-matched post-deformation local 3D ultrasound echo signal $r'_2(l,m,n)$.

$$S^i_{2,1}(l,m,n) = R_2^{i*}(l,m,n)R_1(l,m,n), \quad (3)$$

where * denotes conjugate.

Alternatively, when pre-deformation local 3D ultrasound echo signal is phase-matched, cross-spectrum of $r'_1(l,m,n)$ and $r_2(l,m,n)$ is evaluated as $$S^i_{2,1}(l,m,n) = R_2^*(l,m,n)R'^i_1(l,m,n).$$

Cross-spectrum is represented as $$S^i_{2,1}(l,m,n) \cong |R^i_1(l,m,n)|^2 \exp \quad (4)$$

$$\left\{j\frac{2\pi}{L}\frac{u^i_x(x,y,z)}{\Delta x}l + j\frac{2\pi}{M}\frac{u^i_y(x,y,z)}{\Delta y}m + j\frac{2\pi}{N}\frac{u^i_z(x,y,z)}{\Delta z}n\right\},$$

where $0 \leq l \leq L-1$, $0 \leq m \leq M-1$, $0 \leq n \leq N-1$, and then the phase is represented as $$\theta^i(l,m,n) = \tan^{-1}\left(\frac{\mathrm{Im}[S^i_{2,1}(l,m,n)]}{\mathrm{Re}[S^i_{2,1}(l,m,n)]}\right), \quad (5)$$

where Re[•] and Im[•] respectively represent the real and imaginary component of "•".

The least squares method is implemented on the gradient of the phase eq. (5) weighted with squared cross-spectrum $|S^i_{2,1}(l,m,n)|^2 (=\mathrm{Re}^2[S^i_{2,1}(l,m,n)] + \mathrm{Im}^2[S^i_{2,1}(l,m,n)])$. That is, by minimizing functional $$\mathrm{error}(u^i(x,y,z)) = \quad (6)$$

$$\sum_{l,m,n} |S^i_{2,1}(l,m,n)|^2 \times (\theta^i(l,m,n) - u^i_x(x,y,z)\left(\frac{2\pi}{L\Delta x}\right)l - u^i_y(x,y,z)\left(\frac{2\pi}{M\Delta y}\right)m - u^i_z(x,y,z)\left(\frac{2\pi}{N\Delta z}\right)n)^2$$

with respect to the 3D residual vector $u^i(x,y,z)$ to be used to update the i−1 th estimate $d^{i-1}(x,y,z)$ of the 3D displacement vector $d(x,y,z)$, the estimate of $u^i(x,y,z)$ is obtained as $$\hat{u}(x,y,z)[=(\hat{u}^i_x(x,y,z),\hat{u}^i_y(x,y,z),\hat{u}^i_z(x,y,z))^T]. \quad (6\text{-}2)$$

Concretely, the next simultaneous equations are solved.

$$\begin{bmatrix} \sum_{l,m,n} |S^i_{2,3}(l,m,n)|^2 \left(\frac{2\pi}{L\Delta x}\right) l\theta^i(l,m,n) \\ \sum_{l,m,n} |S^i_{2,1}(l,m,n)|^2 \left(\frac{2\pi}{M\Delta y}\right) m\theta^i(l,m,n) \\ \sum_{l,m,n} |S^i_{2,1}(l,m,n)|^2 \left(\frac{2\pi}{N\Delta z}\right) n\theta^i(l,m,n) \end{bmatrix} = \quad (7)$$

$$\begin{bmatrix} \sum_{l,m,n} |S^i_{2,1}(l,m,n)|^2 \left(\frac{2\pi}{L\Delta x}\right)^2 l^2 & \sum_{l,m,n} |S^i_{2,1}(l,m,n)|^2 \left(\frac{2\pi}{L\Delta x}\right)\left(\frac{2\pi}{M\Delta y}\right) lm & \sum_{l,m,n} |S^i_{2,1}(l,m,n)|^2 \left(\frac{2\pi}{L\Delta x}\right)\left(\frac{2\pi}{N\Delta z}\right) ln \\ \sum_{l,m,n} |S^i_{2,1}(l,m,n)|^2 \left(\frac{2\pi}{L\Delta x}\right)\left(\frac{2\pi}{M\Delta y}\right) lm & \sum_{l,m,n} |S^i_{2,1}(l,m,n)|^2 \left(\frac{2\pi}{M\Delta y}\right)^2 m^2 & \sum_{l,m,n} |S^i_{2,1}(l,m,n)|^2 \left(\frac{2\pi}{M\Delta y}\right)\left(\frac{2\pi}{N\Delta z}\right) mn \\ \sum_{l,m,n} |S^i_{2,1}(l,m,n)|^2 \left(\frac{2\pi}{L\Delta x}\right)\left(\frac{2\pi}{N\Delta z}\right) ln & \sum_{l,m,n} |S^i_{2,1}(l,m,n)|^2 \left(\frac{2\pi}{M\Delta y}\right)\left(\frac{2\pi}{N\Delta z}\right) mn & \sum_{l,m,n} |S^i_{2,1}(l,m,n)|^2 \left(\frac{2\pi}{N\Delta z}\right)^2 n^2 \end{bmatrix} \times \begin{bmatrix} u^i_x(x,y,z) \\ u^i_y(x,y,z) \\ u^i_z(x,y,z) \end{bmatrix}$$

When the 3D displacement vector $d(x,y,z)$ is large, the 3D residual displacement vector $u^i(x,y,z)$ needs to be estimated after unwrapping the phase of the cross-spectrum [eq. (3)] in the frequency domain (l,m,n).

Alternatively, when the 3D displacement vector $d(x,y,z)$ is large, by using cross-correlation method (evaluation of the peak position of the cross-correlation function obtained as 3D inverse Fourier's transform of the cross-spectrum [eq. (3)]) at the initial stages during iterative estimation, the 3D residual displacement vector $u^i(x,y,z)$ can be estimated without unwrapping the phase of the cross-spectrum [eq. (3)] in the frequency domain. Specifically, by using the cross-correlation method, x, y, and z components of the 3D displacement vector are respectively estimated as integer multiplications of the ultrasound echo sampling intervals $\Delta x$, $\Delta y$, $\Delta z$. For instance, with respect to threshold values correTratio or correTdiff, after $$\frac{\|\hat{u}^i(x,y,z)\|}{\|\hat{u}^{i-1}(x,y,z)\|} \leq correTratio \quad (8)$$

or $$\|\hat{u}^i(x,y,z)\| \leq correTdiff \quad (8')$$

is satisfied with where $\|\hat{u}^i(x,y,z)\|$ and $\|\hat{u}^{i-1}(x,y,z)\|$ are respectively norms (magnitudes) of the i th and i−1 th estimate of the residual vectors, by using the estimate of the 3D displacement vector d(x,y,z) as the initial estimate, the 3D residual displacement vector is estimated from the gradient of the phase of the cross-spectrum [eq. (3)].

Empirically it is known that after using cross-correlation method the conditions $|u^i_x(x,y,z)| \leq \Delta x/2$, $|u^i_y(x,y,z)| \leq \Delta y/2$, $|u^i_z(x,y,z)| \leq \Delta z/2$ are satisfied with. However, for allowing estimation of the 3D residual displacement vector without unwrapping the phase of the cross-spectrum, the necessary and sufficient condition is $$\left| \frac{u^i_x(x,y,z)}{\Delta x} + \frac{u^i_y(x,y,z)}{\Delta y} + \frac{u^i_z(x,y,z)}{\Delta z} \right| \leq 1 \tag{9}$$

or $$|u^i_x(x,y,z)| \leq \Delta x/3,\ |u^i_y(x,y,z)| \leq \Delta y/3, \tag{9'}$$
$$\text{and}\ |u^i_z(x,y,z)| \leq \Delta z/3.$$

Therefore, when estimating the gradient of the cross-spectrum phase after using cross-correlation method, the acquired ultrasound echo data are thinned out with constant interval in each direction and the reduced echo data are used such that the condition (9) or (9') is satisfied with. The iteration number i increasing, i.e., the magnitude of the 3D residual displacement vector components $u^i_x(x,y,z)$, $u^i_y(x,y,z)$, $u^i_z(x,y,z)$ decreasing, the ultrasound echo data densities are made restored in each direction. Hence, at initial stages where estimating the gradient of the cross-spectrum phase, for instance, ultrasound echo signals are used with one and half times or twice as a long interval as the original interval in each direction. The densities of the ultrasound echo signals are made restored in each direction, for instance, one and half times or twice per iteration.

Alternatively, when the magnitude of the 3D displacement vector d(x,y,z) is large, at initial stages, the acquired original ultrasound echo data can be thinned out with constant interval in each direction and the reduced echo data can be used such that the 3D residual displacement vector can be estimated without unwrapping the phase of the cross-spectrum [eq. (3)] in the frequency domain (l,m,n). Specifically, the acquired original ultrasound echo data are thinned out with constant interval in each direction and the reduced ehco data are used such that the condition (9) or (9') is satisfied with. The iteration number i increasing, i.e., the magnitude of the 3D residual displacement vector components $u^i_x(x,y,z)$, $u^i_y(x,y,z)$, $u^i_z(x,y,z)$ decreasing, the ultrasound echo data densities are made restored in each direction, for instance, twice per iteration. When the 3D residual displacement vector components $u^i_x(x,y,z)$, $u^i_y(x,y,z)$, $u^i_z(x,y,z)$ are estimated, if neither the condition (9) nor (9') is satisfied with, the values are truncated such that the conditions are satisfied with.

The interval of the ultrasound echo signal data are shortened, for instance, when with respect to threshold values stepTratio or stepTdiff the condition $$\frac{\|\hat{u}^i(x,y,z)\|}{\|\hat{u}^{i-1}(x,y,z)\|} \leq stepTratio \tag{10}$$

or $$\|\hat{u}^i(x,y,z) - \hat{u}^{i-1}(x,y,z)\| \leq stepTdiff \tag{10'}$$

is satisfied with, where $\|\hat{u}^i(x,y,z)\|$ and $\|\hat{u}^{i-1}(x,y,z)\|$ are respectively norms (magnitudes) of the i th and i−1 th estimates of the residual vectors.

The condition (10) or (10') can be applied to each direction component, and in this case the data interval is shorten in each direction. These are also applied to below-described methods 1-2, 1-3, 1-4, and 1-5.

(Process 3: Update of the 3D Displacement Vector Estimate of the Point (x,y,z))

Thus, the i th estimate of the 3D displacement vector d(x, y,z) is evaluated as $$d^i(x,y,z) = d^{i-1}(x,y,z) + \hat{u}^i(x,y,z). \tag{11}$$

[Process 4: Condition for Heightening the Spatial Resolution of the 3D Displacement Vector Distribution Measurement (Condition for Making the Local Space Small)]

In order to make the spatial resolution high of the 3D displacement vector distribution measurement, the local space is made small during iterative estimation. The criteria is below-described. The processes 1, 2 and 3 are iteratively carried out till the criteria is satisfied with. When the criteria is satisfied with, the local space is made small, for instance, the length of each side is made half. For instance, the criteria is (12) or (12') with respect to threshold values Tratio or Tdiff.

$$\frac{\|\hat{u}^i(x,y,z)\|}{\|\hat{u}^{i-1}(x,y,z)\|} \leq Tratio \tag{12}$$

or $$\|\hat{u}^i(x,y,z) - \hat{u}^{i-1}(x,y,z)\| \leq Tdiff, \tag{12'}$$

where $\|\hat{u}^i(x,y,z)\|$ and $\|\hat{u}^{i-1}(x,y,z)\|$ are respectively norms (magnitudes) of the i th and i−1 th estimates of the residual vectors.

The condition (12) or (12') can be applied to each direction component, and in this case the side is shorten in each direction.

(Process 5: Condition for Terminating the Iterative Estimation of the 3D Displacement Vector of the Point (x,y,z))

Below-described is the criteria for terminating the iterative estimation of the 3D displacement vector of each point. The processes 1, 2 and 3 are iteratively carried out till the criteria is satisfied with. For instance, the criteria is (13) or (13') with respect to threshold values aboveTratio or aboveTdiff.

$$\frac{\|\hat{u}^i(x,y,z)\|}{\|\hat{u}^{i-1}(x,y,z)\|} \leq aboveTratio \tag{13}$$

or $$\|\hat{u}^i(x,y,z) - \hat{u}^{i-1}(x,y,z)\| \leq aboveTdiff, \tag{13'}$$

where $\|\hat{u}^i(x,y,z)\|$ and $\|\hat{u}^{i-1}(x,y,z)\|$ are respectively norms (magnitudes) of the i th and i−1 th estimates of the residual vectors.

(Process 6)

The 3D displacement vector component distributions are obtained by carrying out processes 1, 2, 3, 4, and 5 at every point in the 3D SOI.

The initial estimate [eq. (1)] of the iterative estimation of the 3D displacement vector is set as zero vector if a priori data is not given about displacements of body motion nor applied compression. Alternatively, values accurately estimated at neighborhood can be used (high correlation or least squares).

[Limitation of Method 1-1]

The estimate of the 3D displacement vector d(x,y,z) is iteratively updated at each point (x,y,z) in the 3D SOI. Being dependent on the SNR of the local 3D echo signals, particularly at initial stages errors possibly occur when estimating the residual vector and then phase matching possibly diverges. For instance, when solving eq. (7) [process 2] or detecting the peak position of the cross-correlation function [process 2], errors possibly occur.

The possibility for divergence of the phase matching is, for instance, confirmed by the condition (14) or (14') with respect to the threshold value belowTratio or BelowTdiff.

$$\frac{\|\hat{u}^i(x, y, z)\|}{\|\hat{u}^{i-1}(x, y, z)\|} \geq belowTratio \quad (14)$$

or $$\|\hat{u}^i(x, y, z) - \hat{u}^{i-1}(x, y, z)\| \geq belowTdiff, \quad (14')$$

where $\|\hat{u}^i(x,y,z)\|$ and $\|\hat{u}^{i-1}(x,y,z)\|$ are respectively norms (magnitudes) of the i th and i−1 th estimates of the residual vectors.

To prevent phase matching (process 1) from diverging, in the below-described methods 1-2, 1-3, 1-4, and 1-5, by freely using the condition (14) or (14'), estimation error is reduced of the residual vector. Thus, even if the SNR of the ultrasound echo signals are low, accurate 3 D displacement vector measurement can be realized.

[Method 1-2]

The flowchart of the method 1-2 is shown in FIG. 11. To prevent phase matching from diverging at the process 1 of the method 1-1, estimation error is reduced of the residual vector. Thus, even if the SNR of the ultrasound echo signals are low, accurate 3D displacement vector measurement can be realized.

The procedure of iterative estimation is different from that of the method 1-1. At i th estimate (i≧1), the following processes are performed.

(Process 1: Estimation of the 3D Residual Displacement Vector Distribution)

Phase matching and estimation of the 3D residual displacement vector are performed at every point (x,y,z) in the 3D SOI. That is, the processes 1 and 2 of the method 1-1 are performed once at every point in the SOI. Thus, the estimate of the 3D residual vector distribution is obtained [eq. (6-2)].

(Process 2: Update of the Estimate of the 3D Displacement Vector Distribution)

The i−1 th estimate of the 3D displacement vector distribution is updated using i th estimate of the 3D residual vector distribution.

$$d^i(x,y,z) = d^{i-1}(x,y,z) + \hat{u}^i(x,y,z) \quad (15)$$

Next, this estimate is 3D low pass filtered or 3D median filter to yield the estimate of the 3D displacement vector distribution:

$$d^i(x,y,z) = LPF[d^i(x,y,z)], \text{ or } d^i(x,y,z) = MED[d^i(x,y,z)]. \quad (16)$$

Thus, the estimation error is reduced of the residual vector compared with process 2 of the method 1-1 [eq. (7)]. Hence, phase matching of the process 1 of method 1-2 is performed using smoothed estimate of the 3D displacement vector distribution.

[Process 3: Condition for Heightening the Spatial Resolution of the 3D Displacement Vector Distribution Measurement (Condition for Making the Local Space Small)]

In order to make the spatial resolution high of the 3D displacement vector distribution measurement, during iterative estimation, the local space used for each point is made small, or the local space used over the SOI is made small.

The criteria for each point is below-described. The processes 1 and 2 (method 1-2) are iteratively carried out till the criteria is satisfied with. When the criteria is satisfied with, the local space is made small, for instance, the length of each side is made half. For instance, the criteria is (17) or (17') with respect to threshold values Tratio or Tdiff.

$$\frac{\|\hat{u}^i(x, y, z)\|}{\|\hat{u}^{i-1}(x, y, z)\|} \leq Tratio \quad (17)$$

or $$\|\hat{u}^i(x, y, z) - \hat{u}^{i-1}(x, y, z)\| \leq Tdiff, \quad (17')$$

where $\|\hat{u}^i(x,y,z)\|$ and $\|\hat{u}^{i-1}(x,y,z)\|$ are respectively norms (magnitudes) of the i th and i−1 th estimates of the residual vectors.

The condition (17) or (17') can be applied to each direction component, and in this case the side is shorten in each direction.

The criteria over the SOI is below-described. The processes 1 and 2 (method 1-2) are iteratively carried out till the criteria is satisfied with. When the criteria is satisfied with, the local space is made small, for instance, the length of each side is made half. For instance, the criteria is (18) or (18') with respect to threshold values Tratioroi or Tdiffroi.

$$\frac{\sum_{(x,y,z) \in SOI} \|\hat{u}^i(x, y, z)\|^2}{\sum_{(x,y,z) \in SOI} \|\hat{u}^{i-1}(x, y, z)\|^2} \leq Tratioroi \quad (18)$$

or $$\sum_{(x,y,z) \in SOI} \|\hat{u}^i(x, y, z) - \hat{u}^{i-1}(x, y, z)\| \leq Tdiffroi, \quad (18')$$

where $\|\hat{u}^i(x,y,z)\|$ and $\|\hat{u}^{i-1}(x,y,z)\|$ are respectively norms (magnitudes) of the i th and i−1 th estimates of the residual vectors.

The condition (18) or (18') can be applied to each direction component, and in this case the side is shorten in each direction.

(Process 4: Condition for Terminating the Iterative Estimation of the 3D Displacement Vector Distribution)

Below-described is the criteria for terminating the iterative estimation of the 3D displacement vector distribution. The processes 1, 2 and 3 of method 1-2 are iteratively carried out till the criteria is satisfied with. For instance, the criteria is (19) or (19') with respect to threshold values aboveTratioroi or aboveTdiffroi.

$$\frac{\sum_{(x,y,z)\in SOI} \|\hat{u}^i(x,y,z)\|^2}{\sum_{(x,y,z)\in SOI} \|\hat{u}^{i-1}(x,y,z)\|^2} \leq aboveTratioroi \tag{19}$$

or $$\sum_{(x,y,z)\in SOI} \|\hat{u}^i(x,y,z) - \hat{u}^{i-1}(x,y,z)\| \leq aboveTdiffroi, \tag{19'}$$

where $\|\hat{u}^i(x,y,z)\|$ and $\|\hat{u}^{i-1}(x,y,z)\|$ are respectively norms (magnitudes) of the i th and i−1 th estimates of the residual vectors.

Final estimate is obtained from eq. (15) or eq. (16).

The initial estimate [eq. (1)] of the iterative estimation of the 3D displacement vector is set as zero vector if a priori data is not given about displacements of body motion nor applied compression. Alternatively, values accurately estimated at neighborhood can be used (high correlation or least squares).

[Method 1-3]

The flowchart of the method 1-3 is shown in FIG. 12. To prevent phase matching from diverging at the process 1 of the method 1-1, estimation error is reduced of the residual vector. Possibility of divergence is detected from above-described condition (14) or (14'), and by effectively utilizing method 1-1 and 1-2, even if the SNR of the ultrasound echo signals are low, accurate 3D displacement vector measurement can be realized.

At first, the procedure of iterative estimation is same as that of the method 1-2 (Processes 1, 2, 3, and 4). At i th estimate, the following processes are performed.

Phase matching and estimation of the 3D residual displacement vector are performed at every point (x,y,z) in the 3D SOI. That is, the processes 1 and 2 of the method 1-1 are performed once at every point in the SOI. Thus, the estimate of the 3D residual vector distribution is obtained [eq. (6-2)].

During this estimation, if neither condition (14) nor (14') is satisfied with, the method 1-1 is used. If condition (14) or (14') is satisfied with at points or spaces, in the process 2 of the method 1-2, over sufficiently large spaces centered on the points or spaces, or over the SOI, the estimate $d^i(x,y,z)$ of the 3D displacement vector $d(x,y,z)$ can be 3D low pass filtered or 3D median filtered as eq. (20).

$$\hat{d}^i(x,y,z) = LPF[d^i(x,y,z)], \text{ or } \hat{d}^i(x,y,z) = MED[d^i(x,y,z)] \tag{20}$$

Thus, the estimation error is reduced of the residual vector compared with process 2 of the method 1-1 [eq. (7)].

Thus, iterative estimation is terminated at the process 5 of the method 1-1 or the process 4 of the method 1-2. Hence, final estimate is obtained from eq. (11), or eq. (15), or eq. (20).

The initial estimate [eq. (1)] of the iterative estimation of the 3D displacement vector is set as zero vector if a priori data is not given about displacements of body motion nor applied compression. Alternatively, values accurately estimated at neighborhood can be used (high correlation or least squares).

[Method 1-4]

The flowchart of the method 1-4 is shown in FIG. 13. To prevent phase matching from diverging at the process 1 of the method 1-1, estimation error is reduced of the residual vector. Thus, even if the SNR of the ultrasound echo signals are low, accurate 3D displacement vector measurement can be realized.

The procedure of iterative estimation is different from that of the method 1-1. At i th estimate (i≧1), the following processes are performed.

(Process 1: Estimation of the 3D Residual Displacement Vector Distribution)

Phase matching and estimation of the 3D residual displacement vector are performed at every point (x,y,z) in the 3D SOI. That is, the process 1 of the method 1-1 is performed once at every point in the SOI.

To obtain the estimate $\hat{u}^i(x,y,z)$ $[=(\hat{u}_x^i(x,y,z), \hat{u}_y^i(x,y,z), \hat{u}_z^i(x,y,z))^T]$ of the residual vector distribution $u^i(x,y,z)$ $[=(u_x^i(x,y,z), u_y^i(x,y,z), u_z^i(x,y,z))^T]$, at every point local 3D echo cross-spectrum is evaluated from the 3D Fourier's transforms of the pre-deformation local 3D ultrasound echo signal $r_1(l,m,n)$ and phase-matched post-deformation local 3D ultrasound echo signal $r'_2(l,m,n)$. Alternatively, when pre-deformation local 3D ultrasound echo signal is phase-matched, at every point cross-spectrum of $r'_1(l,m,n)$ and $r_2(l,m,n)$ is evaluated.

The least squares method is implemented on the gradient of the phase with utilization of each weight function, i.e., the squared cross-spectrum $|S_{2,1}^i(l,m,n)|^2$, where each weight function is normalized by the power of the cross-spectrum, i.e., $$\sum_{l,m,n} |S_{2,1}^i(l,m,n)|^2.$$

Moreover, regularization method is also implemented. That is, by minimizing the next functional with respect to the vector $u^i$ comprised of the 3D residual vector distribution $u^i(x,y,z)$.

$$error(u^i) = \tag{21}$$
$$\|a - Fu^i\|^2 + \alpha_{1i}\|u^i\|^2 + \alpha_{2i}\|Gu^i\|^2 + \alpha_{3i}\|G^T Gu^i\|^2 + \alpha_{4i}\|GG^T Gu^i\|^2$$

where a: vector comprised of (x,y,z) distribution of the cross-spectrum phase $\Theta^i(l,m,n)$ weighted with cross-spectrum $|S_{2,1}^i(l,m,n)|$ normalized by the magnitude of the cross-spectrum $$\sqrt{\sum_{l,m,n} |S_{2,1}^i(l,m,n)|^2}$$

evaluated at every point in the 3D SOI.

F: matrix comprised of (x,y,z) distribution of the Fourier's coordinate value (l,m,n) weighted with cross-spectrum $|S_{2,1}^i(l,m,n)|$ normalized by the magnitude of the cross-spectrum $$\sqrt{\sum_{l,m,n} |S^i_{2,1}(l,m,n)|^2}$$

evaluated at every point in the 3D SOI.

$\alpha_{1i}, \alpha_{2i}, \alpha_{3i}, \alpha_{4i}$: regularization parameter (at least larger than zero)

$Gu^i$: vector comprised of the finite difference approximations of the 3D distributions of the 3D gradient components of the unknown 3D residual vector $u^i(x,y,z)$ components $$\frac{\partial}{\partial x} u^i_x(x,y,z), \frac{\partial}{\partial y} u^i_x(x,y,z), \frac{\partial}{\partial z} u^i_x(x,y,z),$$

$$\frac{\partial}{\partial x} u^i_y(x,y,z), \frac{\partial}{\partial y} u^i_y(x,y,z), \frac{\partial}{\partial z} u^i_y(x,y,z),$$

$$\frac{\partial}{\partial x} u^i_z(x,y,z), \frac{\partial}{\partial y} u^i_z(x,y,z), \frac{\partial}{\partial z} u^i_z(x,y,z)$$

$G^T Gu^i$: vector comprised of the finite difference approximations of the 3D distributions of the 3D Laplacians of the unknown 3D residual vector $u^i(x,y,z)$ components $$\frac{\partial^2}{\partial x^2} u^i_x(x,y,z) + \frac{\partial^2}{\partial y^2} u^i_x(x,y,z) + \frac{\partial^2}{\partial z^2} u^i_x(x,y,z)$$

$$\frac{\partial^2}{\partial x^2} u^i_y(x,y,z) + \frac{\partial^2}{\partial y^2} u^i_y(x,y,z) + \frac{\partial^2}{\partial z^2} u^i_y(x,y,z)$$

$$\frac{\partial^2}{\partial x^2} u^i_z(x,y,z) + \frac{\partial^2}{\partial y^2} u^i_z(x,y,z) + \frac{\partial^2}{\partial z^2} u^i_z(x,y,z)$$

$GG^T Gu^i$: vector comprised of the finite difference approximations of the 3D distributions of the 3D gradient components of the 3D Laplacians of the unknown 3D residual vector $u^i(x,y,z)$ components $$\frac{\partial}{\partial x}\left(\frac{\partial^2}{\partial x^2} u^i_x(x,y,z) + \frac{\partial^2}{\partial y^2} u^i_x(x,y,z) + \frac{\partial^2}{\partial z^2} u^i_x(x,y,z)\right),$$

$$\frac{\partial}{\partial y}\left(\frac{\partial^2}{\partial x^2} u^i_x(x,y,z) + \frac{\partial^2}{\partial y^2} u^i_x(x,y,z) + \frac{\partial^2}{\partial z^2} u^i_x(x,y,z)\right),$$

$$\frac{\partial}{\partial z}\left(\frac{\partial^2}{\partial x^2} u^i_x(x,y,z) + \frac{\partial^2}{\partial y^2} u^i_x(x,y,z) + \frac{\partial^2}{\partial z^2} u^i_x(x,y,z)\right),$$

$$\frac{\partial}{\partial x}\left(\frac{\partial^2}{\partial x^2} u^i_y(x,y,z) + \frac{\partial^2}{\partial y^2} u^i_y(x,y,z) + \frac{\partial^2}{\partial z^2} u^i_y(x,y,z)\right),$$

$$\frac{\partial}{\partial y}\left(\frac{\partial^2}{\partial x^2} u^i_y(x,y,z) + \frac{\partial^2}{\partial y^2} u^i_y(x,y,z) + \frac{\partial^2}{\partial z^2} u^i_y(x,y,z)\right),$$

$$\frac{\partial}{\partial z}\left(\frac{\partial^2}{\partial x^2} u^i_y(x,y,z) + \frac{\partial^2}{\partial y^2} u^i_y(x,y,z) + \frac{\partial^2}{\partial z^2} u^i_y(x,y,z)\right),$$

$$\frac{\partial}{\partial x}\left(\frac{\partial^2}{\partial x^2} u^i_z(x,y,z) + \frac{\partial^2}{\partial y^2} u^i_z(x,y,z) + \frac{\partial^2}{\partial z^2} u^i_z(x,y,z)\right),$$

$$\frac{\partial}{\partial y}\left(\frac{\partial^2}{\partial x^2} u^i_z(x,y,z) + \frac{\partial^2}{\partial y^2} u^i_z(x,y,z) + \frac{\partial^2}{\partial z^2} u^i_z(x,y,z)\right),$$

$$\frac{\partial}{\partial z}\left(\frac{\partial^2}{\partial x^2} u^i_z(x,y,z) + \frac{\partial^2}{\partial y^2} u^i_z(x,y,z) + \frac{\partial^2}{\partial z^2} u^i_z(x,y,z)\right),$$

As $\|u^i\|^2, \|Gu^i\|^2, \|G^T Gu^i\|^2, \|GG^T Gu^i\|^2$ are positive definite, error($u^i$) has one minimum value. Thus, by solving for residual displacement vector distribution $u^i(x,y,z)$ the simultaneous equations:

$$(F^T F + \alpha_{1i} I + \alpha_{2i} G^T G + \alpha_{3i} G^T GG^T G + \alpha_{4i} G^T GG^T GG^T G) u^i = F^T a, \quad (22)$$

estimate $\hat{u}^i(x,y,z) [=(\hat{u}^i_x(x,y,z), \hat{u}^i_y(x,y,z), \hat{u}^i_z(x,y,z))^T]$ of the residual vector distribution $u^i(x,y,z) [=(u^i_x(x,y,z), u^i_y(x,y,z), u^i_z(x,y,z))^T]$ is stably obtained. Thus, estimation error is reduced of the residual vector.

The regularization parameter of important information is set relatively large. Thus, the regularization parameters depend on the correlation of the local echo data (peak value of the cross-correlation function, sharpness of the cross-correlation function, width of the cross-correlation function), the SNR of the cross-spectrum power, etc.; then position of the unknown displacement vector, direction of the unknown displacement component, direction of the partial derivative, etc.

(Process 2: Update of the Estimate of the 3D Displacement Vector Distribution)

The i−1 th estimate of the 3D displacement vector distribution is updated using i th estimate of the 3D residual vector distribution.

$$d^i(x,y,z) = d^{i-1}(x,y,z) + \hat{u}^i(x,y,z) \quad (23)$$

Freely, this estimate can be 3D low pass filtered or 3D median filter to yield the estimate of the 3D displacement vector distribution.

$$\hat{d}^i(x,y,z) = LPF[d^i(x,y,z)], \text{ or } \hat{d}^i(x,y,z) = MED[d^i(x,y,z)] \quad (24)$$

Hence, phase matching of the process 1 of method 1-4 is performed using the 3D residual vector data $u^i(x,y,z)$ obtained from eq. (22), or the 3D vector data $d^i(x,y,z)$ obtained from eq. (23), or smoothed estimate obtained from eq. (24).

[Process 3: Condition for Heightening the Spatial Resolution of the 3D Displacement Vector Distribution Measurement (Condition for Making the Local Space Small)]

In order to make the spatial resolution high of the 3D displacement vector distribution measurement, during iterative estimation, the local space used for each point is made small, or the local space used over the SOI is made small.

The criteria for each point is below-described. The processes 1 and 2 of method 1-4 are iteratively carried out till the criteria is satisfied with. When the criteria is satisfied with, the local space is made small, for instance, the length of each side is made half. For instance, the criteria is (25) or (25') with respect to threshold values Tratio or Tdiff.

$$\frac{\|\hat{u}^i(x,y,z)\|}{\|\hat{u}^{i-1}(x,y,z)\|} \leq Tratio \quad (25)$$

or $$\|\hat{u}^i(x,y,z) - \hat{u}^{i-1}(x,y,z)\| \leq Tdiff, \quad (25')$$

where $\|\hat{u}^i(x,y,z)\|$ and $\|\hat{u}^{i-1}(x,y,z)\|$ are respectively norms (magnitudes) of the i th and i−1 th estimates of the residual vectors.

The condition (25) or (25') can be applied to each direction component, and in this case the side is shorten in each direction.

The criteria over the SOI is below-described. The processes 1 and 2 of method 1-4 are iteratively carried out till the criteria is satisfied with. When the criteria is satisfied with, the local space is made small, for instance, the length of each side is made half. For instance, the criteria is (26) or (26') with respect to threshold values Tratioroi or Tdiffroi.

$$\frac{\sum_{(x,y,z)\in SOI}\|\hat{u}^i(x,y,z)\|^2}{\sum_{(x,y,z)\in SOI}\|\hat{u}^{i-1}(x,y,z)\|^2} \leq Tratioroi \quad (26)$$

or $$\sum_{(x,y,z)\in SOI}\|\hat{u}^i(x,y,z) - \hat{u}^{i-1}(x,y,z)\| \leq Tdiffroi, \quad (26')$$

where $\|\hat{u}^i(x,y,z)\|$ and $\|\hat{u}^{i-1}(x,y,z)\|$ are respectively norms (magnitudes) of the i th and i−1 th estimates of the residual vectors.

The condition (26) or (26') can be applied to each direction component, and in this case the side is shorten in each direction.

(Process 4: Condition for Terminating the Iterative Estimation of the 3D Displacement Vector Distribution)

Below-described is the criteria for terminating the iterative estimation of the 3D displacement vector distribution. The processes 1, 2 and 3 of method 1-4 are iteratively carried out till the criteria is satisfied with. For instance, the criteria is (27) or (27') with respect to threshold values aboveTratioroi or aboveTdiffroi.

$$\frac{\sum_{(x,y,z)\in SOI}\|\hat{u}^i(x,y,z)\|^2}{\sum_{(x,y,z)\in SOI}\|\hat{u}^{i-1}(x,y,z)\|^2} \leq above\ Tratioroi \quad (27)$$

or $$\sum_{(x,y,z)\in SOI}\|\hat{u}^i(x,y,z) - \hat{u}^{i-1}(x,y,z)\| \leq above\ Tdiffroi, \quad (27')$$

where $\|\hat{u}^i(x,y,z)\|$ and $\|\hat{u}^{i-1}(x,y,z)\|$ are respectively norms (magnitudes) of the i th and i−1 th estimates of the residual vectors.

Final estimate is obtained from eq. (23) or eq. (24).

The initial estimate [eq. (1)] of the iterative estimation of the 3D displacement vector is set as zero vector if a priori data is not given about displacements of body motion nor applied compression. Alternatively, values accurately estimated at neighborhood can be used (high correlation or least squares).

[Method 1-5]

The flowchart of the method 1-5 is shown in FIG. 14. To prevent phase matching from diverging at the process 1 of the method 1-1, estimation error is reduced of the residual vector. Possibility of divergence is detected from above-described condition (14) or (14'), and by effectively utilizing method 1-1 and 1-4, even if the SNR of the ultrasound echo signals are low, accurate 3D displacement vector measurement can be realized.

At first, the procedure of iterative estimation is same as that of the method 1-4 (Processes 1, 2, 3, and 4). At i th estimate, the following processes are performed.

Phase matching and estimation of the 3D residual displacement vector are performed at every point (x,y,z) in the 3D SOI. That is, the process 1 of the method 1-1 is performed once at every point in the SOI. Moreover, using the regularization method, stably the estimate of the 3D residual vector distribution is obtained.

During this estimation, if neither condition (14) nor (14') is satisfied with, the method 1-1 is used. If condition (14) or (14') is satisfied with at points or spaces, in the process 2 of the method 1-4, over sufficiently large spaces centered on the points or spaces, or over the SOI, the estimate $d^i(x,y,z)$ of the 3D displacement vector $d(x,y,z)$ can be 3D low pass filtered or 3D median filtered as eq. (28).

$$d^i(x,y,z) = LPF[d^i(x,y,z)], \text{ or } d^i(x,y,z) = MED[d^i(x,y,z)] \quad (28)$$

Thus, the estimation error is reduced of the residual vector.

Iterative estimation is terminated at the process 5 of the method 1-1 or the process 4 of the method 1-4. Hence, final estimate is obtained from eq. (11), or eq. (23), or eq. (28).

The initial estimate [eq. (1)] of the iterative estimation of the 3D displacement vector is set as zero vector if a priori data is not given about displacements of body motion nor applied compression. Alternatively, values accurately estimated at neighborhood can be used (high correlation or least squares).

Figure 15:
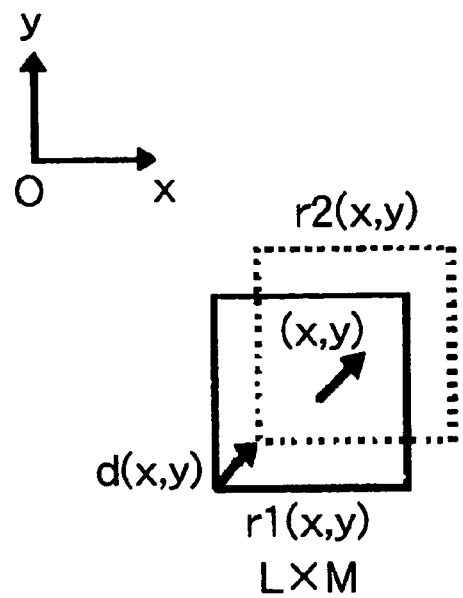
FIG. 15 shows illustration of a local 2D region centered on a point (x,y) in 2D ROI in pre-deformation ultrasound echo signal space, and the shifted one in post-deformation ultrasound echo signal space.
Figure 16:
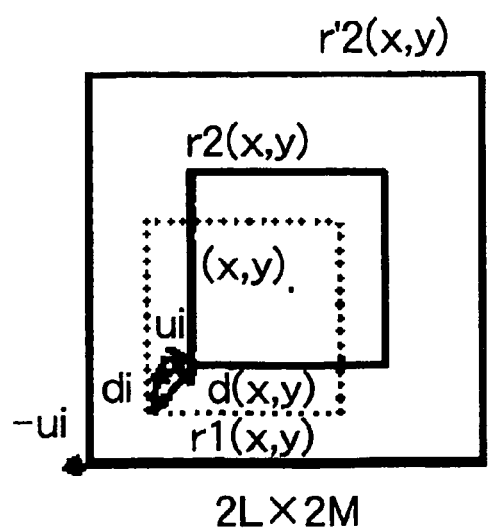
FIG. 16 shows illustration as the example of searching for local 2D ultrasound echo signal by phase matching in searching region set in post-deformation ultrasound echo signal space. That is, the corresponding local signal is searched for using pre-deformation local echo signal.
Figure 17:
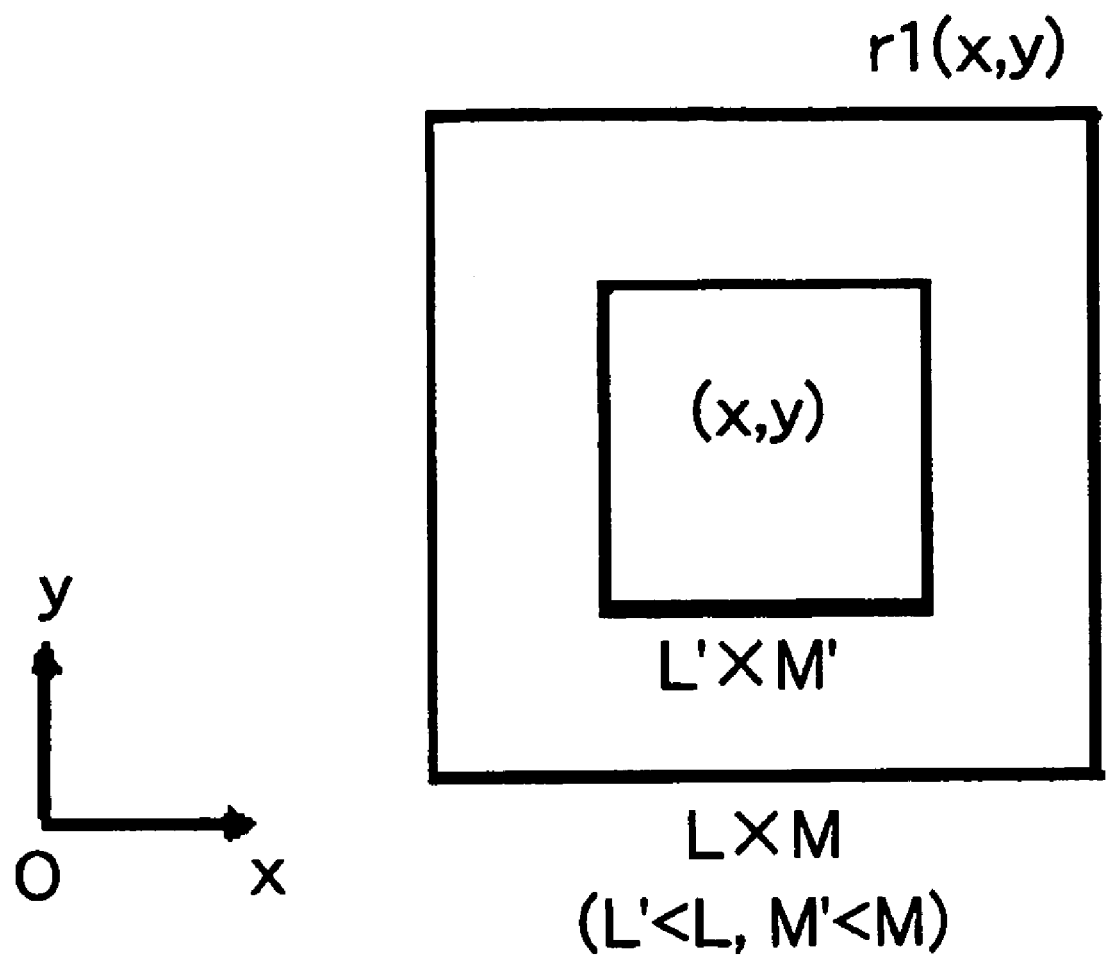
FIG. 17 shows illustration to make 2D displacement vector distribution high spatial resolution, i.e., to make local region small.

(II) Method 2: Measurement of 2D Displacement Vector Component Distribution in 2D ROI 2D displacement vector distribution can be measured in 2D ROI 7 in the Cartesian coordinate system. 2D ultrasound echo signals $r_1(x,y)$ and $r_2(x,y)$ are respectively acquired under pre-deformation and post-deformation. These echo signals are processed by the below-described methods 2-1, 2-2, 2-3, 2-4, and 2-5. That is, as shown in FIG. 15, local region is set at each point in the pre- and post-deformation 2D echo signal, and as shown in FIG. 16, the corresponding local region is iteratively searched for in the ROI 7 using the local phase characteristics as the index. In this searching scheme, the estimated residual displacement vector is used to update the previously estimated displacement vector. When the estimated residual displacement vector satisfies with prescribed condition, the local region size is made small (FIG. 17). Thus, accurate 2D displacement vector measurement is realized. Here, sampling intervals are $\Delta x$ and $\Delta y$ respectively in the x and y-axes.

[Method 2-1]

The procedure of the method 2-1 is shown in FIG. 10. The processes from 1 to 5 yields 2D displacement vector d(x,y) [=$(dx(x,y), dy(x,y))^T$] of arbitrary point (x,y) in 2D ROI from pre- and post-deformation local 2D echo signals $r_1(l,m)$ and $r_2(l,m)$ [$0 \leq l \leq L-1, 0 \leq m \leq M-1$] centered on (x,y) of pre- and post-deformation 2D echo signals $r_1(x,y)$ and $r_2(x,y)$. L and M should be determined such that $\Delta x L$ and $\Delta y M$ are respectively at least 4 times longer than corresponding displacement components $|dx(x,y)|$ and $|dy(x,y)|$.

(Process 1: Phase Matching at the Point (x,y))

Phase matching is performed to obtain i-th estimate $d^i(x,y)$ [=$(d^i x(x,y), d^i y(x,y))^T$] of the 2D displacement vector d(x,y) [=$(dx(x,y), dy(x,y))^T$].

Searching region is set in the post-deformation echo signal space $r_2(x,y)$, being centered on the local region $[0 \leq l \leq L-1, 0 \leq m \leq M-1]$ centered on $(x,y)$ and being twice longer than the corresponding length, in order to update the i−1 th estimate $d^{i-1}(x,y)$ $[=(d^{i-1}x(x,y), d^{i-1}y(x,y))^T]$ of the 2D displacement vector $d(x,y)$ $[=(dx(x,y), dy(x,y))^T]$, where $$d_0(x,y) = \hat{d}(x,y). \tag{29}$$

The phase of the post-deformation local echo signal is matched to pre-deformation local echo signal by multiplying $$\exp\left\{ j\frac{2\pi}{L}\frac{d_x^{i-1}(x,y)}{\Delta x}l + j\frac{2\pi}{M}\frac{d_y^{i-1}(x,y)}{\Delta y}m \right\} \tag{30}$$

to 2D Fourier's transform of this searching region echo signal $r'_2(l,m)$ $[0 \leq l \leq 2L-1, 0 \leq m \leq 2M-1]$ using i-th estimate $d^{i-1}(x,y)$, or by multiplying $$\exp\left\{ j\frac{2\pi}{L}\frac{\hat{u}_x^{i-1}(x,y)}{\Delta x}l + j\frac{2\pi}{M}\frac{\hat{u}_y^{i-1}(x,y)}{\Delta y}m \right\} \tag{30'}$$

to 2D Fourier's transform of the i−1 th phase-matched searching region echo signal $r''^{i-1}_2(l,m)$ using the estimate $\hat{u}^{i-1}(x,y)$ $[=(\hat{u}_x^{i-1}(x,y),\hat{u}_y^{i-1}(x,y))^T]$ $[\hat{u}^0(x,y)=0$ (zero vector)$]$ of the vector $u^{i-1}(x,y)$ $[=(u^{i-1}_x(x,y), u^{i-1}_y(x,y))^T]$.

By carrying out inverse Fourier's transform of this product, post-deformation echo signal $r'_2(l,m)$ is obtained at the center of the searching region echo signal $r''_2(l,m)$, which is used at i-th stage to estimate 2D displacement vector $d(x,y)$ $[=(dx(x,y), dy(x,y))^T]$.

Alternatively, the phase of the pre-deformation local echo signal can be matched to post-deformation local echo signal in a similar way. That is, 2D Fourier's transform of the searching region echo signal $r'_1(l,m)$ $[0 \leq l \leq 2L-1, 0 \leq m \leq 2M-1]$ centered on the point $(x,y)$ in the pre-deformation echo signal region is multiplied with $$\exp\left\{ -j\frac{2\pi}{L}\frac{d_x^{i-1}(x,y)}{\Delta x}l - j\frac{2\pi}{M}\frac{d_y^{i-1}(x,y)}{\Delta y}m \right\}, \tag{30''}$$

or 2D Fourier's transform of the i−1 th phase-matched searching region echo signal $r''^{i-1}_1(l,m)$ is multiplied with $$\exp\left\{ -j\frac{2\pi}{L}\frac{\hat{u}_x^{i-1}(x,y)}{\Delta x}l - j\frac{2\pi}{M}\frac{\hat{u}_y^{i-1}(x,y)}{\Delta y}m \right\}. \tag{30'''}$$

(Process 2: Estimation of 2D Residual Displacement Vector at the Point $(x,y)$)

Local 2D echo cross-spectrum is evaluated from the 2D Fourier's transforms of the pre-deformation local 2D ultrasound echo signal $r_1(l,m)$ and phase-matched post-deformation local 2D ultrasound echo signal $r'_2(l,m)$.

$$S^i_{2,1}(l,m) = R_2^{i*}(l,m)R_1(l,m), \tag{31}$$

where * denotes conjugate.

Alternatively, when pre-deformation local 2D ultrasound echo signal is phase-matched, cross-spectrum of $r'^i_1(l,m)$ and $r_2(l,m)$ is evaluated as $$S^i_{2,1}(l,m) = R_2^*(l,m)R^i_1(l,m).$$

Cross-spectrum is represented as $$S^i_{2,1}(l,m) \cong |R^i_1(l,m)|^2 \tag{32}$$

$$\exp\left\{ j\frac{2\pi}{L}\frac{u^i_x(x,y)}{\Delta x}l + j\frac{2\pi}{M}\frac{u^i_y(x,y)}{\Delta y} \right\},$$

where $0 \leq l \leq L-1$, $0 \leq m \leq M-1$, and then the phase is represented as $$\theta^i(l,m) = \tan^{-1}\left( \frac{\text{Im}[S^i_{2,1}(l,m)]}{\text{Re}[S^i_{2,1}(l,m)]} \right), \tag{33}$$

where Re[•] and Im[•] respectively represent the real and imaginary component of "•".

The least squares method is implemented on the gradient of the phase eq. (33) weighted with squared cross-spectrum $$|S^i_{2,1}(l,m)|^2 (= Re^2[S^i_{2,1}(l,m)] + Im^2[S^i_{2,1}(l,m)]).$$

That is, by minimizing functional:

$$\text{error}(u^i(x,y)) = \sum_{l,m} |S^i_{2,1}(l,m)|^2 \tag{34}$$

$$\left( \theta^i(l,m) - u^i_x(x,y)\left(\frac{2\pi}{L\Delta x}\right)l - u^i_y(x,y)\left(\frac{2\pi}{M\Delta y}\right)m \right)^2$$

with respect to the 2D residual vector $u^i(x,y)$ to be used to update the i−1 th estimate $d^{i-1}(x,y)$ of the 2D displacement vector $d(x,y)$, the estimate of $u^i(x,y)$ is obtained as $$\hat{u}^i(x,y) = (\hat{u}^i_x(x,y), \hat{u}^i_y(x,y))^T.$$

Concretely, the next simultaneous equations are solved.

$$\begin{bmatrix} \sum_{l,m} |S^i_{2,1}(l,m)|^2 \left(\frac{2\pi}{L\Delta x}\right) l\theta^i(l,m) \\ \sum_{l,m} |S^i_{2,1}(l,m)|^2 \left(\frac{2\pi}{M\Delta y}\right) m\theta^i(l,m) \end{bmatrix} = \tag{35}$$

$$\begin{bmatrix} \sum_{l,m} |S^i_{2,1}(l,m)|^2 \left(\frac{2\pi}{L\Delta x}\right)^2 l^2 & \sum_{l,m} |S^i_{2,1}(l,m)|^2 \left(\frac{2\pi}{L\Delta x}\right)\left(\frac{2\pi}{M\Delta y}\right) lm \\ \sum_{l,m} |S^i_{2,1}(l,m)|^2 \left(\frac{2\pi}{L\Delta x}\right)\left(\frac{2\pi}{M\Delta y}\right) lm & \sum_{l,m} |S^i_{2,1}(l,m)|^2 \left(\frac{2\pi}{M\Delta y}\right)^2 m^2 \end{bmatrix}$$

$$\times \begin{bmatrix} u^i_x(x,y) \\ u^i_y(x,y) \end{bmatrix}$$

When the 2D displacement vector d(x,y) is large, the 2D residual displacement vector $u^i(x,y)$ needs to be estimated after unwrapping the phase of the cross-spectrum [eq. (31)] in the frequency domain (l,m).

Alternatively, when the 2D displacement vector d(x,y) is large, by using cross-correlation method (evaluation of the peak position of the cross-correlation function obtained as 2D inverse Fourier's transform of the cross-spectrum [eq. (31)]) at the initial stages during iterative estimation, the 2D residual displacement vector $u^i(x,y)$ can be estimated without unwrapping the phase of the cross-spectrum [eq. (31)] in the frequency domain. Specifically, by using the cross-correlation method, x and y components of the 2D displacement vector are respectively estimated as integer multiplications of the ultrasound echo sampling intervals $\Delta x$, $\Delta y$. For instance, with respect to threshold values correTratio or correTdiff, after $$\frac{\|\hat{u}^i(x, y)\|}{\|\hat{u}^{i-1}(x, y)\|} \leq correTratio \tag{36}$$

or $$\|\hat{u}^i(x, y)\| \leq correTdiff \tag{36'}$$

is satisfied with where $\|\hat{u}^i(x,y)\|$ and $\|\hat{u}^{i-1}(x,y)\|$ re respectively norms (magnitudes) of the i th and i−1 th estimates of the residual vectors, by using the estimate of the 2D displacement vector d(x,y) as the initial estimate, the 2D residual displacement vector is estimated from the gradient of the phase of the cross-spectrum [eq. (31)].

Empirically it is known that after using cross-correlation method the conditions $|u^i_x(x,y)| \leq \Delta x/2$, $|u^i_y(x,y)| \leq \Delta y/2$ are satisfied with. Then, the necessary and sufficient condition for allowing estimation of the 2D residual displacement vector without unwrapping the phase of the cross-spectrum $$\left|\frac{u^i_x(x, y)}{\Delta x} + \frac{u^i_y(x, y)}{\Delta y}\right| \leq 1 \tag{37}$$

is satisfied with.

Alternatively, when the magnitude of the 2D displacement vector d(x,y) is large, at initial stages, the acquired original ultrasound echo data can be thinned out with constant interval in each direction and the reduced echo data can be used such that the 2D residual displacement vector can be estimated without unwrapping the phase of the cross-spectrum [eq. (31)] in the frequency domain (l,m). Specifically, the acquired original ultrasound echo data are thinned out with constant interval in each direction and the reduced ehco data are used such that the condition (37) or (37') is satisfied with.

$$|u_x^i(x,y)| \leq \Delta x/2 \text{ and } |u_y^i(x,y)| \leq \Delta y/2. \tag{37'}$$

The iteration number i increasing, i.e., the magnitude of the 2D residual displacement vector components $u^i_x(x,y)$, $u^i_y(x,y)$ decreasing, the ultrasound echo data densities are made restored in each direction, for instance, twice per iteration.

The interval of the ultrasound echo signal data are shortened, for instance, when with respect to threshold values stepTratio or stepTdiff the condition $$\frac{\|\hat{u}^i(x, y)\|}{\|\hat{u}^{i-1}(x, y)\|} \leq stepTratio \tag{38}$$

or $$\|\hat{u}^i(x, y) - \hat{u}^{i-1}(x, y)\| \leq stepTdiff \tag{38'}$$

is satisfied with, where $\|\hat{u}^i(x,y)\|$ and $\|\hat{u}^{i-1}(x,y)\|$ are respectively norms (magnitudes) of the i th and i−1 th estimates of the residual vectors.

The condition (38) or (38') can be applied to each direction component, and in this case the data interval is shorten in each direction. These are also applied to below-described methods 2-2, 2-3, 2-4, and 2-5.

(Process 3: Update of the 2D Displacement Vector Estimate of the Point (x,y))

Thus, the i th estimate of the 2D displacement vector d(x,y) is evaluated as $$d^i(x,y) = d^{i-1}(x,y) + \hat{u}^i(x,y). \tag{39}$$

[Process 4: Condition for Heightening the Spatial Resolution of the 2D Displacement Vector Distribution Measurement (Condition for Making the Local Region Small)]

In order to make the spatial resolution high of the 2D displacement vector distribution measurement, the local region is made small during iterative estimation. The criteria is below-described. The processes 1, 2 and 3 are iteratively carried out till the criteria is satisfied with. When the criteria is satisfied with, the local region is made small, for instance, the length of each side is made half. For instance, the criteria is (40) or (40') with respect to threshold values $$\frac{\|\hat{u}^i(x, y)\|}{\|\hat{u}^{i-1}(x, y)\|} \leq Tratio \tag{40}$$

or $$\|\hat{u}^i(x, y) - \hat{u}^{i-1}(x, y)\| \leq Tdiff, \tag{40'}$$

where $\|\hat{u}\hat{u}^i(x,y)\|$ and $\|\hat{u}^{i-1}(x,y)\|$ are respectively norms (magnitudes) of the i th and i−1 th estimates of the residual vectors.

The condition (40) or (40') can be applied to each direction component, and in this case the side is shorten in each direction.

(Process 5: Condition for Terminating the Iterative Estimation of the 2D Displacement Vector of the Point (x,y))

Below-described is the criteria for terminating the iterative estimation of the 2D displacement vector of each point. The processes 1, 2 and 3 are iteratively carried out till the criteria is satisfied with. For instance, the criteria is (41) or (41') with respect to threshold values aboveTratio or aboveTdiff.

$$\frac{\|\hat{u}^i(x, y)\|}{\|\hat{u}^{i-1}(x, y)\|} \leq aboveTratio \tag{41}$$

or $$\|\hat{u}^i(x, y) - \hat{u}^{i-1}(x, y)\| \leq aboveTdiff, \tag{41'}$$

where $\|\hat{u}^i(x,y)\|$ and $\|\hat{u}^{i-1}(x,y)\|$ are respectively norms (magnitudes) of the i th and i−1 th estimates of the residual vectors.

(Process 6)

The 2D displacement vector component distributions are obtained by carrying out processes 1, 2, 3, 4, and 5 at every point in the 2D ROI.

The initial estimate [eq. (29)] of the iterative estimation of the 2D displacement vector is set as zero vector if a priori data is not given about displacements of body motion nor applied compression. Alternatively, values accurately estimated at neighborhood can be used (high correlation or least squares).

[Limitation of Method 2-1]

The estimate of the 2D displacement vector d(x,y) is iteratively updated at each point (x,y) in the 2D ROI. Being dependent on the SNR of the local 2D echo signals, particularly at initial stages errors possibly occur when estimating the residual vector and then phase matching possibly diverges. For instance, when solving eq. (35) [process 2] or detecting the peak position of the cross-correlation function [process 2], errors possibly occur.

The possibility for divergence of the phase matching is, for instance, confirmed by the condition (42) or (42') with respect to the threshold value belowTratio or BelowTdiff.

$$\frac{\|\hat{u}^i(x, y)\|}{\|\hat{u}^{i-1}(x, y)\|} \geq belowTratio \tag{42}$$

or $$\|\hat{u}^i(x, y) - \hat{u}^{i-1}(x, y)\| \geq belowTdiff, \tag{42'}$$

where $\|\hat{u}^i(x,y)\|$ and $\|\hat{u}^{i-1}(x,y)\|$ are respectively norms (magnitudes) of the i th and i−1 th estimates of the residual vectors.

To prevent phase matching (process 1) from diverging, in the below-described methods 2-2, 2-3, 2-4, and 2-5, by freely using the condition (42) or (42'), estimation error is reduced of the residual vector. Thus, even if the SNR of the ultrasound echo signals are low, accurate 2D displacement vector measurement can be realized.

[Method 2-2]

The flowchart of the method 2-2 is shown in FIG. 11. To prevent phase matching from diverging at the process 1 of the method 2-1, estimation error is reduced of the residual vector. Thus, even if the SNR of the ultrasound echo signals are low, accurate 2D displacement vector measurement can be realized.

The procedure of iterative estimation is different from that of the method 2-1. At i th estimate (i≧1), the following processes are performed.

(Process 1: Estimation of the 2D Residual Displacement Vector Distribution)

Phase matching and estimation of the 2D residual displacement vector are performed at every point (x,y) in the 2D ROI. That is, the processes 1 and 2 of the method 2-1 are performed once at every point in the ROI. Thus, the estimate of the 2D residual vector distribution is obtained.

(Process 2: Update of the Estimate of the 2D Displacement Vector Distribution)

The i−1 th estimate of the 2D displacement vector distribution is updated using i th estimate of the 2D residual vector distribution.

$$d^i(x,y)=d^{i-1}(x,y)+\hat{u}^i(x,y) \tag{43}$$

Next, this estimate is 2D low pass filtered or 2D median filter to yield the estimate of the 2D displacement vector distribution:

$$d^i(x,y)=LPF[d^i(x,y)], \text{ or } d^i(x,y)=MED[d^i(x,y)]. \tag{44}$$

Thus, the estimation error is reduced of the residual vector compared with process 2 of the method 2-1 [eq. (35)]. Hence, phase matching of the process 1 of method 2-2 is performed using smoothed estimate of the 2D displacement vector distribution.

[Process 3: Condition for Heightening the Spatial Resolution of the 2D Displacement Vector Distribution Measurement (Condition for Making the Local Region Small)]

In order to make the spatial resolution high of the 2D displacement vector distribution measurement, during iterative estimation, the local region used for each point is made small, or the local region used over the ROI is made small.

The criteria for each point is below-described. The processes 1 and 2 (method 2-2) are iteratively carried out till the criteria is satisfied with. When the criteria is satisfied with, the local region is made small, for instance, the length of each side is made half. For instance, the criteria is (45) or (45') with respect to threshold values Tratio or Tdiff.

$$\frac{\|\hat{u}^i(x, y)\|}{\|\hat{u}^{i-1}(x, y)\|} \leq Tratio \tag{45}$$

or $$\|\hat{u}^i(x, y) - \hat{u}^{i-1}(x, y)\| \leq Tdiff, \tag{45'}$$

where $\|\hat{u}^i(x,y)\|$ and $\|\hat{u}^{i-1}(x,y)\|$ are respectively norms (magnitudes) of the i th and i−1 th estimates of the residual vectors.

The condition (45) or (45') can be applied to each direction component, and in this case the side is shorten in each direction.

The criteria over the ROI is below-described. The processes 1 and 2 (method 2-2) are iteratively carried out till the criteria is satisfied with. When the criteria is satisfied with, the local region is made small, for instance, the length of each side is made half. For instance, the criteria is (46) or (46') with respect to threshold values Tratioroi or Tdiffroi.

$$\frac{\sum_{(x,y)\in ROI} \|\hat{u}^i(x, y)\|^2}{\sum_{(x,y)\in ROI} \|\hat{u}^{i-1}(x, y)\|^2} \leq Tratioroi \tag{46}$$

or $$\sum_{(x,y)\in ROI} \|\hat{u}^i(x, y) - \hat{u}^{i-1}(x, y)\| \leq Tdiffroi, \tag{46'}$$

where $\|\hat{u}^i(x,y)\|$ and $\|\hat{u}^{i-1}(x,y)\|$ are respectively norms (magnitudes) of the i th and i−1 th estimates of the residual vectors.

The condition (46) or (46') can be applied to each direction component, and in this case the side is shorten in each direction.

(Process 4: Condition for Terminating the Iterative Estimation of the 2D Displacement Vector Distribution)

Below-described is the criteria for terminating the iterative estimation of the 2D displacement vector distribution. The processes 1, 2 and 3 of method 2-2 are iteratively carried out till the criteria is satisfied with. For instance, the criteria is (47) or (47') with respect to threshold values aboveTratioroi or aboveTdiffroi.

$$\frac{\sum_{(x,y)\in ROI}\|\hat{u}^i(x,y)\|^2}{\sum_{(x,y)\in ROI}\|\hat{u}^{i-1}(x,y)\|^2} \leq aboveTratioroi \quad (47)$$

or $$\sum_{(x,y)\in ROI}\|\hat{u}^i(x,y)-\hat{u}^{i-1}(x,y)\| \leq aboveTdiffroi, \quad (47')$$

where $\|\hat{u}^i(x,y)\|$ and $\|\hat{u}^{i-1}(x,y)\|$ are respectively norms (magnitudes) of the i th and i–1 th estimates of the residual vectors.

Final estimate is obtained from eq. (43) or eq. (44).

The initial estimate [eq. (29)] of the iterative estimation of the 2D displacement vector is set as zero vector if a priori data is not given about displacements of body motion nor applied compression. Alternatively, values accurately estimated at neighborhood can be used (high correlation or least squares).

[Method 2-3]

The flowchart of the method 2-3 is shown in FIG. 12. To prevent phase matching from diverging at the process 1 of the method 2-1, estimation error is reduced of the residual vector. Possibility of divergence is detected from above-described condition (42) or (42'), and by effectively utilizing method 2-1 and 2-2, even if the SNR of the ultrasound echo signals are low, accurate 2D displacement vector measurement can be realized.

At first, the procedure of iterative estimation is same as that of the method 2-2 (Processes 1, 2, 3, and 4). At i th estimate, the following processes are performed.

Phase matching and estimation of the 2D residual displacement vector are performed at every point (x,y) in the 2D ROI. That is, the processes 1 and 2 of the method 2-1 are performed once at every point in the ROI. Thus, the estimate of the 2 D residual vector distribution is obtained.

During this estimation, if neither condition (42) nor (42') is satisfied with, the method 2-1 is used. If condition (42) or (42') is satisfied with at points or regions, in the process 2 of the method 2-2, over sufficiently large regions centered on the points or regions, or over the ROI, the estimate $d^i(x,y)$ of the 2D displacement vector d(x,y) can be 2D low pass filtered or 2D median filtered as eq. (48).

$$\hat{d}^i(x,y)=LPF[d^i(x,y)], \text{ or } \hat{d}^i(x,y)=MED[d^i(x,y)] \quad (48)$$

Thus, the estimation error is reduced of the residual vector compared with process 2 of the method 2-1 [eq. (35)].

Thus, iterative estimation is terminated at the process 5 of the method 2-1 or the process 4 of the method 2-2. Hence, final estimate is obtained from eq. (39), or eq. (43), or eq. (48).

The initial estimate [eq. (29)] of the iterative estimation of the 2D displacement vector is set as zero vector if a priori data is not given about displacements of body motion nor applied compression. Alternatively, values accurately estimated at neighborhood can be used (high correlation or least squares).

[Method 2-4]

The flowchart of the method 2-4 is shown in FIG. 13. To prevent phase matching from diverging at the process 1 of the method 2-1, estimation error is reduced of the residual vector.

Thus, even if the SNR of the ultrasound echo signals are low, accurate 2D displacement vector measurement can be realized.

The procedure of iterative estimation is different from that of the method 2-1. At i th estimate (i≧1), the following processes are performed.

(Process 1: Estimation of the 2D Residual Displacement Vector Distribution)

Phase matching and estimation of the 2D residual displacement vector are performed at every point (x,y) in the 2D ROI. That is, the process 1 of the method 2-1 is performed once at every point in the ROI.

To obtain the estimate $\hat{u}^i(x,y)$ $[=(\hat{u}_x^i(x,y), \hat{u}_y^i(x,y))^T]$ of the residual vector distribution $u^i(x,y)$ $[=(u_x^i(x,y), u_y^i(x,y))^T]$, at every point local 2D echo cross-spectrum is evaluated from the 2D Fourier's transforms of the pre-deformation local 2D ultrasound echo signal $r_1(l,m)$ and phase-matched post-deformation local 2D ultrasound echo signal $r'_2(l,m)$. Alternatively, when pre-deformation local 2D ultrasound echo signal is phase-matched, at every point cross-spectrum of $r'_1(l,m)$ and $r_2(l,m)$ is evaluated.

The least squares method is implemented on the gradient of the phase with utilization of each weight function, i.e., the squared cross-spectrum $|S_{2,1}^i(l,m)|^2$, where each weight function is normalized by the power of the cross-spectrum, i.e., $$\sum_{l,m}|S_{2,1}^i(l,m)|^2.$$

Moreover, regularization method is also implemented. That is, by minimizing the next functional with respect to the vector $u^i$ comprised of the 2D residual vector distribution $u^i(x,y)$.

$$\text{error}(u^i) = \|a-Fu^i\|^2 + \alpha_{1i}\|u^i\|^2 + \alpha_{2i}\|Gu^i\|^2 + \quad (49)$$
$$\alpha_{3i}\|G^TGu^i\|^2 + \alpha_{4i}\|GG^TGu^i\|^2$$

where a: vector comprised of (x,y) distribution of the cross-spectrum phase $\Theta^i(l,m)$ weighted with cross-spectrum $|S_{2,1}^i(l,m)|$ normalized by the magnitude of the cross-spectrum $$\sqrt{\sum_{l,m}|S_{2,1}^i(l,m)|^2}$$

evaluated at every point in the 2D ROI.

F: matrix comprised of (x,y) distribution of the Fourier's coordinate value (l,m) weighted with cross-spectrum $|S_{2,1}^i(l,m)|$ normalized by the magnitude of the cross-spectrum $$\sqrt{\sum_{l,m}|S_{2,1}^i(l,m)|^2}$$

evaluated at every point in the 2D ROI.

$\alpha_{1i}, \alpha_{2i}, \alpha_{3i}, \alpha_{4i}$: regularization parameter (at least larger than zero)

Gu$^i$: vector comprised of the finite difference approximations of the 2D distributions of the 2D gradient components of the unknown 2D residual vector u$^i$(x,y) components $$\frac{\partial}{\partial x}u_x^i(x,y), \frac{\partial}{\partial y}u_x^i(x,y),$$

$$\frac{\partial}{\partial x}u_y^i(x,y), \frac{\partial}{\partial y}u_y^i(x,y)$$

G$^T$Gu$^i$: vector comprised of the finite difference approximations of the 2D distributions of the 2D Laplacians of the unknown 2D residual vector u$^i$(x,y) components $$\frac{\partial^2}{\partial x^2}u_x^i(x,y) + \frac{\partial^2}{\partial y^2}u_x^i(x,y)$$

$$\frac{\partial^2}{\partial x^2}u_y^i(x,y) + \frac{\partial^2}{\partial y^2}u_y^i(x,y)$$

GG$^T$Gu$^i$: vector comprised of the finite difference approximations of the 2D distributions of the 2D gradient components of the 2D Laplacians of the unknown 2D residual vector u$^i$(x,y) components $$\frac{\partial}{\partial x}\left(\frac{\partial^2}{\partial x^2}u_x^i(x,y) + \frac{\partial^2}{\partial y^2}u_x^i(x,y)\right),$$

$$\frac{\partial}{\partial y}\left(\frac{\partial^2}{\partial x^2}u_x^i(x,y) + \frac{\partial^2}{\partial y^2}u_x^i(x,y)\right),$$

$$\frac{\partial}{\partial x}\left(\frac{\partial^2}{\partial x^2}u_y^i(x,y) + \frac{\partial^2}{\partial y^2}u_y^i(x,y)\right),$$

$$\frac{\partial}{\partial y}\left(\frac{\partial^2}{\partial x^2}u_y^i(x,y) + \frac{\partial^2}{\partial y^2}u_y^i(x,y)\right)$$

As $\|u^i\|^2$, $\|Gu^i\|^2$, $\|G^TGu^i\|^2$, $\|GG^TGu^i\|^2$ are positive definite, error(u$^i$) has one minimum value. Thus, by solving for residual displacement vector distribution u$^i$(x,y) the simultaneous equations:

$$(F^TF + \alpha_{1i}I + \alpha_{2i}G^TG + \alpha_{3i}G^TGG^TG + \alpha_{4i}G^TGG^TGG^TG)u^i = F^Ta, \quad (50)$$

estimate û$^i$(x,y) [=(û$_x^i$(x,y), û$_y^i$(x,y))$^T$] of the residual vector distribution u$^i$(x,y) [=(u$_x^i$(x,y), u$_y^i$(x,y))$^T$] is stably obtained. Thus, estimation error is reduced of the residual vector.

The regularization parameter of important information is set relatively large. Thus, the regularization parameters depend on the correlation of the local echo data (peak value of the cross-correlation function, sharpness of the cross-correlation function, width of the cross-correlation function), the SNR of the cross-spectrum power, etc.; then position of the unknown displacement vector, direction of the unknown displacement component, direction of the partial derivative, etc.

(Process 2: Update of the Estimate of the 2D Displacement Vector Distribution)

The i−1 th estimate of the 2D displacement vector distribution is updated using i th estimate of the 2D residual vector distribution.

$$d^i(x,y) = d^{i-1}(x,y) + \hat{u}^i(x,y) \quad (51)$$

Freely, this estimate can be 2D low pass filtered or 2D median filter to yield the estimate of the 2D displacement vector distribution.

$$d^i(x,y) = LPF[d^i(x,y)], \text{ or } d^i(x,y) = MED[d^i(x,y)] \quad (52)$$

Hence, phase matching of the process 1 of method 2-4 is performed using the 2D residual vector data u$^i$(x,y) obtained from eq. (50), or the 2D vector data d$^i$(x,y) obtained from eq. (51), or smoothed estimate obtained from eq. (52).

[Process 3: Condition for Heightening the Spatial Resolution of the 2D Displacement Vector Distribution Measurement (Condition for Making the Local Region Small)]

In order to make the spatial resolution high of the 2D displacement vector distribution measurement, during iterative estimation, the local region used for each point is made small, or the local region used over the ROI is made small.

The criteria for each point is below-described. The processes 1 and 2 of method 2-4 are iteratively carried out till the criteria is satisfied with. When the criteria is satisfied with, the local region is made small, for instance, the length of each side is made half. For instance, the criteria is (25) or (25') with respect to threshold values Tratio or Tdiff.

$$\frac{\|\hat{u}^i(x,y)\|}{\|\hat{u}^{i-1}(x,y)\|} \leq Tratio \quad (53)$$

or $$\|\hat{u}^i(x,y) - \hat{u}^{i-1}(x,y)\| \leq Tdiff, \quad (53')$$

where $\|\hat{u}^i(x,y)\|$ and $\|\hat{u}^{i-1}(x,y)\|$ are respectively norms (magnitudes) of the i th and i−1 th estimates of the residual vectors.

The condition (53) or (53') can be applied to each direction component, and in this case the side is shorten in each direction.

The criteria over the ROI is below-described. The processes 1 and 2 of method 2-4 are iteratively carried out till the criteria is satisfied with. When the criteria is satisfied with, the local region is made small, for instance, the length of each side is made half. For instance, the criteria is (54) or (54') with respect to threshold values Tratioroi or Tdiffroi.

$$\frac{\sum_{(x,y)\in ROI}\|\hat{u}^i(x,y)\|^2}{\sum_{(x,y)\in ROI}\|\hat{u}^{i-1}(x,y)\|^2} \leq Tratioroi \quad (54)$$

or $$\sum_{(x,y)\in ROI}\|\hat{u}^i(x,y) - \hat{u}^{i-1}(x,y)\| \leq Tdiffroi, \quad (54')$$

where $\|\hat{u}^i(x,y)\|$ and $\|\hat{u}^{i-1}(x,y)\|$ are respectively norms (magnitudes) of the i th and i−1 th estimates of the residual vectors.

The condition (54) or (54') can be applied to each direction component, and in this case the side is shorten in each direction.

(Process 4: Condition for Terminating the Iterative Estimation of the 2D Displacement Vector Distribution)

Below-described is the criteria for terminating the iterative estimation of the 2D displacement vector distribution. The processes 1, 2 and 3 of method 2-4 are iteratively carried out till the criteria is satisfied with. For instance, the criteria is (55) or (55') with respect to threshold values aboveTratioroi or aboveTdiffroi.

$$\frac{\sum_{(x,y)\in ROI}\|\hat{u}^i(x,y)\|^2}{\sum_{(x,y)\in ROI}\|\hat{u}^{i-1}(x,y)\|^2} \leq aboveTratioroi \quad (55)$$

or $$\sum_{(x,y)\in ROI}\|\hat{u}^i(x,y)-\hat{u}^{i-1}(x,y)\| \leq aboveTdiffroi, \quad (55')$$

where $\|\hat{u}^i(x,y)\|$ and $\|\hat{u}^{i-1}(x,y)\|$ are respectively norms (magnitudes) of the i th and i−1 th estimates of the residual vectors.

Final estimate is obtained from eq. (51) or eq. (52).

The initial estimate [eq. (29)] of the iterative estimation of the 2D displacement vector is set as zero vector if a priori data is not given about displacements of body motion nor applied compression. Alternatively, values accurately estimated at neighborhood can be used (high correlation or least squares).

[Method 2-5]

The flowchart of the method 2-5 is shown in FIG. 14. To prevent phase matching from diverging at the process 1 of the method 2-1, estimation error is reduced of the residual vector. Possibility of divergence is detected from above-described condition (42) or (42'), and by effectively utilizing method 2-1 and 2-4, even if the SNR of the ultrasound echo signals are low, accurate 2D displacement vector measurement can be realized.

At first, the procedure of iterative estimation is same as that of the method 2-4 (Processes 1, 2, 3, and 4). At i th estimate, the following processes are performed.

Phase matching and estimation of the 2D residual displacement vector are performed at every point (x,y) in the 2D ROI. That is, the process 1 of the method 2-1 is performed once at every point in the ROI. Moreover, using the regularization method, stably the estimate of the 2D residual vector distribution is obtained.

i−1 th estimate $\hat{d}^{i-1}(x,y)$ of 2D displacement vector distribution d(x,y).

i th estimate $\hat{u}^i(x,y)$ of 2D residual vector distribution $u^i(x,y)$.

During this estimation, if neither condition (42) nor (42') is satisfied with, the method 2-1 is used. If condition (42) or (42') is satisfied with at points or regions, in the process 2 of the method 2-4, over sufficiently large regions centered on the points or regions, or over the ROI, the estimate $d^i(x,y)$ of the 2D displacement vector d(x,y) can be 2D low pass filtered or 2D median filtered as eq. (56).

$$\hat{d}(x,y)=LPF[d^i(x,y)], \text{ or } \hat{d}^i(x,y)=MED[d^i(x,y)] \quad (56)$$

Thus, the estimation error is reduced of the residual vector.

Iterative estimation is terminated at the process 5 of the method 2-1 or the process 4 of the method 2-4. Hence, final estimate is obtained from eq. (39), or eq. (51), or eq. (56).

The initial estimate [eq. (29)] of the iterative estimation of the 2D displacement vector is set as zero vector if a priori data is not given about displacements of body motion nor applied compression. Alternatively, values accurately estimated at neighborhood can be used (high correlation or least squares).

Figure 18:
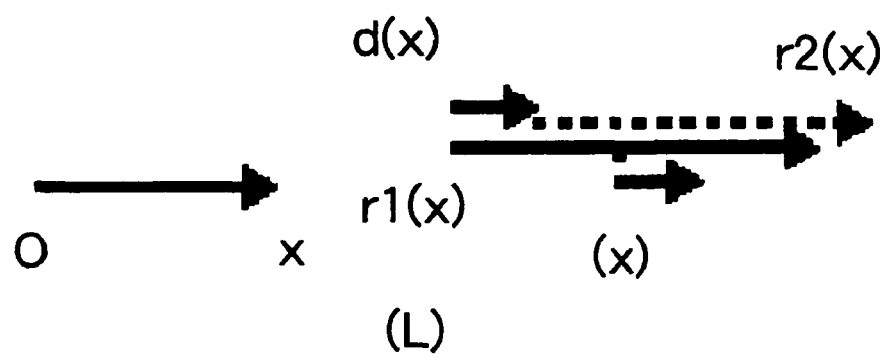
FIG. 18 shows illustration of a local 1D region centered on a point (x) in 1D ROI in pre-deformation ultrasound echo signal space, and the shifted one in post-deformation ultrasound echo signal space.
Figure 19:
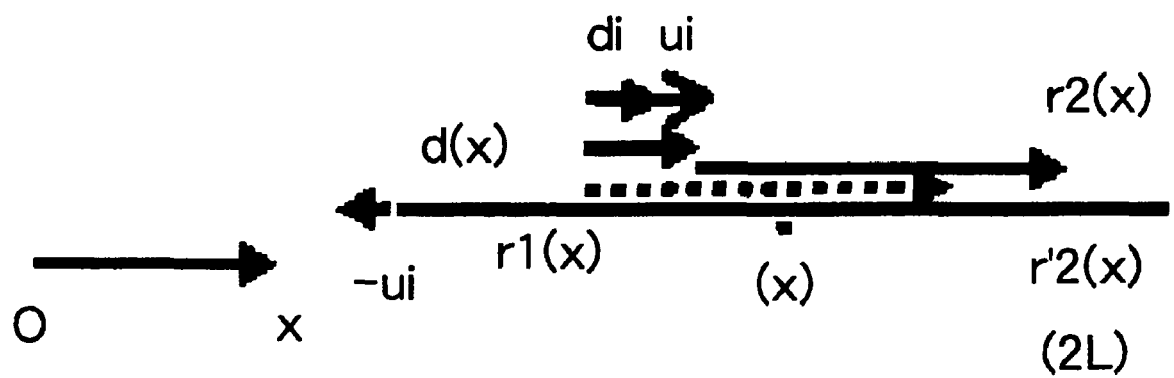
FIG. 19 shows illustration as the example of searching for local 1D ultrasound echo signal by phase matching in searching region set in post-deformation ultrasound echo signal space. That is, the corresponding local signal is searched for using pre-deformation local echo signal.
Figure 20:
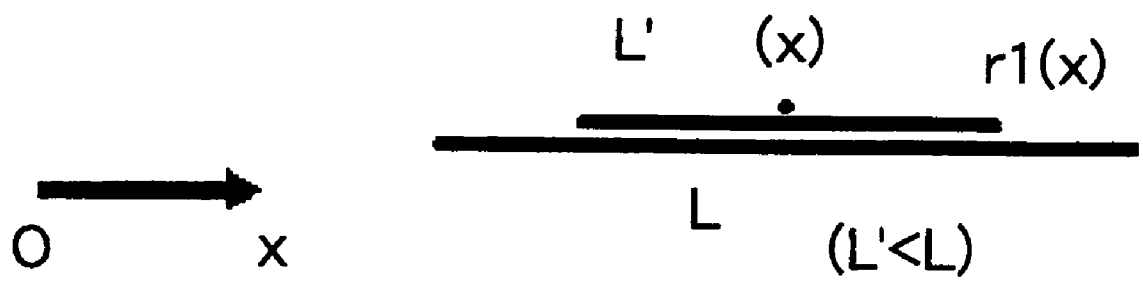
FIG. 20 shows illustration to make one direction displacement component distribution high spatial resolution, i.e., to make local region small.

(III) Method 3: Measurement of 1D (One Direction) Displacement Component Distribution in 1D ROI 1D displacement component distribution can be measured in 1D ROI 7 in the Cartesian coordinate system. 1D ultrasound echo signals $r_1(x)$ and $r_2(x)$ are respectively acquired under pre-deformation and post-deformation. These echo signals are processed by the below-described methods 3-1, 3-2, 3-3, 3-4, and 3-5. That is, as shown in FIG. 18, local region is set at each point in the pre- and post-deformation 1D echo signal, and as shown in FIG. 19, the corresponding local region is iteratively searched for in the ROI 7 using the local phase characteristics as the index. In this searching scheme, the estimated residual displacement component is used to update the previously estimated displacement component. When the estimated residual displacement component satisfies with prescribed condition, the local region size is made small (FIG. 20). Thus, accurate 1D displacement component measurement is realized. Here, sampling interval is Δx in the x-axis.

[Method 3-1]

The procedure of the method 3-1 is shown in FIG. 10. The processes from 1 to 5 yields 1D displacement component dx(x) of arbitrary point x in 1D ROI from pre- and post-deformation local 1D echo signals $r_1(l)$ and $r_2(l)$ [0≦l≦L−1] centered on x of pre- and post-deformation 1D echo signals $r_1(x)$ and $r_2(x)$. L should be determined such that ΔxL is at least 4 times longer than the displacement component |dx(x)|.

(Process 1: Phase Matching at the Point x)

Phase matching is performed to obtain i-th estimate $d^i x(x)$ of the 1D displacement component dx(x).

Searching region is set in the post-deformation echo signal space $r_2(x)$, being centered on the local region [0≦l≦L−1] centered on x and being twice longer than the local region length, in order to update the i−1 th estimate $d^{i-1}x(x)$ of the 1D displacement component dx(x), where $$dx^0(x)=\hat{u}x(x). \quad (57)$$

The phase of the post-deformation local echo signal is matched to pre-deformation local echo signal by multiplying $$\exp\left\{j\frac{2\pi}{L}\frac{d_x^{i-1}(x)}{\Delta x}l\right\} \quad (58)$$

to 1D Fourier's transform of this searching region echo signal $r'_2(l)$ [0≦l≦2L−1] using i-th estimate $dx^{i-1}(x)$, or by multiplying $$\exp\left\{j\frac{2\pi}{L}\frac{\hat{u}_x^{i-1}(x)}{\Delta x}l\right\} \quad (58')$$

to 1D Fourier's transform of the i−1 th phase-matched searching region echo signal $r'^{i-1}_2(l)$ using the estimate $\hat{u}_x^{i-1}(x)$ [$\hat{u}_x^0(x)$=0 (zero)] of the component $u^{i-1}_x(x)$.

By carrying out inverse Fourier's transform of this product, post-deformation echo signal $r^i_2(l)$ is obtained at the center of the searching region echo signal $r'^i_2(l)$, which is used at i-th stage to estimate 1D displacement component dx(x).

Alternatively, the phase of the pre-deformation local echo signal can be matched to post-deformation local echo signal in a similar way. That is, 1D Fourier's transform of the searching region echo signal $r'_1(l)$ [$0 \leq l \leq 2L-1$] centered on the point x in the pre-deformation echo signal region is multiplied with $$\exp\left\{-j\frac{2\pi}{L}\frac{d_x^{i-1}(x)}{\Delta x}l\right\}, \tag{58''}$$

or 1D Fourier's transform of the i−1 th phase-matched searching region echo signal $r'^{i-1}_1(l)$ is multiplied with $$\exp\left\{-j\frac{2\pi}{L}\frac{\hat{u}_x^{i-1}(x)}{\Delta x}l\right\}. \tag{58'''}$$

(Process 2: Estimation of 1D Residual Displacement Component at the Point x)

Local 1D echo cross-spectrum is evaluated from the 1D Fourier's transforms of the pre-deformation local 1D ultrasound echo signal $r_1(l)$ and phase-matched post-deformation local 1D ultrasound echo signal $r'_2(l)$.

$$S^i_{2,1}(l) = R_2^{i*}(l)R_1(l), \tag{59}$$

where * denotes conjugate.

Alternatively, when pre-deformation local 1D ultrasound echo signal is phase-matched, cross-spectrum of $r'_1(l)$ and $r_2(l)$ is evaluated as $$S^i_{2,1}(l) = R_2^*(l)R^i_1(l).$$

Cross-spectrum is represented as $$S^i_{2,1}(l) \cong |R^i_1(l)|^2 \exp\left\{j\frac{2\pi}{L}\frac{u^i_x(x)}{\Delta x}l\right\}, \tag{60}$$

where $0 \leq l \leq L-1$, and then the phase is represented as $$\theta^i(l) = \tan^{-1}\left(\frac{\text{Im}[S^i_{2,1}(l)]}{\text{Re}[S^i_{2,1}(l)]}\right), \tag{61}$$

where Re[•] and Im[•] respectively represent the real and imaginary component of "•".

The least squares method is implemented on the gradient of the phase eq. (61) weighted with squared cross-spectrum $|S_{2,1}^i(l)|^2 (= \text{Re}^2[S_{2,1}^i(l)] + \text{Im}^2[S_{2,1}^i(l)])$. That is, by minimizing functional:

$$\text{error}(u^i_x(x)) = \sum_l |S^i_{2,1}(l)|^2\left(\theta^i(l) - u^i_x(x)\left(\frac{2\pi}{L\Delta x}\right)l\right)^2 \tag{62}$$

with respect to the 1D residual component $u_x^i(x)$ to be used to update the i−1 th estimate $d_x^{i-1}(x)$ of the 1D displacement component dx(x), the estimate of $u_x^i(x)$ is obtained as $\hat{u}_x^i(x)$. Concretely, the next equation is solved.

$$\sum_l |S^i_{2,1}(l)|^2\left(\frac{2\pi}{L\Delta x}\right)l\theta^i(l) = \sum_l |S^i_{2,1}(l)|^2\left(\frac{2\pi}{L\Delta x}\right)^2 l^2 u^i_x(x) \tag{63}$$

When the 1D displacement component dx(x) is large, the 1D residual displacement component $u_x^i(x)$ needs to be estimated after unwrapping the phase of the cross-spectrum [eq. (59)] in the frequency domain l.

Alternatively, when the 1D displacement component dx(x) is large, by using cross-correlation method (evaluation of the peak position of the cross-correlation function obtained as 1D inverse Fourier's transform of the cross-spectrum [eq. (59)]) at the initial stages during iterative estimation, the 1D residual displacement component $u_x^i(x)$ can be estimated without unwrapping the phase of the cross-spectrum [eq. (59)] in the frequency domain. Specifically, by using the cross-correlation method, x component of the 1D displacement component is estimated as integer multiplication of the ultrasound echo sampling interval Δx. For instance, with respect to threshold values correTratio or correTdiff, after $$\frac{\|\hat{u}_x^i(x)\|}{\|\hat{u}_x^{i-1}(x)\|} \leq correTratio \tag{64}$$

or $$\|\hat{u}_x^i(x)\| \leq correTdiff \tag{64'}$$

is satisfied with where $\|\hat{u}_x^i(x)\|$ and $\|\hat{u}^{i-1}(x)\|$ are respectively norms (magnitudes) of the i th and i−1 th estimates of the residual components, by using the estimate of the 1D displacement component dx(x) as the initial estimate, the 1D residual displacement component is estimated from the gradient of the phase of the cross-spectrum [eq. (59)].

Empirically it is known that after using cross-correlation method the condition $|u_x^i(x)| \leq \Delta x/2$ is satisfied with. Then, the necessary and sufficient condition for allowing estimation of the 1D residual displacement component without unwrapping the phase of the cross-spectrum $$\left|\frac{u_x^i(x)}{\Delta x}\right| \leq 1 \tag{65}$$

is satisfied with.

Alternatively, when the magnitude of the 1D displacement component dx(x) is large, at initial stages, the acquired original ultrasound echo data can be thinned out with constant interval in the direction and the reduced echo data can be used such that the 1D residual displacement component can be estimated without unwrapping the phase of the cross-spectrum [eq. (59)] in the frequency domain l. Specifically, the acquired original ultrasound echo data are thinned out with constant interval in the direction and the reduced ehco data are used such that the condition (65) or (65') is satisfied with.

$$|u_x^i(x)| \leq \Delta x/2 \tag{65'}$$

The iteration number i increasing, i.e., the magnitude of the 1D residual displacement component $u_x^i(x)$ decreasing, the ultrasound echo data density is made restored in the direction, for instance, twice per iteration.

The interval of the ultrasound echo signal data are shortened, for instance, when with respect to threshold values stepTratio or stepTdiff the condition $$\frac{\|\hat{u}_x^i(x)\|}{\|\hat{u}_x^{i-1}(x)\|} \leq stepTratio \quad (66)$$

or $$\|\hat{u}_x^i(x) - \hat{u}_x^{i-1}(x)\| \leq stepTdiff \quad (66')$$

is satisfied with, where $\|\hat{u}_x^i(x)\|$ and $\|\hat{u}_x^{i-1}(x)\|$ are respectively norms (magnitudes) of the i th and i−1 th estimates of the residual components.

(Process 3: Update of the 1D Displacement Component Estimate of the Point x)

Thus, the i th estimate of the 1D displacement component dx(x) is evaluated as $$dx^i(x) = dx^{i-1}(x) + \hat{u}_x^i(x). \quad (67)$$

[Process 4: Condition for Heightening the Spatial Resolution of the 1D Displacement Component Distribution Measurement (Condition for Making the Local Region Small)]

In order to make the spatial resolution high of the 1D displacement component distribution measurement, the local region is made small during iterative estimation. The criteria is below-described. The processes 1, 2 and 3 are iteratively carried out till the criteria is satisfied with. When the criteria is satisfied with, the local region is made small, for instance, the length of the local region is made half. For instance, the criteria is (68) or (68') with respect to threshold values Tratio or Tdiff.

$$\frac{\|\hat{u}_x^i(x)\|}{\|\hat{u}_x^{i-1}(x)\|} \leq Tratio \quad (68)$$

or $$\|\hat{u}_x^i(x) - \hat{u}_x^{i-1}(x)\| \leq Tdiff, \quad (68')$$

where $\|\hat{u}_x^i(x)\|$ and $\|\hat{u}_x^{i-1}(x)\|$ are respectively norms (magnitudes) of the i th and i−1 th estimates of the residual components.

(Process 5: Condition for Terminating the Iterative Estimation of the 1D Displacement Component of the Point x)

Below-described is the criteria for terminating the iterative estimation of the 1D displacement component of each point. The processes 1, 2 and 3 are iteratively carried out till the criteria is satisfied with. For instance, the criteria is (69) or (69') with respect to threshold values aboveTratio or aboveTdiff.

$$\frac{\|\hat{u}_x^i(x)\|}{\|\hat{u}_x^{i-1}(x)\|} \leq aboveTratio \quad (69)$$

or $$\|\hat{u}_x^i(x) - \hat{u}_x^{i-1}(x)\| \leq aboveTdiff, \quad (69')$$

where $\|\hat{u}^i(x)\|$ and $\|\hat{u}_x^{i-1}(x)\|$ are respectively norms (magnitudes) of the i th and i−1 th estimates of the residual components.

(Process 6)

The 1D displacement component distribution is obtained by carrying out processes 1, 2, 3, 4, and 5 at every point in the 1D ROI.

The initial estimate [eq. (57)] of the iterative estimation of the 1D displacement component is set as zero if a priori data is not given about displacements of body motion nor applied compression. Alternatively, values accurately estimated at neighborhood can be used (high correlation or least squares).

[Limitation of Method 3-1]

The estimate of the 1D displacement component dx(x) is iteratively updated at each point x in the 1D ROI. Being dependent on the SNR of the local 1D echo signals, particularly at initial stages errors possibly occur when estimating the residual component and then phase matching possibly diverges. For instance, when solving eq. (63) [process 2] or detecting the peak position of the cross-correlation function [process 2], errors possibly occur.

The possibility for divergence of the phase matching is, for instance, confirmed by the condition (70) or (70') with respect to the threshold value belowTratio or BelowTdiff.

$$\frac{\|\hat{u}_x^i(x)\|}{\|\hat{u}_x^{i-1}(x)\|} \geq belowTratio \quad (70)$$

or $$\|\hat{u}_x^i(x) - \hat{u}_x^{i-1}(x)\| \geq belowTdiff, \quad (70')$$

where $\|\hat{u}_x^i(x)\|$ and $\|\hat{u}_x^{i-1}(x)\|$ are respectively norms (magnitudes) of the i th and i−1 th estimates of the residual components.

To prevent phase matching (process 1) from diverging, in the below-described methods 3-2, 3-3, 3-4, and 3-5, by freely using the condition (70) or (70'), estimation error is reduced of the residual component. Thus, even if the SNR of the ultrasound echo signals are low, accurate 1D displacement component measurement can be realized.

[Method 3-2]

The flowchart of the method 3-2 is shown in FIG. 11. To prevent phase matching from diverging at the process 1 of the method 3-1, estimation error is reduced of the residual component. Thus, even if the SNR of the ultrasound echo signals are low, accurate 1D displacement component measurement can be realized.

The procedure of iterative estimation is different from that of the method 3-1. At i th estimate (i≧1), the following processes are performed.

(Process 1: Estimation of the 1D Residual Displacement Component Distribution)

Phase matching and estimation of the 1D residual displacement component are performed at every point x in the 1D ROI. That is, the processes 1 and 2 of the method 3-1 are performed once at every point in the ROI. Thus, the estimate of the 1D residual component distribution is obtained.

(Process 2: Update of the Estimate of the 1D Displacement Component Distribution)

The i−1 th estimate of the 1D displacement component distribution is updated using i th estimate of the 1D residual component distribution.

$$dx^i(x) = \hat{d}_x^{i-1}(x) + \hat{u}_x^i(x) \tag{71}$$

Next, this estimate is 1D low pass filtered or 1D median filter to yield the estimate of the 1D displacement component distribution:

$$\hat{d}_x^i(x) = LPF[dx^i(x)], \text{ or } \hat{d}_x^i(x) = MED[dx^i(x)]. \tag{72}$$

Thus, the estimation error is reduced of the residual component compared with process 2 of the method 3-1 [eq. (63)]. Hence, phase matching of the process 1 of method 3-2 is performed using smoothed estimate of the 1D displacement component distribution.

[Process 3: Condition for Heightening the Spatial Resolution of the 1D Displacement Component Distribution Measurement (Condition for Making the Local Region Small)]

In order to make the spatial resolution high of the 1D displacement component distribution measurement, during iterative estimation, the local region used for each point is made small, or the local region used over the ROI is made small.

The criteria for each point is below-described. The processes 1 and 2 (method 3-2) are iteratively carried out till the criteria is satisfied with. When the criteria is satisfied with, the local region is made small, for instance, the length of the local region is made half. For instance, the criteria is (73) or (73') with respect to threshold values Tratio or Tdiff.

$$\frac{\|\hat{u}_x^i(x)\|}{\|\hat{u}_x^{i-1}(x)\|} \leq Tratio \tag{73}$$

or $$\|\hat{u}_x^i(x) - \hat{u}_x^{i-1}(x)\| \leq Tdiff, \tag{73'}$$

where $\|\hat{u}_x^i(x)\|$ and $\|\hat{u}_x^{i-1}(x)\|$ are respectively norms (magnitudes) of the i th and i−1 th estimates of the residual components.

The criteria over the ROI is below-described. The processes 1 and 2 (method 3-2) are iteratively carried out till the criteria is satisfied with. When the criteria is satisfied with, the local region is made small, for instance, the length of the local region is made half. For instance, the criteria is (74) or (74') with respect to threshold values Tratioroi or Tdiffroi.

$$\frac{\sum_{x \in ROI} \|\hat{u}_x^i(x)\|^2}{\sum_{x \in ROI} \|\hat{u}_x^{i-1}(x)\|^2} \leq Tratioroi \tag{74}$$

or $$\sum_{x \in ROI} \|\hat{u}_x^i(x) - \hat{u}_x^{i-1}(x)\| \leq Tdiffroi, \tag{74'}$$

where $\|\hat{u}_x^i(x)\|$ and $\|\hat{u}_x^{i-1}(x)\|$ are respectively norms (magnitudes) of the i th and i−1 th estimates of the residual components.

(Process 4: Condition for Terminating the Iterative Estimation of the 1D Displacement Component Distribution)

Below-described is the criteria for terminating the iterative estimation of the 1D displacement component distribution. The processes 1, 2 and 3 of method 3-2 are iteratively carried out till the criteria is satisfied with. For instance, the criteria is (75) or (75') with respect to threshold values aboveTratioroi or aboveTdiffroi.

$$\frac{\sum_{x \in ROI} \|\hat{u}_x^i(x)\|^2}{\sum_{x \in ROI} \|\hat{u}_x^{i-1}(x)\|^2} \leq aboveTratioroi \tag{75}$$

or $$\sum_{x \in ROI} \|\hat{u}_x^i(x) - \hat{u}_x^{i-1}(x)\| \leq aboveTdiffroi, \tag{75'}$$

where $\|\hat{u}_x^i(x)\|$ and $\|\hat{u}_x^{i-1}(x)\|$ are respectively norms (magnitudes) of the i th and i−1 th estimates of the residual components.

Final estimate is obtained from eq. (71) or eq. (72).

The initial estimate [eq. (57)] of the iterative estimation of the 1D displacement component is set as zero if a priori data is not given about displacements of body motion nor applied compression. Alternatively, values accurately estimated at neighborhood can be used (high correlation or least squares).

[Method 3-3]

The flowchart of the method 3-3 is shown in FIG. 12. To prevent phase matching from diverging at the process 1 of the method 3-1, estimation error is reduced of the residual component. Possibility of divergence is detected from above-described condition (70) or (70'), and by effectively utilizing method 3-1 and 3-2, even if the SNR of the ultrasound echo signals are low, accurate 1D displacement component measurement can be realized.

At first, the procedure of iterative estimation is same as that of the method 3-2 (Processes 1, 2, 3, and 4). At i th estimate, the following processes are performed.

Phase matching and estimation of the 1D residual displacement component are performed at every point x in the 1D ROI. That is, the processes 1 and 2 of the method 3-1 are performed once at every point in the ROI. Thus, the estimate of the 1D residual component distribution is obtained.

During this estimation, if neither condition (70) nor (70') is satisfied with, the method 3-1 is used. If condition (70) or (70') is satisfied with at points or regions, in the process 2 of the method 3-2, over sufficiently large regions centered on the points or regions, or over the ROI, the estimate $dx^i(x)$ of the 1D displacement component $dx(x)$ can be 1D low pass filtered or 1D median filtered as eq. (76).

$$\hat{d}^i(x) = LPF[dx^i(x)], \text{ or } \hat{d}_x^i(x) = MED[dx^i(x)] \tag{76}$$

Thus, the estimation error is reduced of the residual component compared with process 2 of the method 3-1 [eq. (63)].

Thus, iterative estimation is terminated at the process 5 of the method 3-1 or the process 4 of the method 3-2. Hence, final estimate is obtained from eq. (67), or eq. (71), or eq. (76).

The initial estimate [eq. (57)] of the iterative estimation of the 1D displacement component is set as zero if a priori data is not given about displacements of body motion nor applied compression. Alternatively, values accurately estimated at neighborhood can be used (high correlation or least squares).

[Method 3-4]

The flowchart of the method 3-4 is shown in FIG. 13. To prevent phase matching from diverging at the process 1 of the method 3-1, estimation error is reduced of the residual component. Thus, even if the SNR of the ultrasound echo signals are low, accurate 1D displacement component measurement can be realized.

The procedure of iterative estimation is different from that of the method 3-1. At i th estimate (i≧1), the following processes are performed.

(Process 1: Estimation of the 1D Residual Displacement Component Distribution)

Phase matching and estimation of the 1D residual displacement component are performed at every point x in the 1D ROI. That is, the process 1 of the method 3-1 is performed once at every point in the ROI.

To obtain the estimate $\hat{u}_x^i(x)$ of the residual component distribution $u_x^i(x)$, at every point local 1D echo cross-spectrum is evaluated from the 1D Fourier's transforms of the pre-deformation local 1D ultrasound echo signal $r_1(l)$ and phase-matched post-deformation local 1D ultrasound echo signal $r'_2(l)$. Alternatively, when pre-deformation local 1D ultrasound echo signal is phase-matched, at every point cross-spectrum of $r'_1(l)$ and $r_2(l)$ is evaluated.

The least squares method is implemented on the gradient of the phase with utilization of each weight function, i.e., the squared cross-spectrum $|S_{2,1}^i(l)|^2$, where each weight function is normalized by the power of the cross-spectrum, i.e., $$\sum_l |S_{2,1}^i(l)|^2.$$

Moreover, regularization method is also implemented. That is, by minimizing the next functional with respect to the vector $u^i$ comprised of the 1D residual component distribution $u_x^i(x)$.

$$\text{error}(u^i) = \|a - F u^i\|^2 + \alpha_{1i}\|u^i\|^2 + \alpha_{2i}\|G u^i\|^2 + \alpha_{3i}\|G^T G u^i\|^2 + \alpha_{4i}\|G G^T G u^i\|^2 \tag{77}$$

where a: vector comprised of x distribution of the cross-spectrum phase $\Theta^i(l)$ weighted with cross-spectrum $|S_{2,1}^i(l)|$ normalized by the magnitude of the cross-spectrum $$\sqrt{\sum_l |S_{2,1}^i(l)|^2}$$

evaluated at every point in the 1D ROI.

F: matrix comprised of x distribution of the Fourier's coordinate value l weighted with cross-spectrum $|S_{2,1}^i(l)|$ normalized by the magnitude of the cross-spectrum $$\sqrt{\sum_l |S_{2,1}^i(l)|^2}$$

evaluated at every point in the 1D ROI.

$\alpha_{1i}$, $\alpha_{2i}$, $\alpha_{3i}$, $\alpha_{4i}$: regularization parameter (at least larger than zero)

$Gu^i$: vector comprised of the finite difference approximations of the 1D distribution of the 1D gradient components of the unknown 1D residual components $u_x^i(x)$ $$\frac{\partial}{\partial x} u_x^i(x)$$

$G^T Gu^i$: vector comprised of the finite difference approximations of the 1D distribution of the 1D Laplacians of the unknown 1D residual components $u_x^i(x)$ $$\frac{\partial^2}{\partial x^2} u_x^i(x)$$

$GG^T Gu^i$: vector comprised of the finite difference approximations of the 1D distribution of the 1D gradient components of the 1D Laplacians of the unknown 1D residual components $u_x^i(x)$ $$\frac{\partial}{\partial x}\left(\frac{\partial^2}{\partial x^2} u_x^i(x)\right)$$

As $\|u^i\|^2$, $\|Gu^i\|^2$, $\|G^T Gu^i\|^2$, $\|G^T Gu^i\|^2$ are positive definite, error($u^i$) has one minimum value. Thus, by solving for residual displacement component distribution $u_x^i(x)$ the simultaneous equations:

$$(F^T F + \alpha_{1i} I + \alpha_{2i} G^T G + \alpha_{3i} G^T G G^T G + \alpha_{4i} G^T G G^T G G^T G) u^i = F^T a, \tag{78}$$

estimate $\hat{u}_x^i(x)$ of the residual component distribution $u_x^i(x)$ is stably obtained. Thus, estimation error is reduced of the residual component.

The regularization parameter of important information is set relatively large. Thus, the regularization parameters depend on the correlation of the local echo data (peak value of the cross-correlation function, sharpness of the cross-correlation function, width of the cross-correlation function), the SNR of the cross-spectrum power, etc.; then position of the unknown displacement component etc.

(Process 2: Update of the Estimate of the 1D Displacement Component Distribution)

The i−1 th estimate of the 1D displacement component distribution is updated using i th estimate of the 1D residual component distribution.

$$dx^i(x) = d_x^{i-1}(x) + \hat{u}_x^i(x) \tag{79}$$

Freely, this estimate can be 1D low pass filtered or 1D median filter to yield the estimate of the 1D displacement component distribution.

$$d_x^i(x) = LPF[dx^i(x)], \text{ or } d^i(x) = MED[dx^i(x)] \tag{80}$$

Hence, phase matching of the process 1 of method 3-4 is performed using the 1D residual component data $u_x^i(x)$ obtained from eq. (78), or the 1D component data $dx^i(x)$ obtained from eq. (79), or smoothed estimate obtained from eq. (80).

[Process 3: Condition for Heightening the Spatial Resolution of the 1D Displacement Component Distribution Measurement (Condition for Making the Local Region Small)]

In order to make the spatial resolution high of the 1D displacement component distribution measurement, during iterative estimation, the local region used for each point is made small, or the local region used over the ROI is made small.

The criteria for each point is below-described. The processes 1 and 2 of method 3-4 are iteratively carried out till the criteria is satisfied with. When the criteria is satisfied with, the local region is made small, for instance, the length of the local region is made half. For instance, the criteria is (81) or (81') with respect to threshold values Tratio or Tdiff.

$$\frac{\|\hat{u}_x^i(x)\|}{\|\hat{u}_x^{i-1}(x)\|} \leq Tratio \tag{81}$$

or $$\|\hat{u}_x^i(x) - \hat{u}_x^{i-1}(x)\| \leq Tdiff, \tag{81'}$$

where $\|\hat{u}_x^i(x)\|$ and $\|\hat{u}_x^{i-1}(x)\|$ are respectively norms (magnitudes) of the i th and i−1 th estimates of the residual components.

The criteria over the ROI is below-described. The processes 1 and 2 of method 3-4 are iteratively carried out till the criteria is satisfied with. When the criteria is satisfied with, the local region is made small, for instance, the length of the local region is made half. For instance, the criteria is (82) or (82') with respect to threshold values Tratioroi or Tdiffroi.

$$\frac{\sum_{x \in ROI} \|\hat{u}_x^i(x)\|^2}{\sum_{x \in ROI} \|\hat{u}_x^{i-1}(x)\|^2} \leq Tratioroi \tag{82}$$

or $$\sum_{x \in ROI} \|\hat{u}_x^i(x) - \hat{u}_x^{i-1}(x)\| \leq Tdiffroi, \tag{82'}$$

where $\|\hat{u}_x^i(x)\|$ and $\|\hat{u}_x^{i-1}(x)\|$ are respectively norms (magnitudes) of the i th and i−1 th estimates of the residual components.

(Process 4: Condition for Terminating the Iterative Estimation of the 1D Displacement Component Distribution)

Below-described is the criteria for terminating the iterative estimation of the 1D displacement component distribution. The processes 1, 2 and 3 of method 3-4 are iteratively carried out till the criteria is satisfied with. For instance, the criteria is (83) or (83') with respect to threshold values aboveTratioroi or aboveTdiffroi.

$$\frac{\sum_{x \in ROI} \|\hat{u}_x^i(x)\|^2}{\sum_{x \in ROI} \|\hat{u}_x^{i-1}(x)\|^2} \leq above\, Tratioroi \tag{83}$$

or $$\sum_{x \in ROI} \|\hat{u}_x^i(x) - \hat{u}_x^{i-1}(x)\| \leq above\, Tdiffroi, \tag{83'}$$

where $\|\hat{u}_x^i(x)\|$ and $\|\hat{u}_x^{i-1}(x)\|$ are respectively norms (magnitudes) of the i th and i−1 th estimates of the residual components.

Final estimate is obtained from eq. (79) or eq. (80).

The initial estimate [eq. (57)] of the iterative estimation of the 1D displacement component is set zero if a priori data is not given about displacements of body motion nor applied compression. Alternatively, values accurately estimated at neighborhood can be used (high correlation or least squares).

[Method 3-5]

The flowchart of the method 3-5 is shown in FIG. 14. To prevent phase matching from diverging at the process 1 of the method 3-1, estimation error is reduced of the residual component. Possibility of divergence is detected from above-described condition (70) or (70'), and by effectively utilizing method 3-1 and 3-4, even if the SNR of the ultrasound echo signals are low, accurate 1D displacement component measurement can be realized.

At first, the procedure of iterative estimation is same as that of the method 3-4 (Processes 1, 2, 3, and 4). At i th estimate, the following processes are performed.

Phase matching and estimation of the 1D residual displacement component are performed at every point x in the 1D ROI. That is, the process 1 of the method 3-1 is performed once at every point in the ROI. Moreover, using the regularization method, stably the estimate of the 1D residual component distribution is obtained.

i−1 th estimate $\hat{d}_x^{i-1}(x)$ of 1D displacement component distribution dx(x).

i th estimate $\hat{u}_x^i(x)$ of 1D residual component distribution $u_x^i(x)$.

During this estimation, if neither condition (70) nor (70') is satisfied with, the method 3-1 is used. If condition (70) or (70') is satisfied with at points or regions, in the process 2 of the method 3-4, over sufficiently large regions centered on the points or regions, or over the ROI, the estimate $dx^i(x)$ of the 1D displacement component dx(x) can be 1D low pass filtered or 1D median filtered as eq. (84).

$$\hat{d}_x^i(x) = LPF[dx^i(x)], \text{ or } \hat{d}^i(x) = MED[dx^i(x)] \tag{84}$$

Thus, the estimation error is reduced of the residual component.

Iterative estimation is terminated at the process 5 of the method 3-1 or the process 4 of the method 3-4. Hence, final estimate is obtained from eq. (67), or eq. (79), or eq. (84).

The initial estimate [eq. (57)] of the iterative estimation of the 1D displacement component is set as zero if a priori data is not given about displacements of body motion nor applied compression. Alternatively, values accurately estimated at neighborhood can be used (high correlation or least squares).

(IV) Method 4: Measurement of 2D Displacement Component Vector Distribution in 3D SOI

[Method 4-1]

2D displacement component vector distribution in 3D SOI can be measured by measuring 2D displacement component vector distribution in each (x,y) plane by means of the method 2-1, or 2-2, or 2-3, or 2-4, or 2-5 (FIG. 21).

(Process 1)

In each (x,y) plane in 3D SOI, the method 2-1, or 2-2, or 2-3, or 2-4, or 2-5 is utilized. The initial estimate [eq. (29)]of the iterative estimation of the 2D displacement vector in the 3D SOI is set as zero vector if a priori data is not given about displacements of body motion nor applied compression. Alternatively, values accurately estimated at neighborhood can be used (high correlation or least squares).

Moreover, the methods 4-2, 4-3, 4-4, and 4-5 are respectively baesd on the methods 2-2, 2-3, 2-4, and 2-5.

[Method 4-2]

The flowchart of the method 4-2 is shown in FIG. 22. As example, let's consider measurement of 2D displacement vector d(x,y,z) [=(dx(x,y,z),dy(x,y,z))$^T$] in 3D SOI. At i th estimate (i≧1), the following processes are performed.

(Process 1: Estimation of the 2D Residual Displacement Component Vector Distribution in 3D SOI)

Phase matching and estimation of the 2D residual displacement vector are performed at every point (x,y,z) in the 3D SOI. That is, the processes 1 and 2 of the method 2-1 are performed once at every point in the 3 D SOI. Thus, the i th estimate of the 2D residual component vector distribution u$^i$(x,y,z) is obtained as $$\hat{u}^i(x,y,z)[=(\hat{u}_x^i(x,y,z),\hat{u}_y^i(x,y,z))^T].$$

(Process 2: Update of the Estimate of the 2D Displacement Component Vector Distribution in 3D SOI)

The i−1 th estimate of the 2D displacement component vector distribution in the 3D SOI is updated using i th estimate of the 2D residual component vector distribution in the 3D SOI.

$$d^i(x,y,z)=d^{i-1}(x,y,z)+\hat{u}^i(x,y,z) \quad (85)$$

Next, this estimate is 3D low pass filtered or 3D median filter to yield the estimate of the 2D displacement component vector distribution:

$$d^i(x,y,z)=LPF[d^i(x,y,z)] \text{ or } d^i(x,y,z)=MED[d^i(x,y,z)]. \quad (86)$$

Thus, the estimation error is reduced of the residual vector compared with process 2 of the method 2-1 [eq. (35)]. Hence, phase matching of the process 1 of method 4-2 is performed using smoothed estimate $\hat{d}_i(x,y,z)$ of the 2D displacement component vector distribution in the 3D SOI.

[Process 3: Condition for Heightening the Spatial Resolution of the 2D Displacement Component Vector Distribution Measurement in 3D SOI (Condition for Making the Local Region Small)]

In order to make the spatial resolution high of the 2D displacement component vector distribution measurement in the 3D SOI, during iterative estimation, the local region used for each point is made small, or the local region used over the 3D SOI is made small.

The criteria for each point is below-described. The processes 1 and 2 (method 4-2) are iteratively carried out till the criteria is satisfied with. When the criteria is satisfied with, the local region is made small, for instance, the length of each side is made half. For instance, the criteria is (87) or (87') with respect to threshold values Tratio or Tdiff.

$$\frac{\|\hat{u}^i(x,y,z)\|}{\|\hat{u}^{i-1}(x,y,z)\|} \leq Tratio \quad (87)$$

or $$\|\hat{u}^i(x,y,z) - \hat{u}^{i-1}(x,y,z)\| \leq Tdiff, \quad (87')$$

where ||û$^i$(x,y,z)|| and ||û$^{i-1}$(x,y,z)|| are respectively norms (magnitudes) of the i th and i−1 th estimates of the residual vectors.

The condition (87) or (87') can be applied to each direction component, and in this case the side is shorten in each direction.

The criteria over the 3D SOI is below-described. The processes 1 and 2 (method 4-2) are iteratively carried out till the criteria is satisfied with. When the criteria is satisfied with, the local region is made small, for instance, the length of each side is made half. For instance, the criteria is (88) or (88') with respect to threshold values Tratioroi or Tdiffroi.

$$\frac{\sum_{(x,y,z)\in SOI}\|\hat{u}^i(x,y,z)\|^2}{\sum_{(x,y,z)\in SOI}\|\hat{u}^{i-1}(x,y,z)\|^2} \leq Tratioroi \quad (88)$$

or $$\sum_{(x,y,z)\in SOI}\|\hat{u}^i(x,y,z) - \hat{u}^{i-1}(x,y,z)\| \leq Tdiffroi, \quad (88')$$

where ||û$^i$(x,y,z)|| and ||û$^{i-1}$(x,y,z)|| are respectively norms (magnitudes) of the i th and i−1 th estimates of the residual vectors.

The condition (88) or (88') can be applied to each direction component, and in this case the side is shorten in each direction.

(Process 4: Condition for Terminating the Iterative Estimation of the 2D Displacement Component Vector Distribution in 3D SOI)

Below-described is the criteria for terminating the iterative estimation of the 2D displacement component vector distribution in the 3D SOI. The processes 1, 2 and 3 of method 4-2 are iteratively carried out till the criteria is satisfied with. For instance, the criteria is (89) or (89') with respect to threshold values aboveTratioroi or aboveTdiffroi.

$$\frac{\sum_{(x,y,z)\in SOI}\|\hat{u}^i(x,y,z)\|^2}{\sum_{(x,y,z)\in SOI}\|\hat{u}^{i-1}(x,y,z)\|^2} \leq \text{above } Tratioroi \quad (89)$$

or $$\sum_{(x,y,z)\in SOI}\|\hat{u}^i(x,y,z) - \hat{u}^{i-1}(x,y,z)\| \leq \text{above } Tdiffroi, \quad (89')$$

where ||û$^i$(x,y,z)|| and ||û$^{i-1}$(x,y,z)|| are respectively norms (magnitudes) of the i th and i−1 th estimates of the residual vectors.

Final estimate is obtained from eq. (85) or eq. (86).

The initial estimate [eq. (29)] of the iterative estimation of the 2D displacement vector is set as zero vector if a priori data is not given about displacements of body motion nor applied compression. Alternatively, values accurately estimated at neighborhood can be used (high correlation or least squares).

[Method 4-3]

The flowchart of the method 4-3 is shown in FIG. 23. As example, let's consider measurement of 2D displacement vector d(x,y,z) [=(dx(x,y,z),dy(x,y,z))$^T$] in 3D SOI.

Possibility of divergence is detected from above-described condition (42) or (42') in above-described process 1 of the method 4-2, and by effectively utilizing the method 4-1 based on the method 2-1, even if the SNR of the ultrasound echo signals are low, accurate 2D displacement vector measurement can be realized.

At first, the procedure of iterative estimation is same as that of the method 4-2 (Processes 1, 2, 3, and 4). At i th estimate, the following processes are performed.

The process 1 of the method 4-2 is performed. (Phase matching and estimation of the 2D residual displacement vector are performed at every point (x,y,z) in the 3D SOI.) That is, the processes 1 and 2 of the method 2-1 are performed once at every point in the 3D SOI. Thus, the estimate of the 2D residual component vector distribution is obtained.

During this estimation, if neither condition (42) nor (42') is satisfied with, the method 4-1 is used. If condition (42) or (42') is satisfied with at points or regions, in the process 2 of the method 4-2, over sufficiently large regions centered on the points or regions, or over the 3D SOI, the estimate $d^i(x,y,z)$ [eq. (85)] of the 2D displacement vector $d(x,y,z)$ can be 3D low pass filtered or 3D median filtered as eq. (90). Thus, the estimation error is reduced of the residual vector compared with process 2 of the method 2-1 [eq. (35)].

$$d^i(x,y,z)=LPF[d^i(x,y,z)], \text{ or } d^i(x,y,z)=MED[d^i(x,y,z)] \tag{90}$$

Thus, iterative estimation is terminated at the process 1 of the method 4-1 based on the method 2-1, or the process 4 of the method 4-2. Hence, final estimate is obtained from eq. (39), or eq. (85), or eq. (90).

The initial estimate [eq. (29)] of the iterative estimation of the 2D displacement vector is set as zero vector if a priori data is not given about displacements of body motion nor applied compression. Alternatively, values accurately estimated at neighborhood can be used (high correlation or least squares).

[Method 4-4]

The flowchart of the method 4-4 is shown in FIG. 24. As example, let's consider measurement of 2D displacement vector $d(x,y,z)$ $[=(dx(x,y,z),dy(x,y,z))^T]$ in 3D SOI. At i th estimate ($i \geq 1$), the following process 1 is performed.

(Process 1: Estimation of the 2D Residual Displacement Component Vector Distribution in 3D SOI)

Phase matching and estimation of the 2D residual displacement vector are performed at every point (x,y,z) in the 3D SOI. That is, the process 1 of the method 2-1 is performed once at every point in the 3D SOI.

To obtain the estimate $\hat{u}^i(x,y,z)$ $[=(\hat{u}_x^i(x,y,z), \hat{u}_y^i(x,y,z))^T]$ of the 2D residual component vector distribution $u^i(x,y,z)$ $[=(u_x^i(x,y,z), u_y^i(x,y,z))^T]$ in the 3D SOI, at every point local 2D echo cross-spectrum [eq. (31)] is evaluated from the 2D Fourier's transforms of the pre-deformation local 2D ultrasound echo signal $r_1(l,m)$ and phase-matched post-deformation local 2D ultrasound echo signal $r'_2(l,m)$. Alternatively, when pre-deformation local 2D ultrasound echo signal is phase-matched, at every point cross-spectrum of $r'_1(l,m)$ and $r_2(l,m)$ is evaluated.

The least squares method is implemented on the gradient of the phase with utilization of each weight function, i.e., the squared cross-spectrum $|S_{2,1}^i(l,m)|^2$, where each weight function is normalized by the power of the cross-spectrum, i.e., $$\sum_{l,m} |S_{2,1}^i(l,m)|^2$$

[eq. (34)]. Moreover, regularization method is also implemented. That is, by minimizing the next functional with respect to the vector $u^i$ comprised of the 2D residual component vector distribution $u^i(x,y,z)$ in the 3D SOI.

$$\text{error}(u^i) = \tag{91}$$
$$\|a - Fu^i\|^2 + \alpha_{1i}\|u^i\|^2 + \alpha_{2i}\|Gu^i\|^2 + \alpha_{3i}\|G^T G u^i\|^2 + \alpha_{4i}\|GG^T G u^i\|^2$$

where a: vector comprised of (x,y,z) distribution of the cross-spectrum phase $\Theta^i(l,m)$ weighted with cross-spectrum $|S_{2,1}^i(l,m)|$ normalized by the magnitude of the cross-spectrum $$\sqrt{\sum_{l,m} |S_{2,1}^i(l,m)|^2}$$

evaluated at every point in the 3D SOI.

F: matrix comprised of (x,y,z) distribution of the Fourier's coordinate value (l,m) weighted with cross-spectrum $|S_{2,1}^i(l,m)|$ normalized by the magnitude of the cross-spectrum $$\sqrt{\sum_{l,m} |S_{2,1}^i(l,m)|^2}$$

evaluated at every point in the 3D SOI.

$\alpha_{1i}, \alpha_{2i}, \alpha_{3i}, \alpha_{4i}$: regularization parameter (at least larger than zero)

$Gu^i$: vector comprised of the finite difference approximations of the 3D distributions of the 3D gradient components of the unknown 2D residual vector $u^i(x,y,z)$ components $$\frac{\partial}{\partial x}u_x^i(x,y,z), \frac{\partial}{\partial y}u_x^i(x,y,z), \frac{\partial}{\partial z}u_x^i(x,y,z),$$
$$\frac{\partial}{\partial x}u_y^i(x,y,z), \frac{\partial}{\partial y}u_y^i(x,y,z), \frac{\partial}{\partial z}u_y^i(x,y,z)$$

$G^T G u^i$: vector comprised of the finite difference approximations of the 3D distributions of the 3D Laplacian of the unknown 2D residual vector $u^i(x,y,z)$ components $$\frac{\partial^2}{\partial x^2}u_x^i(x,y,z) + \frac{\partial^2}{\partial y^2}u_x^i(x,y,z) + \frac{\partial^2}{\partial z^2}u_x^i(x,y,z)$$
$$\frac{\partial^2}{\partial x^2}u_y^i(x,y,z) + \frac{\partial^2}{\partial y^2}u_y^i(x,y,z) + \frac{\partial^2}{\partial z^2}u_y^i(x,y,z)$$

$GG^T G u^i$: vector comprised of the finite difference approximations of the 3D distributions of the 3D gradient components of the 3D Laplacians of the unknown 2D residual vector $u^i(x,y,z)$ components $$\frac{\partial}{\partial x}\left(\frac{\partial^2}{\partial x^2}u_x^i(x,y,z) + \frac{\partial^2}{\partial y^2}u_x^i(x,y,z) + \frac{\partial^2}{\partial z^2}u_x^i(x,y,z)\right),$$
$$\frac{\partial}{\partial y}\left(\frac{\partial^2}{\partial x^2}u_x^i(x,y,z) + \frac{\partial^2}{\partial y^2}u_x^i(x,y,z) + \frac{\partial^2}{\partial z^2}u_x^i(x,y,z)\right),$$
$$\frac{\partial}{\partial z}\left(\frac{\partial^2}{\partial x^2}u_x^i(x,y,z) + \frac{\partial^2}{\partial y^2}u_x^i(x,y,z) + \frac{\partial^2}{\partial z^2}u_x^i(x,y,z)\right),$$

-continued $$\frac{\partial}{\partial x}\left(\frac{\partial^2}{\partial x^2}u_y^i(x,y,z)+\frac{\partial^2}{\partial y^2}u_y^i(x,y,z)+\frac{\partial^2}{\partial z^2}u_y^i(x,y,z)\right),$$

$$\frac{\partial}{\partial y}\left(\frac{\partial^2}{\partial x^2}u_y^i(x,y,z)+\frac{\partial^2}{\partial y^2}u_y^i(x,y,z)+\frac{\partial^2}{\partial z^2}u_y^i(x,y,z)\right),$$

$$\frac{\partial}{\partial z}\left(\frac{\partial^2}{\partial x^2}u_y^i(x,y,z)+\frac{\partial^2}{\partial y^2}u_y^i(x,y,z)+\frac{\partial^2}{\partial z^2}u_y^i(x,y,z)\right)$$

As $\|u^i\|^2$, $\|Gu^i\|^2$, $\|G^TGu^i\|^2$, $\|GG^TGu^i\|^2$ are positive definite, error($u^i$) has one minimum value. Thus, by solving for 2D residual displacement component vector distribution $u^i(x,y,z)$ in the 3D SOI the simultaneous equations:

$$(F^TF+\alpha_{1i}I+\alpha_{2i}G^TG+\alpha_{3i}G^TGG^TG+\alpha_{4i}G^TGG^TGG^TG)u^i=F^Ta, \quad (92\text{-}1)$$

estimate $\hat{u}^i(x,y,z)$ $[=(\hat{u}_x^i(x,y,z),\hat{u}_y^i(x,y,z))^T]$ of the 2D residual component vector distribution $u^i(x,y,z)$ $[=(u_x^i(x,y,z), u_y^i(x,y,z))^T]$ is stably obtained. Thus, estimation error is reduced of the residual vector.

The regularization parameter of important information is set relatively large. Thus, the regularization parameters depend on the correlation of the local echo data (peak value of the cross-correlation function, sharpness of the cross-correlation function, width of the cross-correlation function), the SNR of the cross-spectrum power, etc.; then position of the unknown displacement vector, direction of the unknown displacement component, direction of the partial derivative, etc.

(Process 2: Update of the Estimate of the 2D Displacement Component Vector Distribution)

The i−1 th estimate of the 2D displacement component vector distribution is updated using i th estimate of the 2D residual component vector distribution.

$$d^i(x,y,z)=d^{i-1}(x,y,z)+\hat{u}^i(x,y,z) \quad (92\text{-}2)$$

Freely, this estimate can be 3D low pass filtered or 3D median filter to yield the estimate of the 2D displacement component vector distribution.

$$d^i(x,y,z)=LPF[d^i(x,y,z)], \text{ or } d^i(x,y,z)=MED[d^i(x,y,z)] \quad (93)$$

Hence, phase matching of the process 1 of method 4-4 is performed using the 2D residual vector data $u^i(x,y,z)$ obtained from eq. (91), or the 2D vector data $d^i(x,y,z)$ obtained from eq. (92-2), or smoothed estimate obtained from eq. (93).

[Process 3: Condition for Heightening the Spatial Resolution of the 2D Displacement Component Vector Distribution Measurement in 3D SOI (Condition for Making the Local Region Small)]

In order to make the spatial resolution high of the 2D displacement component vector distribution measurement, during iterative estimation, the local region used for each point is made small, or the local region used over the 3D SOI is made small.

The criteria for each point is below-described. The processes 1 and 2 of method 4-4 are iteratively carried out till the criteria is satisfied with. When the criteria is satisfied with, the local region is made small, for instance, the length of each side is made half. For instance, the criteria is (94) or (94') with respect to threshold values Tratio or Tdiff.

$$\frac{\|\hat{u}^i(x,y,z)\|}{\|\hat{u}^{i-1}(x,y,z)\|}\leq Tratio \quad (94)$$

or $$\|\hat{u}^i(x,y,z)-\hat{u}^{i-1}(x,y,z)\|\leq Tdiff, \quad (94')$$

where $\|\hat{u}^i(x,y,z)\|$ and $\|\hat{u}^{i-1}(x,y,z)\|$ are respectively norms (magnitudes) of the i th and i−1 th estimates of the residual vectors.

The condition (94) or (94') can be applied to each direction component, and in this case the side is shorten in each direction.

The criteria over the 3D SOI is below-described. The processes 1 and 2 of method 4-4 are iteratively carried out till the criteria is satisfied with. When the criteria is satisfied with, the local region is made small, for instance, the length of each side is made half. For instance, the criteria is (95) or (95') with respect to threshold values Tratioroi or Tdiffroi.

$$\frac{\sum_{(x,y,z)\in SOI}\|\hat{u}^i(x,y,z)\|^2}{\sum_{(x,y,z)\in SOI}\|\hat{u}^{i-1}(x,y,z)\|^2}\leq Tratioroi \quad (95)$$

or $$\sum_{(x,y,z)\in SOI}\|\hat{u}^i(x,y,z)-\hat{u}^{i-1}(x,y,z)\|\leq Tdiffroi, \quad (95')$$

where $\|\hat{u}^i(x,y,z)\|$ and $\|\hat{u}^{i-1}(x,y,z)\|$ are respectively norms (magnitudes) of the i th and i−1 th estimates of the residual vectors.

The condition (95) or (95') can be applied to each direction component, and in this case the side is shorten in each direction.

(Process 4: Condition for Terminating the Iterative Estimation of the 2D Displacement Component Vector Distribution in 3D SOI)

Below-described is the criteria for terminating the iterative estimation of the 2D displacement component vector distribution. The processes 1, 2 and 3 of method 4-4 are iteratively carried out till the criteria is satisfied with. For instance, the criteria is (96) or (96') with respect to threshold values aboveTratioroi or aboveTdiffroi.

$$\frac{\sum_{(x,y,z)\in SOI}\|\hat{u}^i(x,y,z)\|^2}{\sum_{(x,y,z)\in SOI}\|\hat{u}^{i-1}(x,y,z)\|^2}\leq aboveTratioroi \quad (96)$$

or $$\sum_{(x,y,z)\in SOI}\|\hat{u}^i(x,y,z)-\hat{u}^{i-1}(x,y,z)\|\leq aboveTdiffroi, \quad (96')$$

where $\|\hat{u}^i(x,y,z)\|$ and $\|\hat{u}^{i-1}(x,y,z)\|$ are respectively norms (magnitudes) of the i th and i−1 th estimates of the residual vectors.

Final estimate is obtained from eq. (92-2) or eq. (93).

The initial estimate [eq. (29)] of the iterative estimation of the 2D displacement vector is set as zero vector if a priori data is not given about displacements of body motion nor applied compression. Alternatively, values accurately estimated at neighborhood can be used (high correlation or least squares).

[Method 4-5]

The flowchart of the method 4-5 is shown in FIG. 25. As example, let's consider measurement of 2D displacement vector $d(x,y,z) [=(dx(x,y,z),dy(x,y,z))^T]$ in 3D SOI.

Possibility of divergence is detected from above-described condition (42) or (42') in above-described process 1 of the method 4-4, and by effectively utilizing the method 4-1 based on the method 2-1, even if the SNR of the ultrasound echo signals are low, accurate 2D displacement vector measurement can be realized.

At first, the procedure of iterative estimation is same as that of the method 4-4 (Processes 1, 2, 3, and 4). At i th estimate, the following processes are performed.

The process 1 of the method 4-4 is performed. (Phase matching and estimation of the 2D residual displacement vector are performed at every point (x,y,z) in the 3D SOI.) That is, the process 1 of the method 2-1 is performed once at every point in the 3D SOI. Moreover, using the regularization method, stably the estimate of the 2D residual component vector distribution is obtained.

i−1 th estimate $\hat{d}^{i-1}(x,y,z)$ of 2D displacement component vector distribution $d(x,y,z)$.

i th estimate $\hat{u}^i(x,y,z)$ of 2D residual component vector distribution $u^i(x,y,z)$.

During this estimation, if neither condition (42) nor (42') is satisfied with, the method 4-1 based on the method 2-1 is used. If condition (42) or (42') is satisfied with at points or regions, in the process 2 of the method 4-4, over sufficiently large regions centered on the points or regions, or over the 3D SOI, the estimated $d^i(x,y,z)$ of the 2D displacement vector $d(x,y,z)$ can be 3D low pass filtered or 3D median filtered as eq. (97).

$$\hat{d}^i(x,y,z)=LPF[d^i(x,y,z)], \text{ or } \hat{d}^i(x,y,z)=MED[d^i(x,y,z)] \quad (97)$$

Thus, the estimation error is reduced of the residual vector.

Iterative estimation is terminated at the process 1 of the method 4-1 based on the method 2-1, or the process 4 of the method 4-4. Hence, final estimate is obtained from eq. (39), or eq. (92-2), or eq. (97).

The initial estimate [eq. (29)] of the iterative estimation of the 2D displacement vector is set as zero vector if a priori data is not given about displacements of body motion nor applied compression. Alternatively, values accurately estimated at neighborhood can be used (high correlation or least squares).

(V) Method 5: Measurement of 1D Displacement (One Direction) Component Distribution in 3D SOI

[Method 5-1]

1Dx displacement component distribution in 3D SOI can be measured by measuring 1Dx displacement component distribution in each line being parallel to x axis by means of the method 3-1, or 3-2, or 3-3, or 3-4, or 3-5 (FIG. 21).

(Process 1)

In each line being parallel to x axis in 3D SOI, the method 3-1, or 3-2, or 3-3, or 3-4, or 3-5 is utilized. The initial estimate [eq. (57)] of the iterative estimation of the 1D displacement component in the 3D SOI is set as zero if a priori data is not given about displacements of body motion nor applied compression. Alternatively, values accurately estimated at neighborhood can be used (high correlation or least squares).

Moreover, the methods 5-2, 5-3, 5-4, and 5-5 are respectively baesd on the methods 3-2, 3-3, 3-4, and 3-5.

[Method 5-2]

The flowchart of the method 5-2 is shown in FIG. 22. As example, let's consider measurement of 1D displacement component $dx(x,y,z)$ in 3D SOI. At i th estimate (i≧1), the following processes are performed.

(Process 1: Estimation of the 1D Residual Displacement Component Distribution in 3D SOI)

Phase matching and estimation of the 1D residual displacement component are performed at every point (x,y,z) in the 3D SOI. That is, the processes 1 and 2 of the method 3-1 are performed once at every point in the 3D SOI. Thus, the i th estimate of the 1D residual component distribution $u_x^i(x,y,z)$ is obtained as $\hat{u}_x^i(x,y,z)$.

(Process 2: Update of the Estimate of the 1D Displacement Component Distribution in 3D SOI)

The i−1 th estimate of the 1D displacement component distribution in the 3D SOI is updated using i th estimate of the 1D residual component distribution in the 3D SOI.

$$dx^i(x,y,z)=\hat{d}_x^{i-1}(x,y,z)+\hat{u}_x^i(x,y,z) \quad (98)$$

Next, this estimate is 3D low pass filtered or 3D median filter to yield the estimate of the 1D displacement component distribution:

$$\hat{d}_x^i(x,y,z)=LPF[dx^i(x,y,z)], \text{ or}$$
$$\hat{d}_x^i(x,y,z)=MED[dx^i(x,y,z)]. \quad (99)$$

Thus, the estimation error is reduced of the residual component compared with process 2 of the method 3-1 [eq. (63)]. Hence, phase matching of the process 1 of method 5-2 is performed using smoothed estimate $\hat{d}_x^i(x,y,z)$ of the 1D displacement component distribution in the 3D SOI.

[Process 3: Condition for Heightening the Spatial Resolution of the 1D Displacement Component Distribution Measurement in 3D SOI (Condition for Making the Local Region Small)]

In order to make the spatial resolution high of the 1D displacement component distribution measurement in the 3D SOI, during iterative estimation, the local region used for each point is made small, or the local region used over the 3D SOI is made small.

The criteria for each point is below-described. The processes 1 and 2 (method 5-2) are iteratively carried out till the criteria is satisfied with. When the criteria is satisfied with, the local region is made small, for instance, the length of the local region is made half. For instance, the criteria is (87) or (87') with respect to threshold values Tratio or Tdiff.

$$\frac{\|\hat{u}_x^i(x,y,z)\|}{\|\hat{u}_x^{i-1}(x,y,z)\|} \leq Tratio \quad (100)$$

or $$\|\hat{u}_x^i(x,y,z)-\hat{u}_x^{i-1}(x,y,z)\| \leq Tdiff, \quad (100')$$

where $\|\hat{u}_x^i(x,y,z)\|$ and $\|\hat{u}_x^{i-1}(x,y,z)\|$ are respectively norms (magnitudes) of the i th and i−1 th estimates of the residual components.

The criteria over the 3D SOI is below-described. The processes 1 and 2 (method 5-2) are iteratively carried out till the criteria is satisfied with. When the criteria is satisfied with, the local region is made small, for instance, the length of the local region is made half. For instance, the criteria is (101) or (101') with respect to threshold values Tratioroi or Tdiffroi.

$$\frac{\sum_{(x,y,z)\in SOI}\|\hat{u}_x^i(x,y,z)\|^2}{\sum_{(x,y,z)\in SOI}\|\hat{u}_x^{i-1}(x,y,z)\|^2} \le Tratioroi \quad (101)$$

or $$\sum_{(x,y,z)\in SOI}\|\hat{u}_x^i(x,y,z) - \hat{u}_x^{i-1}(x,y,z)\| \le Tdiffroi, \quad (101')$$

where $\|\hat{u}_x^i(x,y,z)\|$ and $\|\hat{u}_x^{i-1}(x,y,z)\|$ are respectively norms (magnitudes) of the i th and i−1 th estimates of the residual components.

(Process 4: Condition for Terminating the Iterative Estimation of the 1D Displacement Component Distribution in 3D SOI)

Below-described is the criteria for terminating the iterative estimation of the 1D displacement component distribution in the 3D SOI. The processes 1, 2 and 3 of method 5-2 are iteratively carried out till the criteria is satisfied with. For instance, the criteria is (102) or (102') with respect to threshold values aboveTratioroi or aboveTdiffroi.

$$\frac{\sum_{(x,y,z)\in SOI}\|\hat{u}_x^i(x,y,z)\|^2}{\sum_{(x,y,z)\in SOI}\|\hat{u}_x^{i-1}(x,y,z)\|^2} \le aboveTratioroi \quad (102)$$

or $$\sum_{(x,y,z)\in SOI}\|\hat{u}_x^i(x,y,z) - \hat{u}_x^{i-1}(x,y,z)\| \le aboveTdiffroi, \quad (102')$$

where $\|\hat{u}_x^i(x,y,z)\|$ and $\|\hat{u}_x^{i-1}(x,y,z)\|$ are respectively norms (magnitudes) of the i th and i−1 th estimates of the residual components.

Final estimate is obtained from eq. (98) or eq. (99).

The initial estimate [eq. (57)] of the iterative estimation of the 1D displacement component is set as zero if a priori data is not given about displacements of body motion nor applied compression. Alternatively, values accurately estimated at neighborhood can be used (high correlation or least squares).

[Method 5-3]

The flowchart of the method 5-3 is shown in FIG. 23. As example, let's consider measurement of 1D displacement component dx(x,y,z) in 3D SOI.

Possibility of divergence is detected from above-described condition (70) or (70') in above-described process 1 of the method 5-2, and by effectively utilizing the method 5-1 based on the method 3-1, even if the SNR of the ultrasound echo signals are low, accurate 1D displacement component measurement can be realized.

At first, the procedure of iterative estimation is same as that of the method 5-2 (Processes 1, 2, 3, and 4). At i th estimate, the following processes are performed.

The process 1 of the method 5-2 is performed. (Phase matching and estimation of the 1D residual displacement component are performed at every point (x,y,z) in the 3D SOI.) That is, the processes 1 and 2 of the method 3-1 are performed once at every point in the 3D SOI. Thus, the estimate of the 1D residual component distribution is obtained.

During this estimation, if neither condition (70) nor (70') is satisfied with, the method 5-1 is used. If condition (70) or (70') is satisfied with at points or regions, in the process 2 of the method 5-2, over sufficiently large regions centered on the points or regions, or over the 3D SOI, the estimate $dx^i(x,y,z)$ [eq. (98)] of the 1D displacement component dx(x,y,z) can be 3D low pass filtered or 3D median filtered as eq. (102). Thus, the estimation error is reduced of the residual component compared with process 2 of the method 3-1 [eq. (63)].

$$\hat{d}_x^i(x,y,z) = LPF[dx^i(x,y,z)], \text{ or}$$
$$\hat{d}_x^i(x,y,z) = MED[dx^i(x,y,z)] \quad (102)$$

Thus, iterative estimation is terminated at the process 1 of the method 5-1 based on the method 3-1, or the process 4 of the method 5-2. Hence, final estimate is obtained from eq. (67), or eq. (98), or eq. (102).

The initial estimate [eq. (57)] of the iterative estimation of the 1D displacement component is set as zero if a priori data is not given about displacements of body motion nor applied compression. Alternatively, values accurately estimated at neighborhood can be used (high correlation or least squares).

[Method 5-4]

The flowchart of the method 5-4 is shown in FIG. 24. As example, let's consider measurement of 1D displacement component dx(x,y,z) in 3D SOI. At i th estimate (i≥1), the following process 1 is performed.

(Process 1: Estimation of the 1D Residual Displacement Component Distribution in 3D SOI)

Phase matching and estimation of the 1D residual displacement component are performed at every point (x,y,z) in the 3D SOI. That is, the process 1 of the method 3-1 is performed once at every point in the 3D SOI.

To obtain the estimate $\hat{u}_x^i(x,y,z)$ of the 1D residual component distribution $u_x^i(x,y,z)$ in the 3D SOI, at every point local 1D echo cross-spectrum [eq. (59)] is evaluated from the 1D Fourier's transforms of the pre-deformation local 1D ultrasound echo signal $r_1(l)$ and phase-matched post-deformation local 1D ultrasound echo signal $r'_2(l)$. Alternatively, when pre-deformation local 1D ultrasound echo signal is phase-matched, at every point cross-spectrum of $r'_1(l)$ and $r_2(l)$ is evaluated.

The least squares method is implemented on the gradient of the phase with utilization of each weight function, i.e., the squared cross-spectrum $|S_{2,1}^i(l)|^2$, where each weight function is normalized by the power of the cross-spectrum, i.e., $$\sum_l |S_{2,1}^i(l)|^2$$

[eq. (62)]. Moreover, regularization method is also implemented. That is, by minimizing the next functional with respect to the vector $u^i$ comprised of the 1D residual component distribution $u_x^i(x,y,z)$ in the 3D SOI.

$$\text{error}(u^i) = \|a - F u^i\|^2 + \alpha_{1i}\|u^i\|^2 + \qquad (103)$$
$$\alpha_{2i}\|G u^i\|^2 + \alpha_{3i}\|G^T G u^i\|^2 + \alpha_{4i}\|GG^T G u^i\|^2$$

where a: vector comprised of (x,y,z) distribution of the cross-spectrum phase $\Theta^i(l)$ weighted with cross-spectrum $|S_{2,1}{}^i(l)|$ normalized by the magnitude of the cross-spectrum $$\sqrt{\sum_l |S_{2,1}^i(l)|^2}$$

evaluated at every point in the 3D SOI.

F: matrix comprised of (x,y,z) distribution of the Fourier's coordinate value l weighted with cross-spectrum $|S_{2,1}{}^i(l)|$ normalized by the magnitude of the cross-spectrum $$\sqrt{\sum_l |S_{2,1}^i(l)|^2}$$

evaluated at every point in the 3D SOI.

$\alpha_{1i}, \alpha_{2i}, \alpha_{3i}, \alpha_{4i}$: regularization parameter (at least larger than zero)

$Gu^i$: vector comprised of the finite difference approximations of the 3D distributions of the 3D gradient components of the unknown 1D residual component $u_x{}^i(x,y,z)$ $$\frac{\partial}{\partial x}u_x^i(x,y,z), \frac{\partial}{\partial y}u_x^i(x,y,z), \frac{\partial}{\partial z}u_x^i(x,y,z)$$

$G^T Gu^i$: vector comprised of the finite difference approximations of the 3D distributions of the 3D Laplacian of the unknown 1D residual component $u^i(x,y,z)$ $$\frac{\partial^2}{\partial x^2}u_x^i(x,y,z) + \frac{\partial^2}{\partial y^2}u_x^i(x,y,z) + \frac{\partial^2}{\partial z^2}u_x^i(x,y,z)$$

$GG^T Gu^i$: vector comprised of the finite difference approximations of the 3D distributions of the 3D gradient components of the 3D Laplacians of the unknown 1D residual component $u_x{}^i(x,y,z)$ $$\frac{\partial}{\partial x}\left(\frac{\partial^2}{\partial x^2}u_x^i(x,y,z) + \frac{\partial^2}{\partial y^2}u_x^i(x,y,z) + \frac{\partial^2}{\partial z^2}u_x^i(x,y,z)\right),$$

$$\frac{\partial}{\partial y}\left(\frac{\partial^2}{\partial x^2}u_x^i(x,y,z) + \frac{\partial^2}{\partial y^2}u_x^i(x,y,z) + \frac{\partial^2}{\partial z^2}u_x^i(x,y,z)\right),$$

$$\frac{\partial}{\partial z}\left(\frac{\partial^2}{\partial x^2}u_x^i(x,y,z) + \frac{\partial^2}{\partial y^2}u_x^i(x,y,z) + \frac{\partial^2}{\partial z^2}u_x^i(x,y,z)\right)$$

As $\|u^i\|^2$, $\|Gu^i\|^2$, $\|G^T Gu^i\|^2$, $\|GG^T Gu^i\|^2$ are positive definite, error($u^i$) has one minimum value. Thus, by solving for 1D residual displacement component distribution $u_x{}^i(x,y,z)$ in the 3D SOI the simultaneous equations:

$$(F^T F + \alpha_{1i} I + \alpha_{2i} G^T G + \alpha_{3i} G^T G G^T G + \alpha_{4i} G^T G G^T G G^T G) u^i = F^T a, \quad (104)$$

estimate $\hat{u}_x{}^i(x,y,z)$ of the 1D residual component distribution $u^i{}_x(x,y,z)$ is stably obtained. Thus, estimation error is reduced of the residual component.

The regularization parameter of important information is set relatively large. Thus, the regularization parameters depend on the correlation of the local echo data (peak value of the cross-correlation function, sharpness of the cross-correlation function, width of the cross-correlation function), the SNR of the cross-spectrum power, etc.; then position of the unknown displacement component etc.

(Process 2: Update of the Estimate of the 1D Displacement Component Distribution)

The i-1 th estimate of the 1D displacement component distribution is updated using i th estimate of the 1D residual component distribution.

$$dx^i(x,y,z) = d_x^{i-1}(x,y,z) + \hat{u}_x^i(x,y,z) \quad (105)$$

Freely, this estimate can be 3D low pass filtered or 3D median filter to yield the estimate of the 1D displacement component distribution.

$$d_x^i(x,y,z) = LPF[dx^i(x,y,z)], \text{ or}$$
$$d_x^i(x,y,z) = MED[dx^i(x,y,z)] \quad (106)$$

Hence, phase matching of the process 1 of method 5-4 is performed using the 1D residual component data $u_x{}^i(x,y,z)$ obtained from eq. (104), or the 1D component data $dx^i(x,y,z)$ obtained from eq. (105), or smoothed estimate obtained from eq. (106).

[Process 3: Condition for Heightening the Spatial Resolution of the 1D Displacement Component Distribution Measurement in 3D SOI (Condition for Making the Local Region Small)]

In order to make the spatial resolution high of the 1D displacement component distribution measurement, during iterative estimation, the local region used for each point is made small, or the local region used over the 3D SOI is made small.

The criteria for each point is below-described. The processes 1 and 2 of method 5-4 are iteratively carried out till the criteria is satisfied with. When the criteria is satisfied with, the local region is made small, for instance, the length of the local region is made half. For instance, the criteria is (107) or (107') with respect to threshold values Tratio or Tdiff.

$$\frac{\|\hat{u}_x^i(x,y,z)\|}{\|\hat{u}_x^{i-1}(x,y,z)\|} \leq Tratio \quad (107)$$

or $$\|\hat{u}_x^i(x,y,z) - \hat{u}_x^{i-1}(x,y,z)\| \leq Tdiff, \quad (107')$$

where $\|\hat{u}_x{}^i(x,y,z)\|$ and $\|\hat{u}_x{}^{i-1}(x,y\ z)\|$ are respectively norms (magnitudes) of the i th and i-1 th estimates of the residual components.

The criteria over the 3D SOI is below-described. The processes 1 and 2 of method 5-4 are iteratively carried out till the criteria is satisfied with. When the criteria is satisfied with, the local region is made small, for instance, the length of the local region is made half. For instance, the criteria is (108) or (108') with respect to threshold values Tratioroi or Tdiffroi.

$$\frac{\sum_{(x,y,z)\in SOI} \|\hat{u}_x^i(x,y,z)\|^2}{\sum_{(x,y,z)\in SOI} \|\hat{u}_x^{i-1}(x,y,z)\|^2} \leq Tratioroi \quad (108)$$

or

-continued $$\sum_{(x,y,z)\in SOI} \|\hat{u}_x^i(x, y, z) - \hat{u}_x^{i-1}(x, y, z)\| \leq T\text{diffroi}, \quad (108')$$

where $\|\hat{u}_x^i(x,y,z)\|$ and $\|\hat{u}_x^{i-1}(x,y,z)\|$ are respectively norms (magnitudes) of the i th and i−1 th estimates of the residual components.

(Process 4: Condition for Terminating the Iterative Estimation of the 1D Displacement Component Distribution in 3D SOI)

Below-described is the criteria for terminating the iterative estimation of the 1D displacement component distribution. The processes 1, 2 and 3 of method 5-4 are iteratively carried out till the criteria is satisfied with. For instance, the criteria is (109) or (109') with respect to threshold values aboveTratioroi or aboveTdiffroi.

$$\frac{\sum_{(x,y,z)\in SOI} \|\hat{u}_x^i(x, y, z)\|^2}{\sum_{(x,y,z)\in SOI} \|\hat{u}_x^{i-1}(x, y, z)\|^2} \leq aboveTratioroi \quad (109)$$

or $$\sum_{(x,y,z)\in SOI} \|\hat{u}_x^i(x, y, z) - \hat{u}_x^{i-1}(x, y, z)\| \leq aboveTdiffroi, \quad (109')$$

where $\|\hat{u}_x^i(x,y,z)\|$ and $\|\hat{u}_x^{i-1}(x,y,z)\|$ are respectively norms (magnitudes) of the i th and i−1 th estimates of the residual components.

Final estimate is obtained from eq. (105) or eq. (106).

The initial estimate [eq. (57)] of the iterative estimation of the 1D displacement component is set as zero if a priori data is not given about displacements of body motion nor applied compression. Alternatively, values accurately estimated at neighborhood can be used (high correlation or least squares).

[Method 5-5]

The flowchart of the method 5-5 is shown in FIG. 25. As example, let's consider measurement of 1D displacement component dx(x,y,z) in 3D SOI.

Possibility of divergence is detected from above-described condition (70) or (70') in above-described process 1 of the method 5-4, and by effectively utilizing the method 5-1 based on the method 3-1, even if the SNR of the ultrasound echo signals are low, accurate 1D displacement component measurement can be realized.

At first, the procedure of iterative estimation is same as that of the method 5-4 (Processes 1, 2, 3, and 4). At i th estimate, the following processes are performed.

The process 1 of the method 5-4 is performed. (Phase matching and estimation of the 1D residual displacement component are performed at every point (x,y,z) in the 3D SOI.) That is, the process 1 of the method 3-1 is performed once at every point in the 3D SOI. Moreover, using the regularization method, stably the estimate of the 1D residual component distribution is obtained.

i−1 th estimate $\hat{d}_x^{i-1}(x,y,z)$ of 1D displacement component distribution dx(x,y,z).

i th estimate $\hat{u}_x^i(x,y,z)$ of 1D residual component distribution $u_x^i(x,y,z)$.

During this estimation, if neither condition (70) nor (70') is satisfied with, the method 5-1 based on the method 3-1 is used. If condition (70) or (70') is satisfied with at points or regions, in the process 2 of the method 5-4, over sufficiently large regions centered on the points or regions, or over the 3D SOI, the estimate $dx^i(x,y,z)$ of the 1D displacement component dx(x,y,z) can be 3D low pass filtered or 3D median filtered as eq. (110).

$$\hat{d}_x^i(x,y,z)=LPF[dx^i(x,y,z)], \text{ or}$$
$$\hat{d}_x^i(x,y,z)=MED[dx^i(x,y,z)] \quad (110)$$

Thus, the estimation error is reduced of the residual component.

Iterative estimation is terminated at the process 1 of the method 5-1 based on the method 3-1, or the process 4 of the method 5-4. Hence, final estimate is obtained from eq. (67), or eq. (105), or eq. (110).

The initial estimate [eq. (57)] of the iterative estimation of the 1D displacement component is set as zero if a priori data is not given about displacements of body motion nor applied compression. Alternatively, values accurately estimated at neighborhood can be used (high correlation or least squares).

(VI) Method 6: Measurement of 1D Displacement (One Direction) Component Distribution in 2D ROI

[Method 6-1]

1D× displacement component distribution in 2D ROI can be measured by measuring 1D× displacement component distribution in each line being parallel to x axis by means of the method 3-1, or 3-2, or 3-3, or 3-4, or 3-5 (FIG. 21).

(Process 1)

In each line being parallel to x axis in 2D ROI, the method 3-1, or 3-2, or 3-3, or 3-4, or 3-5 is utilized. The initial estimate [eq. (57)] of the iterative estimation of the 1D displacement component in the 2D ROI is set as zero if a priori data is not given about displacements of body motion nor applied compression. Alternatively, values accurately estimated at neighborhood can be used (high correlation or least squares).

Moreover, the methods 6-2, 6-3, 6-4, and 6-5 are respectively baesd on the methods 3-2, 3-3, 3-4, and 3-5.

[Method 6-2]

The flowchart of the method 6-2 is shown in FIG. 22. As example, let's consider measurement of 1D displacement component dx(x,y) in 2D ROI. At i th estimate (i≧1), the following processes are performed.

(Process 1: Estimation of the 1D Residual Displacement Component Distribution in 2D ROI)

Phase matching and estimation of the 1D residual displacement component are performed at every point (x,y) in the 2D ROI. That is, the processes 1 and 2 of the method 3-1 are performed once at every point in the 2D ROI. Thus, the i th estimate of the 1D residual component distribution $u_x^i(x,y)$ is obtained as $\hat{u}_x^i(x,y)$.

(Process 2: Update of the Estimate of the 1D Displacement Component Distribution in 2D ROI)

The i−1 th estimate of the 1D displacement component distribution in the 2D ROI is updated using i th estimate of the 1D residual component distribution in the 2D ROI.

$$dx^i(x,y)=\hat{d}_x^{i-1}(x,y)+\hat{u}_x^i(x,y) \quad (111)$$

Next, this estimate is 2D low pass filtered or 2D median filter to yield the estimate of the 1D displacement component distribution:

$$\hat{d}_x^i(x,y)=LPF[dx^i(x,y)], \text{ or } \hat{d}_x^i(x,y)=MED[dx^i(x,y)]. \quad (112)$$

Thus, the estimation error is reduced of the residual component compared with process 2 of the method 3-1 [eq. (63)].

Hence, phase matching of the process 1 of method 6-2 is performed using smoothed estimate $\hat{d}_x^i(x,y)$ of the 1D displacement component distribution in the 2D ROI.

[Process 3: Condition for Heightening the Spatial Resolution of the 1D Displacement Component Distribution Measurement in 2D ROI (Condition for Making the Local Region Small)]

In order to make the spatial resolution high of the 1D displacement component distribution measurement in the 2D ROI, during iterative estimation, the local region used for each point is made small, or the local region used over the 2D ROI is made small.

The criteria for each point is below-described. The processes 1 and 2 (method 6-2) are iteratively carried out till the criteria is satisfied with. When the criteria is satisfied with, the local region is made small, for instance, the length of the local region is made half. For instance, the criteria is (113) or (113') with respect to threshold values Tratio or Tdiff.

$$\frac{\|\hat{u}_x^i(x, y)\|}{\|\hat{u}_x^{i-1}(x, y)\|} \le Tratio \tag{113}$$

or $$\|\hat{u}_x^i(x, y) - \hat{u}_x^{i-1}(x, y)\| \le Tdiff, \tag{113'}$$

where $\|\hat{u}_x^i(x,y)\|$ and $\|\hat{u}_x^{i-1}(x,y)\|$ are respectively norms (magnitudes) of the i th and i−1 th estimates of the residual components.

The criteria over the 2D ROI is below-described. The processes 1 and 2 (method 6-2) are iteratively carried out till the criteria is satisfied with. When the criteria is satisfied with, the local region is made small, for instance, the length of the local region is made half. For instance, the criteria is (114) or (114') with respect to threshold values Tratioroi or Tdiffroi.

$$\frac{\sum_{(x,y)\in ROI} \|\hat{u}_x^i(x, y)\|^2}{\sum_{(x,y)\in ROI} \|\hat{u}_x^{i-1}(x, y)\|^2} \le Tratioroi \tag{114}$$

or $$\sum_{(x,y)\in ROI} \|\hat{u}_x^i(x, y) - \hat{u}_x^{i-1}(x, y)\| \le Tdiffroi, \tag{114'}$$

where $\|\hat{u}_x^i(x,y)\|$ and $\|\hat{u}_x^{i-1}(x,y)\|$ are respectively norms (magnitudes) of the i th and i−1 th estimates of the residual components.

(Process 4: Condition for Terminating the Iterative Estimation of the 1D Displacement Component Distribution in 2D ROI)

Below-described is the criteria for terminating the iterative estimation of the 1D displacement component distribution in the 2D ROI. The processes 1, 2 and 3 of method 6-2 are iteratively carried out till the criteria is satisfied with. For instance, the criteria is (115) or (115') with respect to threshold values aboveTratioroi or aboveTdiffroi.

$$\frac{\sum_{(x,y)\in ROI} \|\hat{u}_x^i(x, y)\|^2}{\sum_{(x,y)\in ROI} \|\hat{u}_x^{i-1}(x, y)\|^2} \le aboveTratioroi \tag{115}$$

or $$\sum_{(x,y)\in ROI} \|\hat{u}_x^i(x, y) - \hat{u}_x^{i-1}(x, y)\| \le aboveTdiffroi, \tag{115'}$$

where $\|\hat{u}_x^i(x,y)\|$ and $\|\hat{u}_x^{i-1}(x,y)\|$ are respectively norms (magnitudes) of the i th and i−1 th estimates of the residual components.

Final estimate is obtained from eq. (111) or eq. (112).

The initial estimate [eq. (57)] of the iterative estimation of the 1D displacement component is set as zero if a priori data is not given about displacements of body motion nor applied compression. Alternatively, values accurately estimated at neighborhood can be used (high correlation or least squares).

[Method 6-3]

The flowchart of the method 6-3 is shown in FIG. 23. As example, let's consider measurement of 1D displacement component dx(x,y) in 2D ROI.

Possibility of divergence is detected from above-described condition (70) or (70') in above-described process 1 of the method 6-2, and by effectively utilizing the method 6-1 based on the method 3-1, even if the SNR of the ultrasound echo signals are low, accurate 1D displacement component measurement can be realized.

At first, the procedure of iterative estimation is same as that of the method 6-2 (Processes 1, 2, 3, and 4). At i th estimate, the following processes are performed.

The process 1 of the method 6-2 is performed. (Phase matching and estimation of the 1D residual displacement component are performed at every point (x,y) in the 2D ROI.) That is, the processes 1 and 2 of the method 3-1 are performed once at every point in the 2D ROI. Thus, the estimate of the 1D residual component distribution is obtained.

During this estimation, if neither condition (70) nor (70') is satisfied with, the method 6-1 is used. If condition (70) or (70') is satisfied with at points or regions, in the process 2 of the method 6-2, over sufficiently large regions centered on the points or regions, or over the 2D ROI, the estimate $dx^i(x,y)$ [eq. (111)] of the 1D displacement component dx(x,y) can be 2D low pass filtered or 2D median filtered as eq. (116). Thus, the estimation error is reduced of the residual component compared with process 2 of the method 3-1 [eq. (63)].

$$\hat{d}_x^i(x,y)=LPF[dx^i(x,y)], \text{ or } \hat{d}_x^i(x,y)=MED[dx^i(x,y)] \tag{116}$$

Thus, iterative estimation is terminated at the process 1 of the method 6-1 based on the method 3-1, or the process 4 of the method 6-2. Hence, final estimate is obtained from eq. (67), or eq. (111), or eq. (116).

The initial estimate [eq. (57)] of the iterative estimation of the 1D displacement component is set as zero if a priori data is not given about displacements of body motion nor applied compression. Alternatively, values accurately estimated at neighborhood can be used (high correlation or least squares).

[Method 6-4]

The flowchart of the method 6-4 is shown in FIG. 24. As example, let's consider measurement of 1D displacement component dx(x,y) in 2D ROI. At i th estimate (i≧11), the following process 1 is performed.

(Process 1: Estimation of the 1D Residual Displacement Component Distribution in 2D ROI)

Phase matching and estimation of the 1D residual displacement component are performed at every point (x,y) in the 2D ROI. That is, the process 1 of the method 3-1 is performed once at every point in the 2D ROI.

To obtain the estimate $\hat{u}_x^i(x,y)$ of the 1D residual component distribution $u_x^i(x,y)$ in the 2D ROI, at every point local 1D echo cross-spectrum [eq. (59)] is evaluated from the 1D Fourier's transforms of the pre-deformation local 1D ultrasound echo signal $r_1(l)$ and phase-matched post-deformation local 1D ultrasound echo signal $r'_2(l)$. Alternatively, when pre-deformation local 1D ultrasound echo signal is phase-matched, at every point cross-spectrum of $r'_1(l)$ and $r_2(l)$ is evaluated.

The least squares method is implemented on the gradient of the phase with utilization of each weight function, i.e., the squared cross-spectrum $|S_{2,1}^i(l)|^2$, where each weight function is normalized by the power of the cross-spectrum, i.e., $$\sum_l |S_{2,1}^i(l)|^2$$

[eq. (62)]. Moreover, regularization method is also implemented. That is, by minimizing the next functional with respect to the vector $u^i$ comprised of the 1D residual component distribution $u_x^i(x,y)$ in the 2D ROI.

$$\text{error}(u^i) = \|a - Fu^i\|^2 + \alpha_{1i}\|u^i\|^2 + \alpha_{2i}\|Gu^i\|^2 + \alpha_{3i}\|G^TGu^i\|^2 + \alpha_{4i}\|GG^TGu^i\|^2 \quad (117)$$

where a: vector comprised of (x,y) distribution of the cross-spectrum phase $\Theta^i(l)$ weighted with cross-spectrum $|S_{2,1}^i(l)|$ normalized by the magnitude of the cross-spectrum $$\sqrt{\sum_l |S_{2,1}^i(l)|^2}$$

evaluated at every point in the 2D ROI.

F: matrix comprised of (x,y) distribution of the Fourier's coordinate value l weighted with cross-spectrum $|S_{2,1}^i(l)|$ normalized by the magnitude of the cross-spectrum $$\sqrt{\sum_l |S_{2,1}^i(l)|^2}$$

evaluated at every point in the 2D ROI.

$\alpha_{1i}, \alpha_{2i}, \alpha_{3i}, \alpha_{4i}$: regularization parameter (at least larger than zero)

$Gu^i$: vector comprised of the finite difference approximations of the 2D distributions of the 2D gradient components of the unknown 1D residual component $u_x^i(x,y)$ $$\frac{\partial}{\partial x} u_x^i(x, y), \frac{\partial}{\partial y} u_x^i(x, y)$$

$G^TGu^i$: vector comprised of the finite difference approximations of the 2D distributions of the 2D Laplacian of the unknown 1D residual component $u^i(x,y)$ $$\frac{\partial^2}{\partial x^2} u_x^i(x, y) + \frac{\partial^2}{\partial y^2} u_x^i(x, y)$$

$GG^TGu^i$: vector comprised of the finite difference approximations of the 2D distributions of the 2D gradient components of the 2D Laplacians of the unknown 1D residual component $u_x^i(x,y)$ $$\frac{\partial}{\partial x}\left(\frac{\partial^2}{\partial x^2} u_x^i(x, y) + \frac{\partial^2}{\partial y^2} u_x^i(x, y)\right),$$
$$\frac{\partial}{\partial y}\left(\frac{\partial^2}{\partial x^2} u_x^i(x, y) + \frac{\partial^2}{\partial y^2} u_x^i(x, y)\right)$$

As $\|u^i\|^2$, $\|Gu^i\|^2$, $\|G^TGu^i\|^2$, $\|GG^TGu^i\|^2$ are positive definite, error($u^i$) has one minimum value. Thus, by solving for 1D residual displacement component distribution $u_x^i(x,y)$ in the 2D ROI the simultaneous equations:

$$(F^TF + \alpha_{1i}I + \alpha_{2i}G^TG + \alpha_{3i}G^TGG^TG + \alpha_{4i}G^TGG^TGG^T G)u^i = F^Ta, \quad (118)$$

estimate $\hat{u}_x^i(x,y)$ of the 1D residual component distribution $u_x^i(x,y)$ is stably obtained. Thus, estimation error is reduced of the residual component.

The regularization parameter of important information is set relatively large. Thus, the regularization parameters depend on the correlation of the local echo data (peak value of the cross-correlation function, sharpness of the cross-correlation function, width of the cross-correlation function), the SNR of the cross-spectrum power, etc.; then position of the unknown displacement component etc.

(Process 2: Update of the Estimate of the 1D Displacement Component Distribution)

The i-1 th estimate of the 1D displacement component distribution is updated using i th estimate of the 1D residual component distribution.

$$dx^i(x,y) = d_x^{i-1}(x,y) + \hat{u}_x^i(x,y) \quad (119)$$

Freely, this estimate can be 2D low pass filtered or 2D median filter to yield the estimate of the 1D displacement component distribution.

$$d_x^i(x,y) = LPF[dx^i(x,y)], \text{ or } d_x^i(x,y) = MED[dx^i(x,y)] \quad (120)$$

Hence, phase matching of the process 1 of method 6-4 is performed using the 1D residual component data $u_x^i(x,y)$ obtained from eq. (118), or the 1D component data $dx^i(x,y)$ obtained from eq. (119), or smoothed estimate obtained from eq. (120).

[Process 3: Condition for Heightening the Spatial Resolution of the 1D Displacement Component Distribution Measurement in 2D ROI (Condition for Making the Local Region Small)]

In order to make the spatial resolution high of the 1D displacement component distribution measurement, during iterative estimation, the local region used for each point is made small, or the local region used over the 2D ROI is made small.

The criteria for each point is below-described. The processes 1 and 2 of method 6-4 are iteratively carried out till the criteria is satisfied with. When the criteria is satisfied with, the local region is made small, for instance, the length of the local region is made half. For instance, the criteria is (121) or (121') with respect to threshold values Tratio or Tdiff.

$$\frac{\|\hat{u}_x^i(x, y)\|}{\|\hat{u}_x^{i-1}(x, y)\|} \leq Tratio \tag{121}$$

or $$\|\hat{u}_x^i(x, y) - \hat{u}_x^{i-1}(x, y)\| \leq Tdiff, \tag{121'}$$

where $\|\hat{u}_x^i(x,y)\|$ and $\|\hat{u}_x^{i-1}(x,y)\|$ are respectively norms (magnitudes) of the i th and i−1 th estimates of the residual components.

The criteria over the 2D ROI is below-described. The processes 1 and 2 of method 6-4 are iteratively carried out till the criteria is satisfied with. When the criteria is satisfied with, the local region is made small, for instance, the length of the local region is made half. For instance, the criteria is (122) or (122') with respect to threshold values Tratioroi or Tdiffroi.

$$\frac{\sum_{(x,y) \in ROI} \|\hat{u}_x^i(x, y)\|^2}{\sum_{(x,y) \in ROI} \|\hat{u}_x^{i-1}(x, y)\|^2} \leq Tratioroi \tag{122}$$

or $$\sum_{(x,y) \in ROI} \|\hat{u}_x^i(x, y) - \hat{u}_x^{i-1}(x, y)\| \leq Tdiffroi, \tag{122'}$$

where $\|\hat{u}_x^i(x,y)\|$ and $\|\hat{u}_x^{i-1}(x,y)\|$ are respectively norms (magnitudes) of the i th and i−1 th estimates of the residual components.

(Process 4: Condition for Terminating the Iterative Estimation of the 1D Displacement Component Distribution in 2D ROI)

Below-described is the criteria for terminating the iterative estimation of the 1D displacement component distribution. The processes 1, 2 and 3 of method 6-4 are iteratively carried out till the criteria is satisfied with. For instance, the criteria is (123) or (123') with respect to threshold values aboveTratioroi or aboveTdiffroi.

$$\frac{\sum_{(x,y) \in ROI} \|\hat{u}_x^i(x, y)\|^2}{\sum_{(x,y) \in ROI} \|\hat{u}_x^{i-1}(x, y)\|^2} \leq aboveTratioroi \tag{123}$$

or $$\sum_{(x,y) \in ROI} \|\hat{u}_x^i(x, y) - \hat{u}_x^{i-1}(x, y)\| \leq aboveTdiffroi, \tag{123'}$$

where $\|\hat{u}_x^i(x,y)\|$ and $\|\hat{u}_x^{i-1}(x,y)\|$ are respectively norms (magnitudes) of the i th and i−1 th estimates of the residual components.

Final estimate is obtained from eq. (119) or eq. (120).

The initial estimate [eq. (57)] of the iterative estimation of the 1D displacement component is set as zero if a priori data is not given about displacements of body motion nor applied compression. Alternatively, values accurately estimated at neighborhood can be used (high correlation or least squares).

[Method 6-5]

The flowchart of the method 6-5 is shown in FIG. 25. As example, let's consider measurement of 1D displacement component dx(x,y) in 2D ROI.

Possibility of divergence is detected from above-described condition (70) or (70') in above-described process 1 of the method 6-4, and by effectively utilizing the method 6-1 based on the method 3-1, even if the SNR of the ultrasound echo signals are low, accurate 1D displacement component measurement can be realized.

At first, the procedure of iterative estimation is same as that of the method 6-4 (Processes 1, 2, 3, and 4). At i th estimate, the following processes are performed.

The process 1 of the method 6-4 is performed. (Phase matching and estimation of the 1D residual displacement component are performed at every point (x,y) in the 2D ROI.) That is, the process 1 of the method 3-1 is performed once at every point in the 2D ROI. Moreover, using the regularization method, stably the estimate of the 1D residual component distribution is obtained.

i−1 th estimate $\hat{d}_x^{i-1}(x,y)$ of 1D displacement component distribution dx(x,y).

i th estimate $\hat{u}_x^i(x,y)$ of 1D residual component distribution $u_x^i(x,y)$.

During this estimation, if neither condition (70) nor (70') is satisfied with, the method 6-1 based on the method 3-1 is used. If condition (70) or (70') is satisfied with at points or regions, in the process 2 of the method 6-4, over sufficiently large regions centered on the points or regions, or over the 2D ROI, the estimate $dx^i(x,y)$ of the 1D displacement component dx(x,y) can be 2D low pass filtered or 2D median filtered as eq. (124).

$$\hat{d}_x^i(x,y)=LPF[dx^i(x,y)], \text{ or } \hat{d}_x^i(x,y)=MED[dx^i(x,y)] \tag{124}$$

Thus, the estimation error is reduced of the residual component.

Iterative estimation is terminated at the process 1 of the method 6-1 based on the method 3-1, or the process 4 of the method 6-4. Hence, final estimate is obtained from eq. (67), or eq. (119), or eq. (124).

The initial estimate [eq. (57)] of the iterative estimation of the 1D displacement component is set as zero if a priori data is not given about displacements of body motion nor applied compression. Alternatively, values accurately estimated at neighborhood can be used (high correlation or least squares).

In the 3D SOI, the 3D displacement vector distribution can also be measured using method 4 or method 5 by changing the adapted direction. In the 2D ROI, the 2D displacement vector distribution can also be measured using method 6 by changing the adapted direction. Except for threshold value for terminating the iterative estimation, other threshold values can be updated. Estimate can also be performed non-iteratively.

When applying the regularization method, in addition to the magnitude of the unknown displacement vector, spatial continuity and differentiability of the unknown displacement vector distribution, mechanical properties of tissue (e.g., incompressibility), and compatibility conditions of displacement vector distribution and displacement component distribution, as the a priori knowledge, used is temporal continuity and differentiability of the unknown series of the displacement vector distribution and displacement component distribution. The regularization parameter depends on time-space dimension number, direction of the unknown displacement component, position of the unknown displacement vector, time, etc.

Thus, as the displacement vector can be measured accurately, consequently, in addition to 3D strain tensor, accurately measured can be 2D strain tensor, one strain component, 3D strain rate tensor, 2D strain rate tensor, one strain rate component, acceleration vector, velocity vector, etc.

(VII) Differential Filter

The strain tensor components can be obtained by spatial differential filtering with suitable cut off frequency in time domain or frequency domain the measured 3D, or 2D displacement vector components, or measured 1D direction displacement component in the 3D, 2D, or 1D ROI. The strain rate tensor components, acceleration vector components, or velocity vector components can be obtained by time differential filtering with suitable cut off frequency in time domain or frequency domain the measured time series of displacement components, or strain components. The strain rate tensor components can be obtained from the strain tensor components directly measured by below-described signal processing.

As above described, when measuring displacement from the gradient of the echo cross-spectrum phase, to result the more accurate measurement accuracy, the least squares method can be applied with utilization as the weight function of the squares of the cross-spectrum usually normalized by the cross-spectrum power, where, to stabilize the measurement, the regularization method can be applied, by which a priori information can be incorporated, i.e., about within the ROI the magnitude of the unknown displacement vector, spatial continuity and differentiability of the unknown displacement vector distribution etc.

Next, as the estimation methods of the displacements during the iterative estimation to update 3D, 2D, 1D displacement component, in order to reduce calculation amount and shorten calculation time, other methods are also described. These estimation methods can be used in combination, or one of them can be used. To realize real-time measurement, the estimate can also be performed non-iteratively.

In order to reduce calculation amount and shorten calculation time, calculation process is simplified. That is, as the cross-spectrum phase $\theta(\omega x, \omega y, \omega z)$ is represented as $\theta_2(\omega x, \omega y, \omega z) - \theta_1(\omega x, \omega y, \omega z)$ using the phases $\theta_1(\omega x, \omega y, \omega z)$ and $\theta_2(\omega x, \omega y, \omega z)$ respectively obtained from 3D Fourier's transforms $R_1(\omega x, \omega y, \omega z)$ and $R_2(\omega x, \omega y, \omega z)$ of the local echo signals under pre- and post-deformation, the displacement vector $u(=(ux,uy,uz)^T)$ is represented as $$\begin{pmatrix} ux \\ uy \\ uz \end{pmatrix} = \frac{grad\,(arg\,[R_2^*(\omega x, \omega y, \omega z) R_1(\omega x, \omega y, \omega z)])}{(where\ grad = (d/d\omega x, d/d\omega y, d/d\omega z)^T)}$$

$$= \begin{pmatrix} \frac{d}{d\omega x}\theta(\omega x, \omega y, \omega z) \\ \frac{d}{d\omega y}\theta(\omega x, \omega y, \omega z) \\ \frac{d}{d\omega z}\theta(\omega x, \omega y, \omega z) \end{pmatrix}$$

$$= \begin{pmatrix} \frac{d}{d\omega x}(\theta_1(\omega x, \omega y, \omega z) - \theta_2(\omega x, \omega y, \omega z)) \\ \frac{d}{d\omega y}(\theta_1(\omega x, \omega y, \omega z) - \theta_2(\omega x, \omega y, \omega z)) \\ \frac{d}{d\omega z}(\theta_1(\omega x, \omega y, \omega z) - \theta_2(\omega x, \omega y, \omega z)) \end{pmatrix}$$

$$= \mathrm{Im}\,[grad\,(\ln\{R_2^*(\omega x, \omega y, \omega z) R_1(\omega x, \omega y, \omega z)\})]$$

$$= \begin{pmatrix} \frac{\mathrm{Re}\,[R_2(\omega x, \omega y, \omega z)]\frac{d}{d\omega x}\mathrm{Im}\,[R_2(\omega x, \omega y, \omega z)] - \frac{d}{d\omega x}\mathrm{Re}\,[R_2(\omega x, \omega y, \omega z)]\mathrm{Im}\,[R_2(\omega x, \omega y, \omega z)]}{|R_2(\omega x, \omega y, \omega z)|^2} \\ + \frac{\mathrm{Re}\,[R_1(\omega x, \omega y, \omega z)]\frac{d}{d\omega x}\mathrm{Im}\,[R_1(\omega x, \omega y, \omega z)] - \frac{d}{d\omega x}\mathrm{Re}\,[R_1(\omega x, \omega y, \omega z)]\mathrm{Im}\,[R_1(\omega x, \omega y, \omega z)]}{|R_1(\omega x, \omega y, \omega z)|^2} \\ - \frac{\mathrm{Re}\,[R_2(\omega x, \omega y, \omega z)]\frac{d}{d\omega y}\mathrm{Im}\,[R_2(\omega x, \omega y, \omega z)] - \frac{d}{d\omega y}\mathrm{Re}\,[R_2(\omega x, \omega y, \omega z)]\mathrm{Im}\,[R_2(\omega x, \omega y, \omega z)]}{|R_2(\omega x, \omega y, \omega z)|^2} \\ + \frac{\mathrm{Re}\,[R_1(\omega x, \omega y, \omega z)]\frac{d}{d\omega y}\mathrm{Im}\,[R_1(\omega x, \omega y, \omega z)] - \frac{d}{d\omega y}\mathrm{Re}\,[R_1(\omega x, \omega y, \omega z)]\mathrm{Im}\,[R_1(\omega x, \omega y, \omega z)]}{|R_1(\omega x, \omega y, \omega z)|^2} \\ - \frac{\mathrm{Re}\,[R_2(\omega x, \omega y, \omega z)]\frac{d}{d\omega z}\mathrm{Im}\,[R_2(\omega x, \omega y, \omega z)] - \frac{d}{d\omega z}\mathrm{Re}\,[R_2(\omega x, \omega y, \omega z)]\mathrm{Im}\,[R_2(\omega x, \omega y, \omega z)]}{|R_2(\omega x, \omega y, \omega z)|^2} \\ + \frac{\mathrm{Re}\,[R_1(\omega x, \omega y, \omega z)]\frac{d}{d\omega z}\mathrm{Im}\,[R_1(\omega x, \omega y, \omega z)] - \frac{d}{d\omega z}\mathrm{Re}\,[R_1(\omega x, \omega y, \omega z)]\mathrm{Im}\,[R_1(\omega x, \omega y, \omega z)]}{|R_1(\omega x, \omega y, \omega z)|^2} \end{pmatrix}$$

Then, using the phases of the high SNR frequency the displacement vector u can be obtained by partial differentiating in the frequency directions $\omega x$, $\omega y$, $\omega z$ the difference between the phases $\theta_2(\omega x,\omega y,\omega z)$ and $\theta_1(\omega x,\omega y,\omega z)$, or by calculating the difference between partial differentiations in the frequency directions $\omega x$, $\omega y$, $\omega z$ of the phases $\theta_2(\omega x,\omega y,\omega z)$ and $\theta_1(\omega x,\omega y,\omega z)$, or by using Fourier's transform values $\mathrm{Re}[R_2(\omega x,\omega y,\omega z)]$, $\mathrm{Im}[R_2(\omega x,\omega y,\omega z)]$, $\mathrm{Re}[R_1(\omega x,\omega y,\omega z)]$, $\mathrm{Im}[R_1(\omega x,\omega y,\omega z)]$, and their partial derivatives in the frequency directions $\omega x$, $\omega y$, $\omega z$ without unwrapping the phase. These partial derivatives can be obtained by finite-difference approximating or differential filtering. Freely, the phases, the signal components, or numerator and denominator can be moving averaged or low-pass filtered in the frequency domain. The final estimate can be the mean vector calculated from the displacement data obtained at high SNR frequencies.

The 2D displacement vector and one direction displacement component can respectively be obtained in a similar way by calculating 2D and 1D Fourier's transforms.

The simultaneous equations of the above-described equation can be solved in the frequency domain, or spatial and temporal simultaneous equations of the above-described equation can be handled, where above-described regularization method can be applied.

When performing 1D (one direction) calculation, in order to reduce calculation amount and shorten calculation time, calculation process is simplified. That is, for instance, when performing x direction calculation, as the cross-spectrum phase $\theta(\omega x,\omega y,\omega z)$ is represented as $\theta(\omega x)=ux\cdot\omega x$, the displacement is obtained form the phase of the high SNR frequency (y direction calculation; $\theta(\omega y)=uy\cdot\omega y$, z direction calculation; $\theta(\omega z)=uz\cdot\omega z$). The final estimate can be the mean value calculated from the displacement data obtained at high SNR frequencies.

When large displacement needs to be handled, before estimating the gradient of the cross-spectrum phase, the phase was unwrapped, or the displacement was coarsely estimated by cross-correlation method. Thus, measurement procedure had become complex one. Otherwise, to cope with these complexity, the measurement procedure is made simpler without these processes by introducing process of thinning out data and remaking data interval original.

The simultaneous equations of the above-described equation can be solved in the frequency domain, or spatial and temporal simultaneous equations of the above-described equation can be handled, where above-described regularization method can be applied.

Otherwise, echo signals are acquired at two different time, freely, the aouto-correlation method (beam direction or scan direction) and the regularization method can be equipped.

Otherwise, freely, ultrasound Doppler's method can be equipped. The Doppler's shift can be detected in beam direction or scan direction.

There are many methods for detecting the Doppler's shift. From the phase distribution $\theta_{ZR}(x,y,z,t)=\tan^{-1}(\mathrm{Im}[Z_R(x,y,z,t)]/\mathrm{Re}[Z_R(x,y,z,t)])$ of the quadrate demodulation signal $Z_R(x,y,z,t)(=\mathrm{Re}[Z_R(x,y,z,t)]+j\mathrm{Im}[Z_R(x,y,z,t)]$ in R axis direction acquired at each position (x,y,z) in the ROI, for instance, the velocity component vx in x axis direction (R=x) at time t=T and at position (X,Y,Z) can be obtained as $$vx = -\frac{1}{s_x\pi}\frac{d}{dt}\left[\frac{c_x}{f_{0x}}\tan^{-1}\left(\frac{\mathrm{Im}\,[Zx(x,y,z,t)]}{\mathrm{Re}\,[Zx(x,y,z,t)]}\right)\right]\bigg|_{x=X,y=Y,z=Z,t=T}$$

$$= -\frac{1}{s_x\pi}\left|\frac{c_x}{f_{0x}}\frac{\mathrm{Re}\,[Zx(x,y,z,t)]\cdot\frac{d}{dt}[\mathrm{Im}\,[Zx(x,,y,z,t)]]-\frac{d}{dt}[\mathrm{Re}\,[Zx(x,y,z,t)]]\cdot\mathrm{Im}\,[Zx(x,y,z,t)]}{\mathrm{Re}\,[Zx(x,y,z,t)]^2+\mathrm{Im}\,[Zx(x,y,z,t)]^2}\right|_{x=X,y=Y,z=Z,t=T}$$

$c_R$ is the ultrasound propagating velocity and scan velocity respectively when R axis is beam axis and scan axis. $f_{0R}$ is ultrasound carrier frequency and sine frequency respectively when R axis is beam axis and scan axis. $S_R$ is 4.0 and 2.0 respectively when R axis is beam axis and scan axis. As above-described, temporal gradient of the phase $\theta_{ZR}(x,y,z,t)$ can also be obtained by finite difference approximating or differential filtering after obtaining the phase $\theta_{ZR}(x,y,z,t)$. Freely, the phases, the signal components, or numerator and denominator can be moving averaged or low-pass filtered in the time domain. Thus, the velocity component distributions (series) can be obtained in the ROI.

The spatial and temporal simultaneous equations of the above-described equation can be handled, where above-described regularization method can be applied.

By multiplying pulse transmitting interval Ts to each velocity component distributions (series), the displacement component distribution (series) can be obtained. Alternatively, by integrating the velocity vector component distributions (series), the displacement vector distribution (series) can be obtained.

From temporal spatial derivatives of these velocity vector component distributions (series) or displacement vector component distributions (series), obtained are strain tensor component distributions (series), acceleration vector component distributions (series), and strain rate tensor component distributions (series).

Otherwise, freely, a method for directly obtaining strain tensor components can be equipped, i.e., from spatial partial derivative of the phase of the quadrate demodulate signal (beam direction or scan direction) of the ultrasound echo signals.

From the phase distribution $\theta_{ZR}(x,y,z,t)=\tan^{-1}(\mathrm{Im}[Z_R(x,y,z,t)]/\mathrm{Re}[Z_R(x,y,z,t)])$ of the quadrate demodulation signal $Z_R(x,y,z,t)(=\mathrm{Re}[Z_R(x,y,z,t)]+j\mathrm{Im}[Z_R(x,y,z,t)]$ in R axis direction acquired at each position (x,y,z) in the ROI, for instance, the normal strain component $\epsilon xx$ in x axis direction (R=x) at time t=T and at position (X,Y,Z) can be obtained as $$\epsilon xx_{(X,Y,Z,T)} = \frac{\partial}{\partial x}u_x(x,y,z,t)\big|_{x=X,y=Y,z=Z,t=T}$$

$$= -\frac{1}{s_x\pi}\frac{d}{dx}\frac{d}{dt}\left[\frac{\frac{c_x}{f_{0x}}\tan^{-1}}{\left(\frac{\mathrm{Im}\,[Zx(x,y,z,t)]}{\mathrm{Re}\,[Zx(x,y,z,t)]}\right)}\right]\bigg|_{\substack{x=X,y=Y,\\z=Z,t=T}}Ts$$

$$= -\frac{1}{s_x\pi}\frac{d}{dt}\left|\frac{c_x}{f_{0x}}\frac{\mathrm{Re}\left[\begin{array}{c}Zx\\(x,y,z,t)\end{array}\right]\cdot\frac{d}{dx}\left[\mathrm{Im}\left[\begin{array}{c}Zx\\(x,y,z,t)\end{array}\right]\right]-\frac{d}{dx}[\mathrm{Re}\,[Zx(x,y,z,t)]]\cdot\mathrm{Im}\left[\begin{array}{c}Zx\\(x,y,z,t)\end{array}\right]}{\mathrm{Re}\,[Zx(x,y,z,t)]^2+\mathrm{Im}\,[Zx(x,y,z,t)]^2}\right|_{\substack{x=X,y=Y,\\z=Z,t=T}}Ts$$

$$= -\frac{1}{s_x\pi}\frac{d}{dx}\left|\frac{c_x}{f_{0x}}\frac{\mathrm{Re}\,[Zx(x,y,z,t)]\cdot\frac{d}{dt}\left[\mathrm{Im}\left[\begin{array}{c}Zx\\(x,y,z,t)\end{array}\right]\right]-\frac{d}{dt}[\mathrm{Re}\,[Zx(x,y,z,t)]]\cdot\mathrm{Im}\left[\begin{array}{c}Zx\\(x,y,z,t)\end{array}\right]}{\mathrm{Re}\,[Zx(x,y,z,t)]^2+\mathrm{Im}\,[Zx(x,y,z,t)]^2}\right|_{\substack{x=X,y=Y,\\z=Z,t=T}}Ts$$

$c_R$ is the ultrasound propagating velocity and scan velocity respectively when R axis is beam axis and scan axis. $f_{0R}$ is ultrasound carrier frequency and sine frequency respectively when R axis is beam axis and scan axis. $S_R$ is 4.0 and 2.0 respectively when R axis is beam axis and scan axis. As above-described, spatial gradient of the phase $\theta_{ZR}(x,y,z,t)$ can also be obtained by finite difference approximating or differential filtering after obtaining the phase $\theta_{ZR}(x,y,z,t)$. Freely, the phases, the signal components, or numerator and denominator can be moving averaged or low-pass filtered in the space domain. For instance, the shear strain component εxy in x-y plane (R=x and y) at time t=T and at position (X,Y,Z) can be obtained as $$\begin{aligned}\frac{\varepsilon xy}{(X,Y,Z,T)} &= \frac{1}{2}\left(\frac{\partial}{\partial x}uy(x,y,z,t) + \frac{\partial}{\partial y}ux(x,y,z,t)\right)\bigg|_{\substack{x=X,y=Y,\\z=Z,t=T}}\\
&= \frac{1}{2}\left(\begin{array}{c}-\frac{1}{s_y\pi}\frac{d}{dx}\frac{d}{dt}\left[\frac{c_y}{f_{0y}}\tan^{-1}\left(\frac{\operatorname{Im}[Zy(x,y,z,t)]}{\operatorname{Re}[Zy(x,y,z,t)]}\right)\right]-\\ \frac{1}{s_x\pi}\frac{d}{dy}\frac{d}{dt}\left[\frac{c_x}{f_{0x}}\tan^{-1}\left(\frac{\operatorname{Im}[Zx(x,y,z,t)]}{\operatorname{Re}[Zx(x,y,z,t)]}\right)\right]\end{array}\right)\bigg|_{\substack{x=X,y=Y,\\z=Z,t=T}} Ts\\
&= \frac{1}{2}\left(-\frac{1}{s_y\pi}\frac{d}{dt}\left(\frac{c_y}{f_{0y}}\frac{\operatorname{Re}[Zy(x,y,z,t)]\cdot\frac{d}{dy}[\operatorname{Im}[Zx(x,,y,z,t)]] - \frac{d}{dy}\left[\frac{\operatorname{Re}}{[Zx(x,y,z,t)]}\right]\cdot\operatorname{Im}[Zx(x,y,z,t)]}{\operatorname{Re}[Zy(x,y,z,t)]^2 + \operatorname{Im}[Zy(x,y,z,t)]^2}\right)-\right.\\
&\qquad\left.\frac{1}{s_x\pi}\frac{d}{dt}\left(\frac{c_x}{f_{0x}}\frac{\operatorname{Re}[Zx(x,y,z,t)]\cdot\frac{d}{dy}\left[\frac{\operatorname{Im}}{[Zx(x,,y,z,t)]}\right]-\frac{d}{dy}\left[\frac{\operatorname{Re}}{[Zx(x,y,z,t)]}\right]\cdot\operatorname{Im}[Zx(x,y,z,t)]}{\operatorname{Re}[Zx(x,y,z,t)]^2+\operatorname{Im}[Zx(x,y,z,t)]^2}\right)\right) Ts\\
&= \frac{1}{2}\left(-\frac{1}{s_y\pi}\frac{d}{dx}\left(\frac{c_y}{f_{0y}}\frac{\operatorname{Re}[Zy(x,y,z,t)]\cdot\frac{d}{dt}[\operatorname{Im}[Zy(x,y,z,t)]]-\frac{d}{dt}[\operatorname{Re}[Zy(x,y,z,t)]]\cdot\operatorname{Im}[Zy(x,y,z,t)]}{\operatorname{Re}\left[\frac{Zy}{(x,y,z,t)}\right]^2+\operatorname{Im}\left[\frac{Zy}{(x,y,z,t)}\right]^2}\right)-\right.\\
&\qquad\left.\frac{1}{s_x\pi}\frac{d}{dy}\left(\frac{c_x}{f_{0x}}\frac{\operatorname{Re}\left[\frac{Zx}{(x,y,z,t)}\right]\cdot\frac{d}{dt}\left[\frac{\operatorname{Im}}{[Zx(x,,y,z,t)]}\right]-\frac{d}{dt}\left[\frac{\operatorname{Re}}{[Zx(x,y,z,t)]}\right]\cdot\operatorname{Im}\left[\frac{Zx}{(x,y,z,t)}\right]}{\operatorname{Re}\left[\frac{Zx}{(x,y,z,t)}\right]^2+\operatorname{Im}\left[\frac{Zx}{(x,y,z,t)}\right]^2}\right)\right)\bigg|_{\substack{x=X,y=Y,\\z=Z,t=T}} Ts\end{aligned}$$

Thus, the strain component distributions (series) can be obtained in the ROI.

The spatial and temporal simultaneous equations of the above-described equation can be handled, where above-described regularization method can be applied.

By integrating the partial derivatives of displacement vector component distributions (series), the displacement vector distribution (series) can be obtained.

From temporal spatial derivatives of these strain tensor component distributions (series) or displacement vector component distributions (series), obtained are strain rate tensor component distributions (series), and acceleration vector component distributions (series).

Freely, (I-1) complex cross-correlation method (phase in beam direction or scan direction of complex cross-correlation function signal obtained from complex analytic signals or quadrate detection signals, or obtained from cross-correlation of ultrasound echo signals) is utilized, or (I-2) both of complex cross-correlation method (beam direction or scan direction) and the regularization method are utilized, or (I-3) at least 2D distribution (including beam direction or not) of the phase of 3D, or 2D complex cross-correlation function signals or 1D complex cross-correlation function signal respectively obtained from 3D complex signals with single-octant spectra, 2D complex signals with single-quadrant spectra, and conventional 1D complex analytic signal (S. L. Hahn, "Multidimensional complex signals with single-orthant spectra," Proceedings of the IEEE, vol. 80, no. 8, pp. 1287-1300, 1992, where the 3D and 2D complex signals are not proven to be analytic in the formal sense. Then, according to the paper, we corrected the terms.) and the regularization method are utilized. That is, methods (I-1), (I-2), and (I-3) can be equipped.

On the method (I-3), for instance, the next equation holds for unknown 3D displacement vector $(ux, uy, uz)^T$ at each point (X,Y,Z) at time t=T:

$$\theta_{cc}(0,0,0) + \frac{\partial}{\partial x}\theta_{cc}(x,y,z)\bigg|_{x=0,y=0,z=0} ux + \frac{\partial}{\partial y}\theta_{cc}(x,y,z)\bigg|_{x=0,y=0,z=0} uy + \frac{\partial}{\partial z}\theta_{cc}(x,y,z)\bigg|_{x=0,y=0,z=0} uz = 0.$$

$\theta_{cc}(X,Y,Z;x,y,z)$ is the 3D phase distribution (x,y,z) of the complex cross-correlation function Cc(X,Y,Z;x,y,z) of the point (X,Y,Z) evaluated from rf echo signals with respect to transmitted ultrasound pulses at the time t=T and t=T+ΔT:

$\theta_{cc}(X,Y,Z;x,y,z) = \tan^{-1}(Im[Cc(X,Y,Z;x,y,z)]/Re[Cc(X,Y,Z;x,y,z)])$, where the coordinate (x,y,z) has the origin at (X,Y,Z). In the SOI, occasionally also in time direction, these equations hold (simultaneous equations), and can be solved by least squared method, where, freely, regularization method can be applied (the temporal and spatial magnitude of the unknown displacement vector distribution, temporal and spatial continuity and differentiability of the unknown displacement vector distribution). Thus, the displacement vector distribution (series) can be obtained. The gradients of the phase $\theta_{cc}(X,Y,Z;x,y,z)$ can be obtained by finite difference approximating or differential filtering. However, for instance, x partial derivative $\partial/\partial x \cdot \theta_{cc}(x,y,z)|_{x=0,y=0,z=0}$ can be obtained as:

{Re[Cc(X,Y,Z;0,0,0)]×∂/∂x·Im[Cc(X,Y,Z;x,y,z)]|_{x=0,y=0,z=0} − ∂/∂x·Re[Cc(X,Y,Z;x,y,z)]|_{x=0,y=0,z=0}×Im[Cc(X,Y,Z;0,0,0)]}/{Re[Cc(X,Y,Z;0,0,0)]²+Im[Cc(X,Y,Z;0,0,0)]²}.

$\partial/\partial x \cdot \text{Re}[Cc(X,Y,Z;x,y,z)]|_{x=0,y=0,z=0}$ can be obtained by finite difference approximating or differential filtering. Freely, the phases, the signal components, or numerator and denominator can be moving averaged or low-pass filtered in the time domain.

For instance, the next equation holds for unknown 2D displacement vector $(ux,uy)^T$ at each point $(X,Y,Z)$ at time $t=T$:

$$\theta_{cc}(0,0) + \frac{\partial}{\partial x}\theta_{cc}(x,y)\bigg|_{x=0,y=0} ux + \frac{\partial}{\partial y}\theta_{cc}(x,y)\bigg|_{x=0,y=0} uy = 0.$$

$\theta_{cc}(X,Y,Z;x,y)$ is the 2D phase distribution $(x,y)$ of the complex cross-correlation function $Cc(X,Y,Z;x,y)$ of the point $(X,Y,Z)$ evaluated from rf echo signals with respect to transmitted ultrasound pulses at the time $t=T$ and $t=T+\Delta T$. Method (I-3) can also be applied to measurement of one displacement component distribution.

On the method (I-1), utilized is phase of complex cross-correlation function signal in beam direction or scan direction. The next equation holds for unknown displacement component $ux$ at each point $(X,Y,Z)$ at time $t=T$ (the auto-correlation function method's equation):

$$\theta_{cc}(0) + \frac{d}{dx}\theta_{cc}(x)\bigg|_{x=0} ux = 0.$$

$\theta_{cc}(X,Y,Z;x)$ is the 1D phase distribution $(x)$ of the complex cross-correlation function $Cc(X,Y,Z;x)$ of the point $(X,Y,Z)$ evaluated from rf echo signals with respect to transmitted ultrasound pulses at the time $t=T$ and $t=T+\Delta T$.

In the ROI, by solving this equation for unknown displacement component $ux$ at each point, the displacement component distribution (series) can be obtained.

On the method (I-2), in the ROI, occasionally also in time direction, this equation holds in beam direction or scan direction, and the derived simultaneous equations can be solved by least squared method, where, freely, regularization method can be applied (the temporal and spatial magnitude of the unknown displacement component distribution, temporal and spatial continuity and differentiability of the unknown displacement component distribution). Thus, the displacement component distribution (series) can be obtained.

On the methods (I-3) and (I-2), occasionally the unknown displacement vector and the unknown displacement component are dealt as locally uniform ones. That is, occasionally, under the assumption that the local region uniformly moves, the simultaneous equations hold for the unknown local displacement vector or the unknown local displacement component. Otherwise, occasionally, the simultaneous equations hold under the assumption that the displacement is uniform for temporal finite interval. Thus, the spatial distribution (series) can be obtained.

The next method can be equipped. That is, the strain tensor component can be directly obtained from spatial derivative of the no time delay phase $\theta_{cc}(x,y,z;0,0,0) = \tan^{-1}(\text{Im}[Cc(x,y,z;0,0,0)]/\text{Re}[Cc(x,y,z;0,0,0)])$ of the 3D complex cross-correlation function, of the no time delay phase $\theta_{cc}(x,y,z;0,0) = \tan^{-1}(\text{Im}[Cc(x,y,z;0,0)]/\text{Re}[Cc(x,y,z;0,0)])$ of the 2D complex cross-correlation function (including beam direction or not), or of the no time delay phase $\theta_{cc}(x,y,z;0) = \tan^{-1}(\text{Im}[Cc(x,y,z;0)]/\text{Re}[Cc(x,y,z;0)])$ of the 1D complex cross-correlation function (beam direction or scan direction) of the point $(x,y,z)$ evaluated from rf echo signals with respect to transmitted ultrasound pulses at the time $t=T$ and $t=T+\Delta T$.

For instance, the normal strain component $\epsilon xx$ in x axis direction $(R=x)$ at time $t=T$ and at position $(X,Y,Z)$ can be obtained as:

$$\begin{aligned}\epsilon xx\\(X,Y,Z,T)\end{aligned} = \frac{\partial}{\partial x}u_x(x,y,z,t)\bigg|_{x=X,y=Y,z=Z,t=T}$$

$$= \frac{1}{s_R\pi}\frac{d}{dx}\left[\frac{c_x}{f_{0_x}}\theta_{cc}(x,y,z,t)\right]\bigg|_{x=X,y=Y,z=Z,t=T}$$

$$= \frac{1}{s_R\pi}\frac{c_x}{f_{0_x}}\left(\frac{\text{Re}[Cc(x,y,z,t)] \cdot \frac{d}{dx}[\text{Im}[Cc(x,y,z,t)]] - \frac{d}{dx}[\text{Re}[Cc(x,y,z,t)]] \cdot \text{Im}[Cc(x,y,z,t)]}{\text{Re}[Cc(x,y,z,t)]^2 + \text{Im}[Cc(x,y,z,t)]^2}\right)\bigg|_{x=X,y=Y,z=Z,t=T}$$

$c_R$ is the ultrasound propagating velocity and scan velocity respectively when R axis is beam axis and scan axis. $f_{0R}$ is ultrasound carrier frequency and sine frequency respectively when R axis is beam axis and scan axis. $S_R$ is 4.0 and 2.0 respectively when R axis is beam axis and scan axis. As above-described, spatial gradient of the phase $\theta_{cc}(x,y,z,t)$ can also be obtained by finite difference approximating or differential filtering after obtaining the phase $\theta_{cc}(x,y,z,t)$. Freely, the phases, the signal components, or numerator and denominator can be moving averaged or low-pass filtered in the space domain. Thus, the strain component distributions (series) can be obtained in the ROI.

The spatial and temporal simultaneous equations of the above-described equation can be handled, where above-described regularization method can be applied.

By integrating the partial derivatives of displacement vector component distributions (series), the displacement vector distribution (series) can be obtained.

From temporal spatial derivatives of these strain tensor component distributions (series) or displacement vector component distributions (series), obtained are strain rate tensor component distributions (series), and acceleration vector component distributions (series).

Freely, (II-1) complex analytic signal method (beam direction or scan direction) is utilized, or (II-2) both of complex analytic signal method (beam direction or scan direction) and the regularization method are utilized, or (II-3) at least 2D distribution (including beam direction or not) of the 3D, 2D phases, or 1D phase of respective of 3D complex signals with single-octant spectra, 2D complex signals with single-quadrant spectra, and conventional 1D complex analytic signal and the regularization method are utilized (Optical flow algorithm is applied to the phase of the complex signal.). That is, methods (II-1), (II-2), and (II-3) can be equipped.

On the method (II-3), for instance, the next equation holds for unknown 3D displacement vector $(ux,uy,uz)^T$ at each point $(X,Y,Z)$ at time $t=T$:

$$\frac{d}{dx}\theta_A(x,y,z,t)\bigg|_{x=X,y=Y,z=Z,t=T}$$

$$ux + \frac{d}{dy}\theta_A(x,y,z,t)\bigg|_{x=X,y=Y,z=Z,t=T} uy + \frac{d}{dz}\theta_A(x,y,z,t)\bigg|_{x=X,y=Y,z=Z,t=T}$$

-continued $$uz + \frac{d}{dt}\theta_A(x, y, z, t)\bigg|_{x=X,y=Y,z=Z,t=T} \Delta t = 0$$

(or for unknown 3D velocity vector $(vx,vy,vz)^T$:

$$\frac{d}{dx}\theta_A(x, y, z, t)\bigg|_{x=X,y=Y,z=Z,t=T} vx + \frac{d}{dy}\theta_A(x, y, z, t)\bigg|_{x=X,y=Y,z=Z,t=T}$$

$$vy + \frac{d}{dz}\theta_A(x, y, z, t)\bigg|_{x=X,y=Y,z=Z,t=T}$$

$$vz + \frac{d}{dt}\theta_A(x, y, z, t)\bigg|_{x=X,y=Y,z=Z,t=T} = 0).$$

$\theta_A(x,y,z,t)$ is the 3D phase distribution (x,y,z) of the complex signal A(x,y,z,t) (=Re[A(x,y,z,t)]+jIm[A(x,y,z,t)] of the point (x,y,z) at the time t ($\Delta t$: transmitted pulse interval):

$$\theta_A(x,y,z,t)=\tan^{-1}(Im[A(x,y,z,t)]/Re[A(x,y,z,t)]).$$

In the SOI, occasionally also in time direction, these equations hold (simultaneous equations), and can be solved by least squared method, where, freely, regularization method can be applied [the temporal and spatial magnitude of the unknown displacement (velocity) vector distribution, temporal and spatial continuity and differentiability of the unknown displacement (velocity) vector distribution]. Thus, the displacement (velocity) vector distribution (series) can be obtained. The temporal and spatial gradients of the phase $\theta_A(x,y,z,t)$ can be obtained by finite difference approximating or differential filtering. However, for instance, x partial derivative $\partial/\partial x \cdot \theta_A(x,y,z,t)|_{x=X,y=Y,z=Z,t=T}$ can be obtained as $\{Re[A(X,Y,Z,T)] \times \partial/\partial x \cdot Im[A(x,y,z,t)]|_{x=X,y=Y,z=Z,t=T} - \partial/\partial x \cdot Re[A(x,y,z,t)]|_{x=X,y=Y,z=Z,t=T} \times Im[A(X,Y,Z,T)]\}/\{Re[A(X,Y,Z;T)]^2 + Im[A(X,Y,Z,T)]^2\}$.

$\partial/\partial x \cdot Re[A(x,y,z,t)]|_{x=X,y=Y,z=Z,t=T}$ can be obtained by finite difference approximating or differential filtering. Freely, the phases, the signal components, or numerator and denominator can be moving averaged or low-pass filtered in the time domain.

For instance, the next equation holds for unknown 2D displacement vector $(ux,uy)^T$ at each point (X,Y,Z) at time t=T:

$$\frac{d}{dx}\theta_A(x, y, t)\bigg|_{x=X,y=Y,t=T} ux + \frac{d}{dy}\theta_A(x, y, t)\bigg|_{x=X,y=Y,t=T} uy +$$

$$\frac{d}{dt}\theta_A(x, y, t)\bigg|_{x=X,y=Y,t=T} \Delta t = 0$$

(or for unknown 2D velocity vector $(vx,vy)^T$:

$$\frac{d}{dx}\theta_A(x, y, t)\bigg|_{x=X,y=Y,t=T} vx + \frac{d}{dy}\theta_A(x, y, t)\bigg|_{x=X,y=Y,t=T} vy +$$

$$\frac{d}{dt}\theta_A(x, y, t)\bigg|_{x=X,y=Y,t=T} = 0).$$

$\theta_A(x,y,t)$ is the 2D phase distribution (x,y) of the complex signal A(x,y,t) (=Re[A(x,y,t)]+jIm[A(x,y,t)] of the point (x,y) at the time t ($\Delta t$: transmitted pulse interval):

$$\theta_A(x,y,z,t)=\tan^{-1}(Re[A(x,y,z,t)]/Im[A(x,y,z,t)]).$$

Method (II-3) can also be applied to measurement of one displacement component distribution.

On the method (II-1), utilized is phase of complex signal in beam direction or scan direction. The next equation holds for unknown displacement component ux at each point (X,Y,Z) at time t=T:

$$\frac{d}{dx}\theta_A(x, t)\bigg|_{x=X,t=T} ux + \frac{d}{dt}\theta_A(x, t)\bigg|_{x=X,t=T} \Delta t = 0$$

(or for unknown velocity component vx (the Doppler's equation):

$$\frac{d}{dx}\theta_A(x, t)\bigg|_{x=X,t=T} vx + \frac{d}{dt}\theta_A(x, t)\bigg|_{x=X,t=T} = 0\bigg).$$

$\theta_A(x,t)$ is the 1D phase distribution (x) of the complex signal A(x,t) of the point (x) at the time t ($\Delta T$: transmitted pulse interval).

In the ROI, by solving this equation for unknown displacement component ux (unknown velocity component vx) at each point, the displacement (velocity) component distribution (series) can be obtained.

On the method (II-2), in the ROI, occasionally also in time direction, this equation holds in beam direction or scan direction, and the derived simultaneous equations can be solved by least squared method, where, freely, regularization method can be applied (the temporal and spatial magnitude of the unknown displacement component distribution, temporal and spatial continuity and differentiability of the unknown displacement component distribution). Thus, the displacement component distribution (series) can be obtained.

On the methods (II-3) and (II-2), occasionally the unknown displacement (velocity) vector and the unknown displacement (velocity) vector component are dealt as locally uniform ones. That is, occasionally, under the assumption that the local region uniformly moves, the simultaneous equations hold for the unknown local displacement (velocity) vector or the unknown local displacement (velocity) component. Otherwise, occasionally, the simultaneous equations hold under the assumption that the displacement (velocity) is uniform for temporal finite interval. Thus, the spatial distribution (series) can be obtained.

The displacement vector distribution (series) can also be obtained by integrating the obtained velocity vector component distributions (series), or by multiplying transmitted pulse interval Ts to the obtained velocity vector component distributions (series).

From temporal spatial derivatives of these velocity vector distribution (series) or displacement vector distribution (series), obtained are strain tensor component distributions (series), strain tensor rate component distributions (series), and acceleration vector component distributions (series).

There are other various methods for estimating remaining estimation error vector. These methods can also be utilized in the same way. When estimation error of the displacement vector or remaining estimation error vector is detected during the iterative estimation a priori as the point of time-space magnitude and time-space continuity, for instance, the estimate can be cut by compulsion such that the estimate ranges from the given smallest value to the given largest value, or such that the difference between the estimates of the neighboring points settle within the given ranges.

As explained, on this conduct form, by iterative estimation the measurement accuracy can be improved of the displacement vector in the 3D SOI, particularly, 3D displacement vector, obtained from the cross-spectrum phase gradient etc. of the ultrasound echo signals acquired as the responses to more than one time transmitted ultrasound. The local echo signal can be shifted by multiplying complex exponential, or interporation can be performed after shifting sampling ultrasound signal. The present invention can improve measurement accuracy of lateral displacements (orthogonal directions to beam direction). Furthermore, the present invention can simplify calculation process into one without unwrapping the cross-spectrum phase nor utilizing cross-correlation method in order to reduce calculation amount and shorten calculation time.

Moreover, on this conduct form, large displacement (vector) and large strain (tensor) can be accurately measured by tracking ultrasound echo signals of targeted tissue using echo signal phase as the index (the local echo signal can be shifted by multiplying complex exponential, or interporation can be performed after shifting sampling ultrasound signal.), and by adding successively estimated at least more than two displacements.

Furthermore, on this conduct form, elastic constant and visco elastic constant can be accurately measured with high freedom of configurations of displacement (strain) sensors, mechanical sources, reference regions (mediums).

Next, explains are about elasticity and visco-elasticity constants measurement apparatus related to one of conduct forms of the present invention. The elasticity and visco-elasticity constants measurement apparatus related to this conduct form utilize the apparatus shown in FIG. 1 (same as that of the above-explained displacement vector and strain measurement), and the apparatus measures elastic constants and visco elastic constants from displacement vector, strain tensor, etc. measured by using the above-explained displacement and strain measurement method.

At first, the assumptions are explained of the elasticity and visco-elasticity constants measurement apparatus related to this conduct form. The following constants are assumed to be measured only in the target ROI (SOI) set in the measurement object, elastic constants such as shear modulus, Poisson's ratio, etc., visoc elastic constants such as visco shear modulus, visco Poisson's ratio, etc., delay times or relaxation times relating these elastic constants and visco elastic constants, or density. All the mechanical sources are assumed to exist outside of the ROI. Then, if there exist other mechanical sources in addition to set mechanical sources or if the mechanical sources are uncontrollable, the following constants can be measured in the target ROI (SOI), elastic constants such as shear modulus, Poisson's ratio, etc., visoc elastic constants such as visco shear modulus, visco Poisson's ratio, etc., delay times or relaxation times relating these elastic constants and visco elastic constants, or density. Neither information is needed about mechanical sources, such as positions, force directions, force magnitudes, etc. Moreover neither stress data nor strain data are needed at the target body surface. Only the ROI is modeled using finite difference method or finite element method.

If the mechanical sources originally exist near the ROI, only the mechanical sources can be utilized. In the case of observation of living tissues, for instance, such mechanical sources include normally uncontrollable mechanical sources such as heart motion, respiratory motion, blood vessel motion, body motion. In general, lung, air, blood vessel, blood are included in the ROI. In this case, without disturbing the deformation field, the following constants can be measured, i.e., elastic constants such as shear modulus, Poisson's ratio, etc., visoc elastic constants such as visco shear modulus, visco Poisson's ratio, etc., delay times or relaxation times relating these elastic constants and visco elastic constants, or density. This is effective particularly when the ROI deeply situates.

When solving the first order partial differential equations, as initial conditions the following can be utilized, i.e., reference shear modulus and reference Poisson's ratio for elastic constants, reference visco shear modulus and reference visco Poisson's ratio for visco elastic constants, reference density for density. In this case, reference mediums or reference regions are set in the original ROI or near the original ROI, after which the final ROI is set such that the final ROI includes the original ROI as well as the references. By measuring in the ROI including reference regions strain tensor field, strain rate tensor field, and acceleration vector field, the references are realized.

The size and the position of the reference mediums or reference regions should be set such that they should widely cross the direction of the dominant tissue deformation. For instance, if the mechanical source has large contact surface, large reference region must be set. Otherwise, if the mechanical source has small contact surface, by setting the reference region near the mechanical source, small reference region can be used. The estimates can be also used as their references.

The present invention can provide absolute shear modulus distribution, relative shear modulus distribution, absolute Poisson's ratio distribution, relative Poisson's ratio distribution, absolute visco shear modulus distribution, relative visco shear modulus distribution, absolute visco Poisson's ratio distribution, relative visco Poisson's ratio distribution, absolute or relative delay time distributions relating these elastic constants and visco elastic constants, or absolute or relative relaxation time distributions relating these elastic constants and visco elastic constants, absolute density distribution, or relative density distribution. Here, distributions of reference Poisson's ratio, reference visco Poisson's ratio, reference density must be distributions of absolute values, while distributions of other reference elastic constants, and reference visco elastic contants may be distributions of relative values.

As the numerical solution method of the first order partial differential equations, finite difference method or finite element method can be utilized. By utilizing the regularized algebraic equations, if the strain tensor field data is contaminated with errors (noises), or if the reference medium or reference region is small, or if the reference position is ill-conditioned, the following distribution can be stably estimated, i.e., shear modulus distribution, Poisson's ratio distribution, visco shear modulus distribution, visco Poisson's ratio, density, etc.

Referring to FIG. 1 again, next explain is about the means of data processing 1, i.e., calculation method of shear modulus distribution, Poisson's ratio distribution, visco shear modulus distribution, visco Poisson's ratio distribution, delay time distributions, relaxation time distributions, or density distribution, etc. When the 3D strain tensor, the 3D strain rate tensor, the 3D acceleration vector, etc. are measured, for instance, on the Cartesian coordinate system (x,y,z), the next simultaneous first order partial equations from (125) to (137") are dealt with, where the shear modulus distribution $\mu$, the Poisson's ratio distribution $\nu$, the visco shear modulus distribution $\mu'$, the visco Poisson's ratio distribution $\nu'$, the delay time distributions $\tau$, the relaxation time distributions $\tau'$, the strain tensor field $\epsilon$, the strain rate tensor field $\epsilon'$.

That is, when the 3D strain tensor is measured, and only the shear modulus distribution $\mu$ is unknown, the next equations are dealt with, $$\{\phi\varepsilon_{\alpha\alpha}\delta_{ij} + \varepsilon_{ij}\}(\ln\mu)_{,j} + \{\phi\varepsilon_{\alpha\alpha}\delta_{ij} + \varepsilon_{ij}\}_{,j} = 0, \text{ where} \quad (125)$$

$$\phi = \frac{v}{1-2v}, \text{ or} \quad (125')$$

$$\{\phi\varepsilon_{\alpha\alpha}\delta_{ij} + \varepsilon_{ij}\}\mu_{,j} + \{\phi\varepsilon_{\alpha\alpha}\delta_{ij} + \varepsilon_{ij}\}_{,j}\mu = 0, \text{ where} \quad (126)$$

$$\phi = \frac{v}{1-2v}. \quad (126')$$

When the 3D strain tensor is measured, and the shear modulus distribution µ and the Poisson's ratio distribution ν are unknown, the next equations are dealt with, $$\{\varepsilon_{\alpha\alpha}\delta_{ij}\}\lambda_{,j} + \{\varepsilon_{\alpha\alpha}\delta_{ij}\}_{,j}\lambda + 2\varepsilon_{ij}\mu_{,j} + 2\varepsilon_{ij,j}\mu = 0, \text{ where} \quad (127)$$

$$\lambda = \frac{2v}{1-2v}\mu. \quad (127')$$

When the 3D strain tensor and the 3D strain rate tensor are measured, and the shear modulus distribution µ and the visco shear modulus distribution µ' are unknown, the next equations are dealt with, $$\{\phi\varepsilon_{\alpha\alpha}\delta_{ij} + \varepsilon_{ij}\}\mu_{,j} + \{\phi\varepsilon_{\alpha\alpha}\delta_{ij} + \varepsilon_{ij}\}_{,j}\mu + \quad (128)$$
$$\{\phi'\varepsilon'_{\alpha\alpha}\delta_{ij} + \varepsilon'_{ij}\}\mu'_{,j} + \{\phi'\varepsilon'_{\alpha\alpha}\delta_{ij} + \varepsilon'_{ij}\}_{,j}\mu' = 0, \text{ where}$$

$$\phi = \frac{v}{1-2v}, \quad (128')$$

$$\phi' = \frac{v'}{1-2v'}, \text{ or} \quad (128'')$$

$$\left[\int_{t'}^{t}\phi(t-\tau)\mu(t-\tau)\exp\left\{-\frac{\phi(t-\tau)\mu(t-\tau)}{\phi'(t-\tau)\mu'(t-\tau)}(t-\tau)\right\}\varepsilon'_{\alpha\alpha}(\tau)d\tau\delta_{ij}\right]_{,j} + \quad (128''')$$
$$\left[\int_{t'}^{t}\mu(t-\tau)\exp\left\{-\frac{\mu(t-\tau)}{\mu'(t-\tau)}(t-\tau)\right\}\varepsilon'_{ij}(\tau)d\tau\right]_{,j} = 0,$$

where t' is initial time. If either the shear modulus distribution µ or the visco shear modulus distribution µ' is given, the next equations can be dealt with, $$\{\phi\epsilon_{\alpha\alpha}\delta_{ij}+\epsilon_{ij}\}\mu=\{\phi'\epsilon'_{\alpha\alpha}\delta_{ij}+\epsilon'_{ij}\}\mu'. \quad (128'''')$$

If both the shear modulus distribution µ and the visco shear modulus distribution µ' are unknown, from this equations, the relaxation time µ'(t)/µ(t) can be calculated, and can be utilized in the above equations (128''').

When the 3D strain tensor and the 3D strain rate tensor are measured, and the shear modulus distribution µ, the Poisson's ratio distribution ν, the visco shear modulus distribution µ', and the visco Poisson's ratio distribution ν' are unknown, the next equations are dealt with, $$\{\varepsilon_{\alpha\alpha}\delta_{ij}\}\lambda_{,j} + \{\varepsilon_{\alpha\alpha}\delta_{ij}\}_{,j}\lambda + 2\varepsilon_{ij}\mu_{,j} + 2\varepsilon_{ij,j}\mu + \quad (129)$$
$$\{\varepsilon'_{\alpha\alpha}\delta_{ij}\}\lambda'_{,j} + \{\varepsilon'_{\alpha\alpha}\delta_{ij}\}_{,j}\lambda' + 2\varepsilon'_{ij}\mu'_{,j} + 2\varepsilon'_{ij,j}\mu' = 0, \text{ where}$$

$$\lambda = \frac{2v}{1-2v}\mu, \quad (129')$$

$$\lambda' = \frac{2v'}{1-2v'}\mu', \text{ or} \quad (129'')$$

-continued $$\left[\int_{t'}^{t}\lambda(t-\tau)\exp\left\{-\frac{\lambda(t-\tau)}{\lambda'(t-\tau)}(t-\tau)\right\}\varepsilon'_{\alpha\alpha}(\tau)d\tau\delta_{ij}\right]_{,j} + \quad (129''')$$
$$2\left[\int_{t'}^{t}\mu(t-\tau)\exp\left\{-\frac{\mu(t-\tau)}{\mu'(t-\tau)}(t-\tau)\right\}\varepsilon'_{ij}(\tau)d\tau\right]_{,j} = 0,$$

where t' is initial time. Either both the shear modulus distribution µ and the visco shear modulus distribution µ' or both the Poisson's ratio distribution ν and visco Poisson's ratio distribution ν' are given, the next equations can be dealt with, $$\lambda\epsilon_{\alpha\alpha}\delta_{ij}+2\epsilon_{ij}\mu=\lambda'\epsilon'_{\alpha\alpha}\delta_{ij}+2\epsilon'_{ij}\mu'. \quad (129'''')$$

From this equations, the relaxation time µ'(t)/µ(t) can always be calculated. Then if either the shear modulus distribution µ or the visco shear modulus distribution µ' is given, the obtained shear modulus distribution µ and the obtained visco shear modulus distribution µ' can be utilized in the above equations (129'''). Otherwise, if either the Poisson's ratio distribution ν or the visco Poisson's ratio distribution ν' is given, the obtained Poisson's ratio distribution ν, the obtained visco Poisson's ratio distribution ν', and the obtained relaxation time λ'(t)/λ(t) can be utilized in the above equations (129''').

Equations (128'''), (128''''), (129'''), and (129'''') can be dealt with when the target is fluid such as water, secretions, blood, etc., or tissue includes the fluid much. The equations can also be dealt with after first temporal partial differentiation or partial integration. Theoretically, the elastic constant distributions and visco elastic constant distributions need to be invariant from the initial time t' to time t.

When the 2D strain tensor, the 2D strain rate tensor, etc. are measured, the simultaneous first order partial equations from (125) to (129'''') [i, j=1,2] or the next simultaneous first order partial equations from (130) to (134'''') [i, j=1,2] are dealt with. The equations from (125) to (129'''') [i, j=1,2] are dealt with approximately under plane strain condition, while the equations from (130) to (134'''') [i, j=1,2] are dealt with approximately under plane stress condition.

When the 2D strain tensor is measured, and only the shear modulus distribution µ is unknown, the next equations are dealt with, $$\{\varphi\varepsilon_{\alpha\alpha}\delta_{ij} + \varepsilon_{ij}\}(\ln\mu)_{,j} + \{\varphi\varepsilon_{\alpha\alpha}\delta_{ij} + \varepsilon_{ij}\}_{,j} = 0, \text{ where} \quad (130)$$

$$\varphi = \frac{v}{1-v}, \text{ or} \quad (130')$$

$$\{\varphi\varepsilon_{\alpha\alpha}\delta_{ij} + \varepsilon_{ij}\}\mu_{,j} + \{\varphi\varepsilon_{\alpha\alpha}\delta_{ij} + \varepsilon_{ij}\}_{,j}\mu = 0, \text{ where} \quad (131)$$

$$\varphi = \frac{v}{1-v}. \quad (131')$$

When the 2D strain tensor is measured, and the shear modulus distribution µ and the Poisson's ratio distribution ν are unknown, the next equations are dealt with, $$\{\varepsilon_{\alpha\alpha}\delta_{ij}\}\gamma_{,j} + \{\varepsilon_{\alpha\alpha}\delta_{ij}\}_{,j}\gamma + \varepsilon_{ij}\mu_{,j} + \varepsilon_{ij,j}\mu = 0, \text{ where} \quad (132)$$

$$\gamma = \frac{v}{1-v}\mu. \quad (132')$$

When the 2D strain tensor and the 2D strain rate tensor are measured, and the shear modulus distribution μ and the visco shear modulus distribution μ' are unknown, the next equations are dealt with, $$\{\varphi \varepsilon_{\alpha\alpha}\delta_{ij} + \varepsilon_{ij}\}\mu_{,j} + \{\varphi \varepsilon_{\alpha\alpha}\delta_{ij} + \varepsilon_{ij}\}_{,j}\mu + \qquad (133)$$
$$\{\varphi' \varepsilon'_{\alpha\alpha}\delta_{ij} + \varepsilon'_{ij}\}\mu'_{,j} + \{\varphi' \varepsilon'_{\alpha\alpha}\delta_{ij} + \varepsilon'_{ij}\}_{,j}\mu' = 0,$$

$$\text{where } \varphi = \frac{v}{1-v}, \qquad (133')$$

$$\varphi' = \frac{v'}{1-v'}, \text{ or} \qquad (133'')$$

$$\left[\int_{t'}^{t}\varphi(t-\tau)\mu(t-\tau)\exp\left\{-\frac{\varphi(t-\tau)\mu(t-\tau)}{\varphi'(t-\tau)\mu'(t-\tau)}\right\}\varepsilon'_{\alpha\alpha}(\tau)d\tau\delta_{ij}\right]_{,j} \qquad (133''')$$
$$+ \left[\int_{t'}^{t}\mu(t-\tau)\exp\left\{-\frac{\mu(t-\tau)}{\mu'(t-\tau)}(t-\tau)\right\}\varepsilon'_{ij}(\tau)d\tau\right]_{,j} = 0,$$

where t' is initial time. If either the shear modulus distribution μ or the visco shear modulus distribution μ' is given, the next equations can be dealt with, $$\{\phi\epsilon_{\alpha\alpha}\delta_{ij}+\epsilon_{ij}\}\mu=\{\phi'\epsilon'_{\alpha\alpha}\delta_{ij}+\epsilon'_{ij}\}\mu'. \qquad (133'''')$$

If both the shear modulus distribution μ and the visco shear modulus distribution μ' are unknown, from this equations, the relaxation time μ'(t)/μ(t) can be calculated, and can be utilized in the above equations (133''').

When the 2D strain tensor and the 2D strain rate tensor are measured, and the shear modulus distribution μ, the Poisson's ratio distribution v, the visco shear modulus distribution μ', and the visco Poisson's ratio distribution v' are unknown, the next equations are dealt with, $$\{\varepsilon_{\alpha\alpha}\delta_{ij}\}\gamma_{,j} + \{\varepsilon_{\alpha\alpha}\delta_{ij}\}_{,j}\gamma + \varepsilon_{ij}\mu_{,j} + \varepsilon_{ij,j}\mu + \qquad (134)$$
$$\{\varepsilon'_{\alpha\alpha}\delta_{ij}\}\gamma'_{,j} + \{\varepsilon'_{\alpha\alpha}\delta_{ij}\}_{,j}\gamma' + \varepsilon'_{ij}\mu'_{,j} + \varepsilon'_{ij,j}\mu' = 0,$$

$$\text{where } \gamma = \frac{v}{1-v}\mu, \qquad (134')$$

$$\gamma' = \frac{v'}{1-v'}\mu', \text{ or} \qquad (134'')$$

$$\left[\int_{t'}^{t}\gamma(t-\tau)\exp\left\{-\frac{\gamma(t-\tau)}{\gamma'(t-\tau)}(t-\tau)\right\}\varepsilon'_{\alpha\alpha}(\tau)d\tau\delta_{ij}\right]_{,j} + \qquad (134''')$$
$$\left[\int_{t'}^{t}\mu(t-\tau)\exp\left\{-\frac{\mu(t-\tau)}{\mu'(t-\tau)}(t-\tau)\right\}\varepsilon'_{ij}(\tau)d\tau\right]_{,j} = 0,$$

where t' is initial time. Either both the shear modulus distribution μ and the visco shear modulus distribution μ' or both the Poisson's ratio distribution v and visco Poisson's ratio distribution v' are given, the next equations can be dealt with, $$\gamma\epsilon_{\alpha\alpha}\delta_{ij}+\epsilon_{ij}\mu=\gamma'\epsilon'_{\alpha\alpha}\delta_{ij}+\epsilon'_{ij}\mu'. \qquad (134'''')$$

From this equations, the relaxation time μ'(t)/μ(t) can always be calculated. Then if either the shear modulus distribution μ or the visco shear modulus distribution μ' is given, the obtained shear modulus distribution μ and the obtained visco shear modulus distribution μ' can be utilized in the above equations (134'''). Otherwise, if either the Poisson's ratio distribution v or the visco Poisson's ratio distribution v' is given, the obtained Poisson's ratio distribution v, the obtained visco Poisson's ratio distribution v', and the obtained relaxation time γ'(t)/γ(t) can be utilized in the above equations (134''').

Equations (133'''), (133''''), (134'''), and (134'''') can be dealt with when the target is fluid such as water, secretions, blood, etc., or tissue includes the fluid much. The equations can also be dealt with after first temporal partial differentiation or partial integration. Theoretically, the elastic constant distributions and visco elastic constant distributions need to be invariant from the initial time t' to time t.

When the 1D strain tensor, the 1D strain rate tensor, etc. are measured, the simultaneous first order partial equations from (135) to (137'') are dealt with.

When the 1D strain tensor is measured, and only the shear modulus distribution μ is unknown, the next equations are dealt with, $$\varepsilon_{11}(\ln\mu)_{,1} + \varepsilon_{11,1} = 0, \text{ or} \qquad (135)$$

$$\varepsilon_{11}\mu_{,1} + \varepsilon_{11,1}\mu = 0. \qquad (136)$$

When the 1D strain tensor and the 1D strain rate tensor are measured, and the shear modulus distribution μ and the visco shear modulus distribution μ' are unknown, the next equations are dealt with, $$\varepsilon_{11}\mu_{,1} + \varepsilon_{11,1}\mu + \varepsilon'_{11}\mu'_{,1} + \varepsilon'_{11,1}\mu' = 0, \text{ or} \qquad (137)$$

$$\left[\int_{t'}^{t}\mu(t-\tau)\exp\left\{-\frac{\mu(t-\tau)}{\mu'(t-\tau)}(t-\tau)\right\}\varepsilon'_{11}(\tau)d\tau\right]_{,1} = 0, \qquad (137')$$

where t' is initial time. If either the shear modulus distribution μ or the visco shear modulus distribution μ' is given, the next equations can be dealt with, $$\epsilon_{11}\mu=\epsilon'_{11}\mu'. \qquad (137'')$$

If both the shear modulus distribution μ and the visco shear modulus distribution μ' are unknown, from this equation, the relaxation time μ'(t)/μ(t) can be calculated, and can be utilized in the above equations (137').

Equations (137') and (137'') can be dealt with when the target is fluid such as water, secretions, blood, etc., or tissue includes the fluid much. The equations can also be dealt with after first temporal partial differentiation or partial integration. Theoretically, the shear modulus distribution and visco shear modulus distribution need to be invariant from the initial time t' to time t.

In the equations (125), (130), (135), changed can be the signs of the terms not including (ln μ),j, and together changed can be (ln μ),j into {ln(1/μ)},j, then resultant partial differential equations can be dealt with for unknown ln(1/μ). Although regarding with equations (125), (130), (135) unknown ln μ cases are explained below, in unknown ln(1/μ) cases ln μ or μ can be estimated after ln(1/μ) or (1/μ) are estimated in similar ways.

In the equations (126), (131), (136), changed can be the signs of the terms not including μ,j, and together changed can be μ into (1/μ), then resultant partial differential equations can be dealt with for unknown (1/μ). Although regarding with equations (126), (131), (136) unknown μ cases are explained below, in unknown (1/μ) cases μ or ln μ can be estimated after (1/μ) or ln(1/μ) are estimated in similar ways.

These can be effective when the ROI includes extremely high shear modulus object such as bone, interstitial needle (for biopsy and treatment), etc.

When the target is fluid such as water, secretions, blood, etc., or tissue includes the fluid much, in the equations (125), (126), (127), (130), (131), (132), (135), (136) the elastic constants can be changed into the corresponding visco elastic constants, and the strain tensor can be changed into the strain rate tensor. Also in this case, in the equations (125), (130), (135), changed can be the signs of the terms not including (ln $\mu'$),j, and together changed can be (ln $\mu'$),j into $\{\ln(1/\mu')\}$,j, then resultant partial differential equations can be dealt with for unknown $\ln(1/\mu')$. Although regarding with equations (125), (130), (135) unknown ln $\mu$ cases are explained below, in unknown $\ln(1/\mu')$ cases ln $\mu'$ or $\mu$ can be estimated after $\ln(1/\mu')$ or $(1/\mu')$ are estimated in similar ways.

In the equations (126), (131), (136), changed can be the signs of the terms not including $\mu'$, j, and together changed can be $\mu'$ into $(1/\mu')$, then resultant partial differential equations can be dealt with for unknown $(1/\mu')$. Although regarding with equations (126), (131), (136) unknown $\mu'$ cases are explained below, in unknown $(1/\mu')$ cases $\mu'$ or ln $\mu'$ can be estimated after $(1/\mu')$ or $\ln(1/\mu')$ are estimated in similar ways.

These can be effective when the ROI includes extremely high shear modulus object such as bone, interstitial needle (for biopsy and treatment), etc.

When elasticity or visco elasticity is anisotropic, correspondingly derived equations from (125) to (137") can be dealt with.

Regarding density distribution $\rho$, measured acceleration vector field a is used. Specifically, in equations (126), (128), (128'''), (131), (132), (133), (133'''), (134), (134'''), $(\frac{1}{2})\rho a_i$ is added to right terms, in equations (127), (129), (129''') $\rho a_i$ is added to right terms, and in equations (136), (137), (137') $(\frac{1}{3})\rho a_i$ is added to right term. The known density distribution is used in the region, and the unknown density distribution is estimated with the unknown shear modulus distribution $\mu$, the unknown Poisson's ratio distribution $\nu$, the unknown visco shear modulus distribution $\mu'$, and the unknown visco Poisson's ratio distribution $\nu'$. When the target is fluid such as water, secretions, blood, etc., or tissue includes the fluid much, in the equations (126), (127), (131), (132), (136) the elastic constants can be changed into the corresponding visco elastic constants, and the strain tensor can be changed into the strain rate tensor. The density can not be handled when partial differential equations (126), (131), (136) are directly solved for $\ln(1/\mu)$, $(1/\mu)$, $\ln(1/\mu')$, and $(1/\mu')$.

Specifically, according to the measured deformation field, i.e., the strain tensor field, the strain rate tensor field [when dealing with the density $\rho$ (below omitted), the acceleration vector field, the temporal first derivative of the acceleration vector field, the strain tensor field, the strain rate tensor field] and/or the accuracy of the measured deformation field, dealt with all over the 3D SOI 7 are the simultaneous first order partial differential equations from (125) to (129""), or dealt with in the plural 3D SOIs, plural 2D ROIs, plural 1D ROIs set in the 3D SOI 7 are respectively the simultaneous first order partial differential equations from (125) to (129""), the simultaneous first order partial differential equations from (125) to (134""), the first order partial differential equations from (135) to (137"). When plural independent deformation fields are measured, according to the accuracy of the measured deformation fields, freely either of the equations from (125) to (137") or the plural equations of the equations from (125) to (137") can be dealt with at each point of interest. That is, these equations are solved individually or simultaneously. The plural independent deformation fields can be generated under the different positions of the mechanical sources and the reference regions. These 3D SOIs, 2D ROIs, and 1D ROIs can include same regions in the 3D SOI 7.

The Poisson's ratio and visco Poisson's ratio can respectively be approximated from ratios of the principal values of the strain tensor and strain rate tensor (on 3D measurement, either of three ratios of the principle values, or three or two mean values of the ratios). When plural deformation fields are measured, the Poisson's ratio and the visco Poisson's ratio can respectively be approximated as the mean value of the calculated ones from the plural fields. Typical values can also be utilized for the Poisson's ratio and the visco Poisson's ratio. For instance, the object is assumed to be incompressible, then the values are approximated as the value of about 0.5. Particularly, on equations from (130) to (134""), the object can be assumed to be completely incompressible, then the values are approximated as 0.5.

As initial conditions, at least at one reference point, or at least in properly set one wide reference region, given are reference shear modulus, reference Poisson's ratio, reference visco shear modulus, reference visco Poisson's ratio, etc.

That is, reference shear moduli (absolute or relative values) are given at least in one reference region $\overline{\omega}_{\mu,l}$ ($l=1\sim N_\mu$).

$$\ln \mu(x,y,z) = \ln \hat{\mu}(x,y,z), \overline{\omega}_{\mu,l} \in (x,y,z) \quad (138)$$

$$\mu(x,y,z) = \hat{\mu}(x,y,z), \overline{\omega}_{\mu,l} \in (x,y,z) \quad (138')$$

That is, reference Poisson's ratios (absolute values) are given at least in one reference region $\overline{\omega}_{\nu,l}$ ($l=1\sim N_\nu$).

$$\nu(x,y,z) = \hat{\nu}(x,y,z), \overline{\omega}_{\nu,l} \in (x,y,z) \quad (139)$$

That is, reference visco shear moduli (absolute or relative values) are given at least in one reference region $\overline{\omega}_{\mu',l}$ ($l=1\sim N_{\mu'}$).

$$\mu'(x,y,z) = \hat{\mu}'(x,y,z), \overline{\omega}_{\mu',l} \in (x,y,z) \quad (140)$$

That is, reference visco Poisson's ratios (absolute values) are given at least in one reference region $\overline{\omega}_{\nu',l}$ ($l=1\sim N_{\nu'}$).

$$\nu'(x,y,z) = \hat{\nu}'(x,y,z), \overline{\omega}_{\nu',l} \in (x,y,z) \quad (141)$$

When elasticity or visco elasticity is anisotropic, correspondingly derived equations from (125) to (137") and correspondingly derived initial conditions from (138) to (141) can be dealt with.

On discrete Cartesian's coordinate $(x,y,z) \sim (I\Delta x, J\Delta y, K\Delta z)$ in ROI 7 finite difference approximation or finite element method based on the Galerkin's method or the variational principle is applied to the shear modulus distribution $\mu$, the Poisson's ratio distribution $\nu$, the elastic constant distribution $\phi$, the elastic constant distribution $\lambda$, the elastic constant distribution $\phi$, the elastic constant distribution $\gamma$, the visco shear modulus distribution $\mu'$, the Poisson's ratio distribution $\nu'$, the visco elastic constant distribution $\phi'$, the visco elastic constant distribution $\lambda'$, the visco elastic constant distribution $\phi'$, the visco elastic constant distribution $\gamma'$, the displacement distribution, the strain distribution, and the strain rate distribution. Then algebraic equations are derived from the first order partial differential equations and initial conditions, and usually the algebraic equations are normalized, for instance, by the root square of the summation of the powers of the spatially inhomogeneous coefficients (or the distributions) multiplied to the shear modulus (distribution) $\mu$, the Poisson's ratio (distribution) $\nu$, the elastic constant (distribution) $\phi$, the elastic constant (distribution) $\lambda$, the elastic constant (distribution) $\phi$, the elastic constant (distribution) $\gamma$, the visco shear modulus (distribution) $\mu'$, the Poisson's ratio (distribution) $\nu'$, the visco elastic constant (distribution) $\phi'$, the visco elastic constant (distribution) $\lambda'$, the visco elastic constant (distribution)

φ', the visco elastic constant (distribution) γ'. Furthermore, the algebraic equations can be regularized. Here, elastic constants λ and μ are called as Lame's constants, while visco elastic constants λ' and μ' are called as visco Lame's constants.

For instance, finite difference method is utilized, the simultaneous equations are derived.

$$EGs = e \tag{142}$$

s is unknown vector comprised of the unknown shear modulus distribution μ, the unknown elastic constant distribution λ, the unknown elastic constant distribution γ, the unknown visco shear modulus distribution μ', the unknown visco elastic constant distribution λ', the unknown visco elastic constant distribution γ', etc. G is coefficients matrix comprised of finite approximations of the 3D, 2D or 1D partial derivatives. E and e are respectively matrix and vector comprised of strain tensor data, strain rate tensor data, their derivatives, and given elastic constants, or visco elastic constants.

Equations (142) is solved by least squares method, where in order to reduce the noises of the measured strain tensor data and strain rate tensor data, the strain distribution and the strain rate distribution are determined as spatially, temporally, or spatio-temporally low pass filtered ones. However, inverse of EG amplifies the high frequency noises filled with e. Then, s becomes unstable. Thus, to stabilize s the regularization method is applied. Utilizing the regularization parameters α1 and α2 (at least larger than zero), next equation (143) is minimized with respect to s, where T indicates transpose.

$$\text{error}(s) = |e - EGs|^2 + \alpha 1 |Ds|^2 + \alpha 2 |D^T Ds|^2 \tag{143}$$

D and $D^T D$ are respectively 3D, 2D, or 1D gradient and Laplacian operator of the unknown shear modulus distribution μ, the unknown elastic constant distribution λ, the unknown elastic constant distribution γ, the unknown visco shear modulus distribution μ', the unknown visco elastic constant distribution λ', the unknown visco elastic constant distribution γ', etc. That is, with respect to each unknown distribution, the regularization method can be applied over the 3D SOI, plural 3D SOIs, 2D ROIs, or 1D ROIs. As Ds and $D^T D$ are positive definite, error(s) absolutely has one minimum value. By minimizing error(s), the next regularized normal equations are derived.

$$(G^T E^T EG + \alpha 1 D^T D + \alpha 2 D^T D D^T D)s = G^T E^T e \tag{144}$$

Therefore, the solusion is obtained as $$s = (G^T E^T EG + \alpha 1 D^T D + \alpha 2 D^T D D^T D)^{-1} G^T E^T e \tag{145}$$

When the finite element method is utilized, in similar ways, the least squares method and the regularization method are applied to the derived simultaneous equations. In this case, G is comprised of basis function of the unknown nodal elastic modulus distribution and the unknown nodal visco elastic modulus distribution. Moreover, utilizing the regularization parameter α0 (at least larger than zero), $\alpha 0 |s|^2$ and $\alpha 0 |Gs|^2$ can be added to the equation (143). Furthermore, instead of $\alpha 1 |Ds|^2$ and $\alpha 2 |D^T Ds|$, $\alpha 1 |DGs|$ and $\alpha 2 |D^T DGs|$ can also be utilized.

The regularization parameter of important information is set relatively large. Thus, the regularization parameter utilized for each constant depends on deformation measurement accuracy (SNR), deformation state, configurations of mechanical sources and reference regions, number of the utilized independent deformation fields, etc.; then position of the unknown constant, direction of the partial derivative, etc.

From the ratio of each elastic constant E with respect to the corresponding visco elastic constant E', i.e., (E'/E), for instance, when measured are the shear modulus, the Poisson's ratio, the Lame constants, etc. and their corresponding visco elastic modulus, estimated can be the time delay distribution τ [case when visco elastic modulus is determined from (128), (129), (133), (134), (136), or (137)] or relaxation time distribution τ' [case when visco elastic modulus is determined from (128'''), (128''''), (129'''), (129''''), (133'''), (133''''), (134'''), (134''''), (136'''), (136''''), (137'), or (137''), or case when visco elastic modulus is determined from (125), (126), (127), (130), (131), (132), (135), or (136) where the elastic moduli and strain tensor components are respectively changed into the corresponding visco elastic mouli and the strain rate tensor components]. Moreover, from strain tensor data and elastic moduli data, elastic energy distribution can be obtained, while from strain rate tensor data and visco elastic moduli data, consumed energy distribution can be obtained.

These elastic constants and visco elastic constants can be temporally changed. Thus, the spatial and temporal simultaneous equations of the above-described equation can be handled, where above-described regularization method can spatially and temporally be applied.

If the time sequence of the elastic modulus distribution or the visco elastic modulus distribution is estimated, by spectrum analysis, the distribution of the frequency variance of the elastic modulus or the visco elastic modulus can approximately be obtained. Moreover, if the time sequence of the time delay distribution or the relaxation time distribution is estimated, by spectrum analysis, the distribution of the frequency variance of the time delay or the relaxation time can approximately be obtained. When estimating the distributions of the frequency variances of these elastic modulus, visco elastic modulus, time delay, relaxation time, the deformation field is measured with changing the frequency of the mechanical source, or with utilizing broadband mechanical source. Furthermore, at each time, from strain tensor data and elastic moduli data, elastic energy distribution can be obtained, while from strain rate tensor data and visco elastic moduli data, consumed energy distribution can be obtained.

When solving by the iterative method such as the conjugate gradient method equations from (143) to (145) derived from equations from (125) to (137'') for each unknown elastic modulus distribution and each unknown visco elastic modulus distribution, as explained below, if necessary, newly the reference regions are set in the ROI in addition to the pre-described reference regions, and properly initial values of the estimates are set in the unknown region. In general, each initial value is set based on the a priori information such as homogeneity and inhomogeneity. Thus, calculation amount can be reduced.

Regarding with elasticity distribution, for instance, on 1D measurement based on the partial differential equation (135) or (136), by analytically solving these equations, the relative shear modulus of the point x=X with respect to the point x=A can be estimated from the ratio of the strains ε(A)/ε(X) (Japanese Patent Application Publication JP-7-55775). This is effective when tissues deforms in x direction. (Moreover, regarding with visco elasticity distribution, for instance, on 1D measurement based on the partial differential equation (135) or (136), by analytically solving these equations, the relative visco shear modulus of the point x=X with respect to the point x=A can be estimated from the ratio of the strain rates ε'(A)/ε'(X). Below, the shear modulus is dealt with, for instance.)

However, for instance, in the singular points or the singular regions where the strain is numerically zero, or the sign of the strain changes, the shear modulus can be stably estimated with the above-described regularization method using the absolute reference values or the relative reference values (reference values obtained from ratio of the strains in addition to given reference values.). Otherwise, in the unknown points or the unknown regions where the absolute strain is less than the positive value A (threshold), in a similar way, the shear modulus can be stably estimated using the absolute reference values or the relative reference values (reference values obtained from ratio of the strains in addition to given reference values.). In these cases, the initial values utilized for solving the equations from (143) to (145) can be determined with various interporation method (quadrature interporation, cosine interporation, Lagrange's interporation, spline interporation) such that the values are spatially continuous with the reference values and the initial values determined from the a priori information. The threshold A being dependent on the power or the accuracy (SNR) of the strain data at each point, the threshold can be spatio-temporally changeable. The threshold can be set as small value when or where the SNR of the strain is high, while the threshold can be set as large value when or where the SNR of the strain is low. Otherwise, in the unknown points or the unknown regions where the relative shear modulus values obtained from stain ratio with respect to the reference values are larger than the relative value B (threshold), in a similar way, the shear modulus can be stably estimated using the absolute reference values or the relative reference values (reference values obtained from ratio of the strains in addition to given reference values.). Also in this case, the initial values can be determined with various interporation method such that the values are spatially continuous with the reference values and the initial values determined from the a priori information. The threshold B being dependent on the power or the accuracy (SNR) of the strain data at each point, the threshold can be spatio-temporally changeable. The threshold can be set as high value when or where the SNR of the strain is high, while the threshold can be set as low value when or where the SNR of the strain is low. The strain distribution data to determine reference regions is moving-averaged with the spatio-temporally changeable window. Otherwise, to properly set the reference regions (values) and the initial values, the initial values can be calculated with various interporation method (including linear interporation), and freely the reference values and initial values can be spatio-temporally low pass filtered. However, given $\mu(A)$ is unchangeable. Also on other equations, the reference regions should be widely set, in a similar way, the initial values, the singular points or the singular regions, the unknown points or the unknown regions can be dealt with. The method to set reference regions explained here can also be adopted when the direct method is utilized.

When solving equations from (143) to (145) derived from equations from (125) to (137″) by the iterative method for each unknown elastic modulus distribution and each unknown visco elastic modulus distribution, by properly setting initial values of the estimates, calculation amount can be reduced. For instance, when solving equation (135) or (136) for unknown shear modulus distribution, the initial values can be determined from the above-described strain ratio. In the above-described singular points, the singular regions, the points or regions where the absolute strain is less than the positive value A (threshold), or the points or regions where the relative shear modulus values obtained from stain ratio with respect to the reference values are larger than the relative value B (threshold), the initial values can be determined with various interporation method (quadrature interporation, cosine interporation, Lagrange's interporation, spline interporation) such that the values are spatially continuous with the reference values and the initial values (the initial values determined from the a priori information or strain ratio). Otherwise, in the above-described singular points, the singular regions, the points or regions where the absolute strain is less than the positive value A (threshold), or the points or regions where the relative shear modulus values obtained from stain ratio with respect to the reference values are larger than the relative value B (threshold), to properly set the initial values, the initial values can be calculated with various interporation method (including linear interporation) from the reference values and the initial values (the initial values determined from the a priori information or strain ratio), and freely the reference values and the initial values can be spatio-temporally low pass filtered. However, given $\mu(A)$ is unchangeable. These thresholds being dependent on the power or the accuracy (SNR) of the strain data at each point, these thresholds can be spatio-temporally changeable. The thresholds A and B can respectively be set as small and high values when or where the SNR of the strain is high, while the thresholds A and B can respectively be set as large and low values when or where the SNR of the strain is low. Regarding with other elastic modulus distributions or other visco elastic modulus distributions, in a similar way, the initial values can be dealt with.

Regarding with some elastic moduli and visco elastic moduli, as above-explained the reference regions (reference values) and the initial estimates are set and utilized, and simultaneously other elastic moduli and visco elastic moduli can be dealt with.

During iterative estimation, if elastic modulus, visco elastic modulus, time delay, relaxation time, density are estimated as the values out of the a priori known ranges, they are corrected such that they are satisfied with the a priori data. For instance, the (visco) elastic moduli are positive values. The (visco) Poisson's ratio is less than 0.5. Then, for instance, if the (visco) elastic moduli are estimated as negative values, they are corrected as positive values but nearly equals to zero. If the (visco) Poisson's ratio are estimated to be larger than 0.5, they are corrected to be smaller than 0.5 but nearly equals to 0.5. If plane stress condition is assumed, the (visco) Poisson's ratio can be corrected to be 0.5.

On the 1D or 2D measurement of the elastic constants such as the shear modulus, the Poisson's ratio, etc., and visco elastic constants such as the visco shear modulus, the visco Poisson's ratio, etc., they are estimated to be smaller than the original values when the point of interest gets far from the mechanical source. In this case, the same shape model having homogeneous elastic modulus and visco elastic modulus and the same mechanical source model are utilized, the analytically or numerically estimated strain data and strain rate data can be utilized to correct the measured strain data and strain rate data. Otherwise, on this model analytically or numerically estimated stress data can be utilized to correct measured elastic modulus distribution and visco elastic modulus distribution. Otherwise, on this model the elastic modulus and visco elastic modulus are estimated from the analytically or numerically estimated strain data and strain rate data, and the estimates can be utilized to correct measured elastic modulus distribution and visco elastic modulus distribution.

The temporal absolute change of the elastic constants such as the shear modulus, the Poisson's ratio, etc., visco elastic constants such as the visco shear modulus, the visco Poisson's ratio, etc., time delay, relaxation time can be obtained as the difference of the estimated absolute values. The temporal relative change of the elastic constants, visco elastic constants, time delay, relaxation time can be obtained as the ratio of the estimated absolute or relative values, or regarding with the elastic constants or the visco elastic constants, the temporal relative change can be obtained as the difference of the estimated logarithms of them. In this way, on signal processing regarding with the elastic constants or the visco elastic constants, the logarithm can be utilized.

When iteratively solving the equations from (143) to (145), the initial estimate can be obtained from previous time estimate; reducing the calculation amount. During iterative estimation, if elastic modulus, visco elastic modulus, time delay, relaxation time, density are estimated as the values out of the a priori known ranges, they are corrected such that they are satisfied with the a priori data. For instance, the (visco) elastic moduli are positive values. The (visco) Poisson's ratio is less than 0.5. Then, for instance, if the (visco) elastic moduli are estimated as negative values, they are corrected as positive values but nearly equals to zero. If the (visco) Poisson's ratio are estimated to be larger than 0.5, they are corrected to be smaller than 0.5 but nearly equals to 0.5. If plane stress condition is assumed, the (visco) Poisson's ratio can be corrected to be 0.5.

The above-explained regularization parameter can be set larger value when the point of interest gets far from the reference region along dominant tissue deformation direction.

On equations from (125) to (137"), the spectrum of the unknown elastic constants and unknown visco elastic constants are handled, where the regularization method can be applied not only in the above-described spatio-temporal directions but also in the frequency direction.

For instance, in the 1D ROI (x axis), when measurement target are frequency variance (spectrum component distribution and phase distribution) of the sequence of shear modulus distribution $\mu(x,t)$ and the sequence of visco shear modulus distribution $\mu'(x,t)$, the discrete sequence $\mu(x,j)$ [j=t/$\Delta$t (=0~n)] of $\mu(x,t)$ can be expressed as $$\mu(x, j) = \frac{1}{n+1} \sum_{l=0}^{n} [\mu(x, l) \exp(j\theta_\mu(x, l))] \begin{bmatrix} \cos(2\pi l \Delta f j \Delta t) + \\ j\sin(2\pi l \Delta f j \Delta t) \end{bmatrix}$$

where $\mu(x,l)$ and $\theta_\mu(x,l)$ are respectively the spectrum component of the frequency l and the phase of the frequency l. j expresses imaginary unit. l (=0~n) is the discrete frequency coordinate (f=l$\Delta$f).

The discrete sequence $\mu'(x,j)$ [j=t/$\Delta$t (=0~n)] of $\mu'(x,t)$ can be expressed as $$\mu'(x, j) = \frac{1}{n+1} \sum_{l=0}^{n} [\mu'(x, l) \exp(j\theta_{\mu'}(x, l))] \begin{bmatrix} \cos(2\pi l \Delta f j \Delta t) + \\ j\sin(2\pi l \Delta f j \Delta t) \end{bmatrix}$$

where $\mu'(x,l)$ and $\theta_{\mu'}(x,l)$ are respectively the spectrum component of the frequency l and the phase of the frequency l.

Then, the first order differential equation (137) can be expressed as $$\sum_{l=0}^{n} \left[ \left( \varepsilon_{xx}(x, j) \frac{\partial}{\partial x} \mu(x, l) + \frac{\partial}{\partial x} \varepsilon_{xx}(x, j) \mu(x, l) \right) \exp(j\theta_\mu(x, l)) + \right. \quad (146)$$

-continued
$$\left. \left( \varepsilon'_{xx}(x, j) \frac{\partial}{\partial x} \mu'(x, l) + \frac{\partial}{\partial x} \varepsilon'_{xx}(x, j) \mu'(x, l) \right) \exp(j\theta_{\mu'}(x, l)) \right]$$
$$\{\cos(2\pi l \Delta f j \Delta t) + j\sin(2\pi l \Delta f j \Delta t)\} = 0$$

Thus, with respect to each frequency l, the following simultaneous first order differential equations hold.

$$\left( \varepsilon_{xx}(x, j) \frac{\partial}{\partial x} \mu(x, l) + \frac{\partial}{\partial x} \varepsilon_{xx}(x, j) \mu(x, l) \right) \cos(\theta_\mu(x, l)) + \quad (146')$$
$$\left( \varepsilon'_{xx}(x, j) \frac{\partial}{\partial x} \mu'(x, l) + \frac{\partial}{\partial x} \varepsilon'_{xx}(x, j) \mu'(x, l) \right)$$
$$\cos(\theta_{\mu'}(x, l)) = 0$$

$$\left( \varepsilon_{xx}(x, j) \frac{\partial}{\partial x} \mu(x, l) + \frac{\partial}{\partial x} \varepsilon_{xx}(x, j) \mu(x, l) \right) \sin(\theta_\mu(x, l)) + \quad (146'')$$
$$\left( \varepsilon'_{xx}(x, j) \frac{\partial}{\partial x} \mu'(x, l) + \frac{\partial}{\partial x} \varepsilon'_{xx}(x, j) \mu'(x, l) \right)$$
$$\sin(\theta_{\mu'}(x, l)) = 0$$

The simultaneous differential equations (146') and (146") can be finite difference approximated or finite element approximated in the same way where the equation (137) is dealt with at each time j (=0~n).

By substituting the known nodal distribution of the real components and imaginary components of the spectrum of the frequency l (=0~n) of the elastic constant and visco elastic constant [$\mu$(l,l)cos $\theta_\mu$(l,l), $\mu$(l,l)sin $\theta_\mu$(l,l), $\mu'$(l,l)cos $\theta_{\mu'}$(l,l), $\mu'$(l,l)sin $\theta_{\mu'}$(l,l)], at each time j (j=0~n), simultaneous equations (142) are derived each for real components $\mu$(l,l)cos $\theta_\mu$(l,l) and $\mu'$(l,l)cos $\theta_{\mu'}$(l,l), and imaginary components $\mu$(l,l)sin $\theta_\mu$(l,l) and $\mu'$(l,l)sin $\theta_{\mu'}$(l,l).

In this way, on equations from (125) to (137"), the simultaneous equations are derived respectively for real components of the spectrum of the elastic constants and visco elastic constants, and imaginary components of the spectrum of the elastic constants and visco elastic constants. When respective simultaneous equations are regularized, as above-explained, usually, for instance, the derived algebraic equations are normalized by the root square of the summation of the powers of the spatially inhomogeneous coefficient distributions multiplied to the unknown distributions.

(A) Two equations derived on each sequence i (=1~M), each time j (=0~n), each frequency l (=0~n), are respectively solved for of the frequency l real component distributions and imaginary component distributions of the spectrum of the unknown parameters.

(B) Respective two equations derived from different sequence i (=1~M), different time j (=0~n), are simultaneously set for of the frequency l real component distributions and imaginary component distributions of the spectrum of the unknown parameters, and solved.

(C) Respective two equations derived from different sequence i (=1~M), different time j (=0~n), are simultaneously set for of the frequency l real component distributions and imaginary component distributions of the spectrum of the unknown parameters, and by spatial regularization stably solved.

(D) Respective two equations derived from different sequence i (=1~M), different time j (=0~n), are simultaneously set for of the frequency l real component distributions and imaginary component distributions of the spectrum of the unknown parameters, and by temporal regularization stably solved.

(E) Respective two equations derived on each sequence i (=1~M), each time j (=0~n), each frequency l (=0~n), are simultaneously set for real component distributions and imaginary component distributions of the spectrum of the unknown parameters, and by frequency regularization stably solved. Spatial, and temporal regularization can also simultaneously be performed.

As above-explained, by one of (A), (B), (C), (D), (E), the frequency variances of the unknown elastic constants and visco elastic constants can be obtained.

The sequences of the nodal elastic constant distributions and nodal visco elastic constant distributions can be obtained by inverse Fourier's transform of the spectrums. For instance, the sequence of the nodal shear modulus distribution is $$\mu(I, j) = \frac{1}{n+1} \sum_{j=0}^{n} [\mu(I, l) \exp(j\theta_\mu(I, j))] \begin{bmatrix} \cos(2\pi l \Delta f j \Delta t) + \\ j\sin(2\pi l \Delta f j \Delta t) \end{bmatrix},$$

from which the sequence of the shear modulus distribution $\mu(x,t)$ can be obtained.

On also equations from (125) to (137"), the sequences of the nodal elastic constant distributions and nodal visco elastic constant distributions can be obtained by inverse Fourier's transform of the spectrums.

The deformation fields are measured with changing the frequency of the mechanical source, or by utilizing broadband mechanical source.

When instantaneous frequency of the deformation data can be measured, the frequency l can be dealt with as the instantaneous frequency.

Fourier's transform can be applied not only for time direction but also spatial direction.

On equations (126), (127), (128), (129), (131), (132), (133), (134), (136), (137) and (128'''), (128''''), (129'''), (129''''), (133'''), (133''''), (134'''), (134''''), (137'), (137") in order to deal with frequency variances of the sequences of the elastic constants and visco elastic constants, (126), (127), (128), (128''''), (129), (129''''), (131), (132), (133), (133''''), (134), (134''''), (136), (137), (137") can be approximated utilizing convolute integration as like (128'''), (129'''), (133'''), (134'''), (137'). For instance, equation (137) can be approximated as $$\left[\int_{t'}^{t} \mu(t-\tau)\varepsilon'_{11}(\tau) d\tau\right]_{,1} + \left[\int_{t'}^{t} \mu'(t-\tau)\varepsilon''_{11}(\tau) d\tau\right]_{,1} = 0, \quad (137''')$$

where t' is initial time, $\epsilon''_{11}(t)$ is first order derivative of the strain rate $\epsilon'_{11}(t)$.

As like on (128'''), (129'''), (133'''), (134'''), (137'), regularization can be performed temporally and spatially.

After Fourier's transform, regularization can also be performed spatial direction, time direction, and in frequency domain. For instance, equation (137'''):

$$[N(I,l)E'_{11}(I,l)]_{,1} + [N'(I,l)E''_{11}(I,l)]_{,1} = 0,$$

where $E'_{11}(I,l)$ is Fourier's transform of the strain rate $\epsilon'_{11}(I,j)$, and $E''_{11}(I,l)$ is Fourier's transform of the first order derivative of the strain rate $\epsilon''_{11}(I,j)$. From Fourier's transform $E_{11}$ (I,l) and $E'_{11}(I,l)$ respective of the strain $\epsilon(I,j)$ and the strain rate $\epsilon'_{11}(I,j)$, $E'_{11}(I,l)$ and $E''_{11}(I,l)$ can be obtained as $$E'_{11}(x, 1) = (j2\pi l \Delta f) E_{11}(x, 1) \quad (137'''')$$

$$E''_{11}(x, 1) = (j2\pi l \Delta f) E'_{11}(x, 1)$$

$$= (j2\pi l \Delta f)^2 E_{11}(x, 1).$$

When dealing with density, density can also be obtained through regularization.

In order to determine the unknown elastic constant distributions, the unknown visco elastic constant distributions, the unknown density distribution, equations from (125) to (137") can also be solved utilizing elastic constant data, visco elastic constant data, density data obtained on equations from (125) to (137"), and other deformation data.

Figure 26:
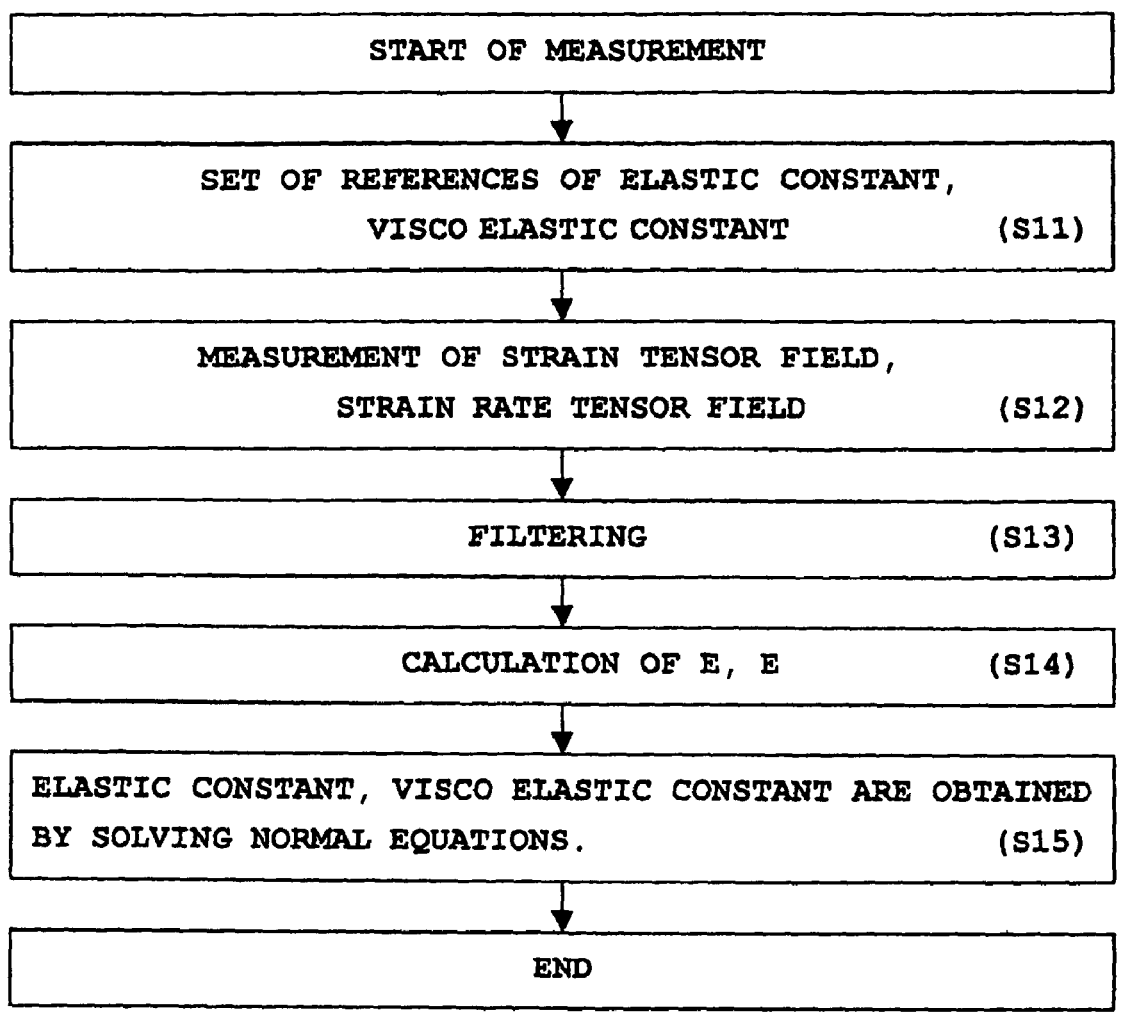
FIG. 26 shows flowchart of measurement procedure of elasticity constants, and visco-elasticity constants utilizing the elasticity and visco-elasticity constants measurement apparatus (FIG. 1)

Next, utilizing the flowchart of FIG. 26, explained is measurement procedure of the elastic constant distributions such as the shear modulus, the Poisson's ratio, etc., the visco elastic constant distributions such as the visco shear modulus, the visco Poisson's ratio, etc., time delay distributions, relaxation time distributions, and the density distributions. At first, reference regions are properly set for the unknown elastic constants, the unknown visco elastic constants, the unknown density (S11). Otherwise, as the reference region, reference points are set in the ROI 7. Reference point has known elastic constants, known visco elastic constants, or known density. Otherwise, the reference point has the reference unity value, or other finite reference values.

To obtain high accuracy the elastic constants, the visco elastic constants, and the density, the reference regions should be set such that they should widely cross the direction of the dominant tissue deformation. The reference region has known elastic constant distributions, known visco elastic constant distributions, known density distribution, or a priori assumed distributions. When measuring the absolute elastic constant distributions, the absolute visco elastic constant distributions, the absolute density distribution, the given reference values must be absolute values.

Occasionally, by assuming the stress distribution in the reference region, from measured strain values the reference elastic constant is determined. (For instance, by assuming the stress distribution to be constant, from strain ratio the reference elastic constant can be determined.). Moreover, by assuming the stress distribution in the reference region, from strain rate values the reference visco elastic constant is determined. (For instance, by assuming the stress distribution to be constant, from strain rate ratio the reference visco elastic constant can be determined.).

When there exist neither reference point nor reference regions, if reference medium can directly be contacted to object, the deformations (strain tensor field, strain rate tensor field, acceleration vector field) are measured over the ROI including the reference (S12). In this case, the shear modulus value of the reference should be large compared with that of the target. The reference medium should be put between the mechanical source 8 and the ROI.

As the object is deformed in 3D space, 3D reconstruction should be carried out. However, when estimating in the superficial tissues the elastic constants, the visco elastic constants, and the density, 1D reconstruction method [from (135) to (137")] is useful since utilized can be accurately measured strain data, strain rate data, and acceleration data in beam direction. In contrast, when estimating in the deeply situated tissues the elastic constants, the visco elastic constants, and the density, multi-dimensional reconstruction method is useful since the freedom of configurations can be high of mechanical sources and reference regions (mediums).

Specifically, on 2D reconstruction, when 2D strain distribution approximately occurs, equations from (125) to (129"") can be utilized. Alternatively, when 2D stress distribution approximately occurs, equations from (130) to (134"") can be utilized. To measure independent deformation fields (strain tensor fields, strain rate tensor fields, acceleration vector fields), the position of the mechanical source 8 is changed. Since the measurement accuracy of the strains, strain rates, acceleration vectors rely on their magnitudes, to measure the elastic constants, the visco elastic constants, the density with uniform accuracy over the ROI, the position of the mechanical source 8 should be variously changed. This measurement accuracy has the relationship of trade off between the measurement time and the cost. As already described, when the object is spontaneously deformed due to mechanical sources 8' and 8", the mechanical source 8 may not be needed.

The measurement controller 3 controls the positions of the object 6 and the displacement (strain) sensor 5, and the measurement controller 3 inputs the position information and the echo signals into the storage 2. At the data processor 1, measured strain data, strain rate data, acceleration data are filtered to reduce noises (S13), by which spatially smoothed coefficients E and e are obtained (S14). Subsequently, the elastic constant distributions, the visco elastic constant distributions, the density distribution are obtained from the normal equations (144) (S15). Thus, measurement results are, at each time, displacement vector distribution, strain tensor distribution, gradient distribution of the strain tensor, strain tensor rate distribution, gradient distribution of the strain rate tensor, elastic constant distributions such as shear modulus, Poisson's ratio, Lame constants, etc., visco elastic constant distributions such as visco shear modulus, visco Poisson's ratio, visco Lame constants, etc., time delay distributions or relaxation time distributions relating these elastic constants and visco elastic constants, density distribution, gradient distributions of these results, Laplacian distributions of these results, temporal first derivatives of these results, temporal second derivatives of these results. To store time series of these measurement results, these measurement results (output of data processor 1) are input into the storage 2. To display in real time these measurement results on CRT (color or gray), the output of data processor 1 can be input into display equipment. Freeze image can also be displayed. When displaying these measurement results, each measurement result can be truncated by respectively set upper value or lower value. When displaying elastic constant distributions or visco elastic constant distributions, the inversion can be also displayed. Moreover, direct current can be added to the measurement results, or subtracted from the measurement results. When displaying strain tensor distribution, to make the sign of the strain invariant, the direct current can be added (the brightness should be assigned such that the strain image has correlation with the elastic constant image). Furthermore, each measurement result can also be displayed in log scaled.

Measurement results are, at each time, displacement vector distribution, strain tensor distribution, gradient distribution of the strain tensor, strain tensor rate distribution, gradient distribution of the strain rate tensor, elastic constants such as shear modulus, Poisson's ratio, Lame constants, etc., visco elastic constants such as visco shear modulus, visco Poisson's ratio, visco Lame constants, etc., time delay distributions or relaxation time distributions relating these elastic constants and visco elastic constants, density distribution, gradient distributions of these results, Laplacian distributions of these results, temporal first derivatives of these results, temporal second derivatives of these results, time series of these results, time series of relative (ratio) changes of these results or absolute (substraction) changes of these results, frequency variance distributions of these results, elastic energy at each time or accumulations, consumed energy at each time or accumulations, time series of elastic energy at each time or accumulations, consumed energy at each time or accumulations, time series of relative (ratio) changes of these energy or absolute (substraction) changes of these energy. When there exist no stain data point or no strain data region, the elastic constants etc. are interporated or extraporated from measured ones. The results can be stored at storage 2, and can be displayed.

These results can be obtained through spatial filtering of the absolute elastic constant distributions, absolute visco elastic constant distributions, absolute time delay distributions, absolute relaxation time distributions, absolute density distributions, or relative these distributions obtained from the normal equations (144). Otherwise, obtained these results can be spatially filtered. Otherwise, these results can be obtained through temporal or spatial or temporal-spatial filtering of the elastic constant distributions, visco elastic constant distributions, time delay distributions, relaxation time distributions, density distributions. Otherwise, obtained these results can be temporally or spatially or temporal-spatially filtered. These results can be stored at storage 2, and can be displayed. The spatial filter, the temporal filter, and the temporal-spatial filter are high pass type, band pass type, low pass type. These filters can be freely utilized at data processor 1.

For equations (125) to (137"), the unknown elastic constant distribution, the unknown visco elastic constant distribution, the unknown density distribution can be obtained from the measured elastic constant distribution, visco elastic constant distribution, density distribution using another deformation field data, or obtained from their typical value distributions.

By utilizing the ultrasonic diagnosis equipment together, the spatial variations of the bulk modulus and the density can be measured together, and can be displayed together. In this case, utilized together are the data processor 1, the data storage 2, the measurement controller 3, displacement (strain) sensor 5, transmitting/output controller 5' etc (FIG. 1). By utilizing the magnetic nuclear imaging equipment together, the atomic density distribution can be measured together, and can be displayed together.

As above-described (FIG. 1), using the displacement (strain) sensor, remotely measured can be strain tensor field, strain rate tensor field, acceleration vector field. By solving by finite difference method or finite element method the first order partial differential equations whose coefficients are derived from the measured data, estimated can be the absolute elastic constant distributions, the relative elastic constant distributions with respect to the reference elastic constants, the absolute visco elastic constant distributions, the relative visco elastic constant distributions with respect to reference elastic constants, the absolute density distribution, the relative density distribution with respect to reference density.

By using the regularized algebraic equations, the errors (measurement noises) of the measured strain data, strain rate data, acceleration data can be coped with. Moreover, ill-conditioned reference regions can also be coped with.

Elasticity and visco-elasticity constants measurement apparatus, related to this conduct form is useful to monitor treatment effectiveness of radiation therapy since degeneration and change of temperature has high correlation with the change of elastic constants such as shear modulus, Poisson's ratio, Lame constants, etc., visco elastic constants such as visco shear modulus, visco Poisson's ratio, visco Lame constants, etc., delay times or relaxation times relating these elastic constants and visco elastic constants, and density.

On conduct form of FIG. 1, as an example, the ultrasound transducer is utilized as the displacement (strain) sensor 5 to measure strain tensor, strain rate tensor, acceleration vector. On the present invention, however, strain tensor, strain rate tensor, acceleration vector can be measured by signal processing of the magnetic nuclear resonance signals, and from these deformation data measured can be elastic constants such as shear modulus, Poisson's ratio, Lame constants, etc., visco elastic constants such as visco shear modulus, visco Poisson's ratio, visco Lame constants, etc., delay times or relaxation times relating these elastic constants and visco elastic constants, and density.

The next explanation is the treatment apparatus related to one of conduct forms of the present invention. This treatment apparatus uses for ultrasound therapy the above-explained measurement technique of displacement vector field/strain tensor field, and measurement technique of elastic constants, visco elastic constants, and density.

The aim of the measurement of the followings is to quantitatively examine statically or dynamically the objects, substances, materials, living things, etc., i.e., displacement vector distribution, the strain tensor distribution, the strain rate tensor distribution, the acceleration vector distribution, the velocity vector distribution, elastic constant distributions, visco elastic constant distributions. For instance, on human soft tissues, the tissues can be differentiated by extracorporeally applying pressures or low frequency vibrations, namely, by focusing on the change of the elasticity due to growth of lesion or change of pathological state. Instead of the pressures and the vibrations spontaneous hear motion or pulse can also be utilized to measure tissue deformation, and tissues can be differentiated from the values and distributions of tissue elastic constants and visco elastic constants. Blood velocity can also be observed.

Figure 27:
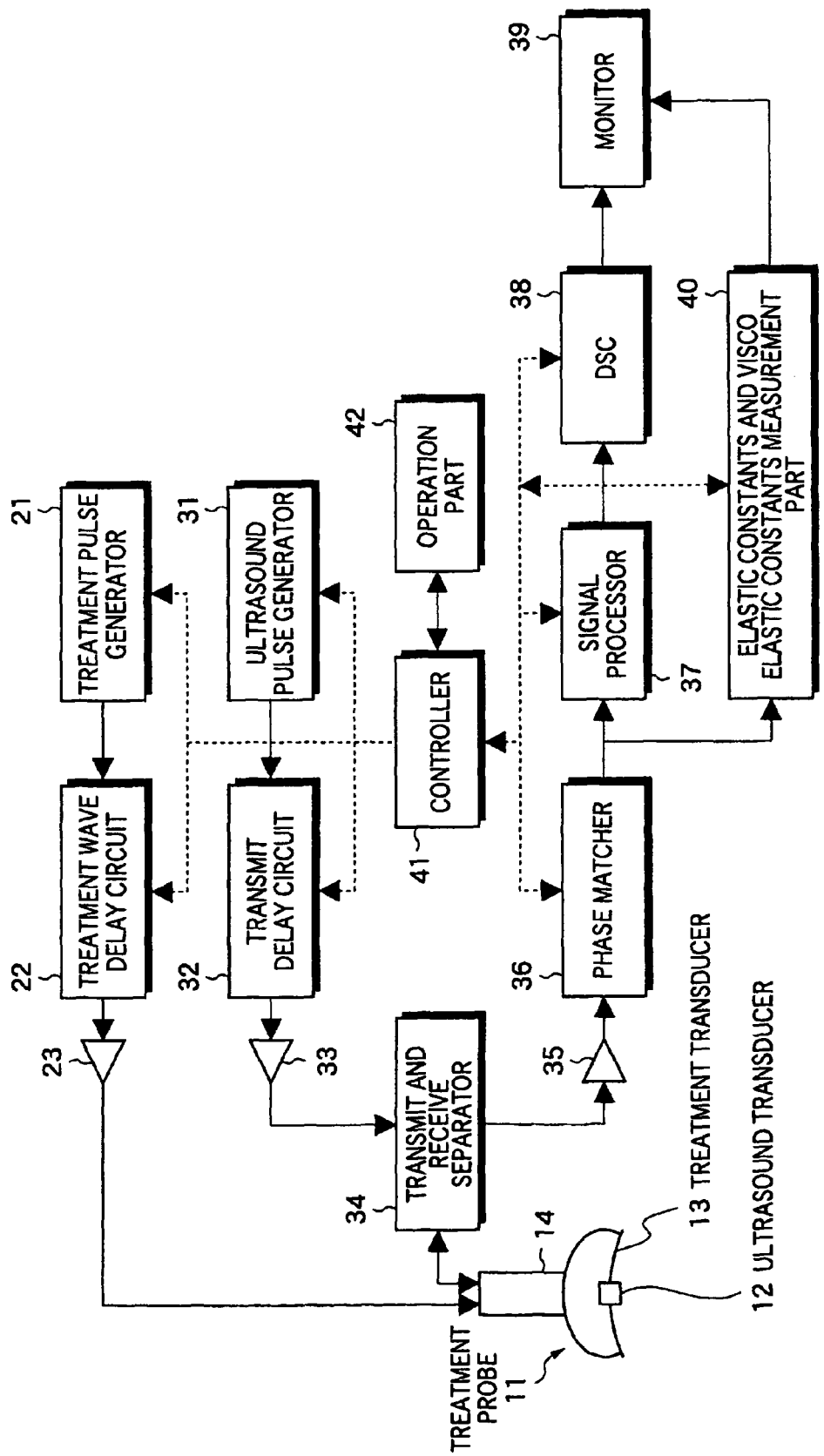
FIG. 27 shows a schematic representation of a global frame of elasticity and visco-elasticity constants measurement apparatus-based treatment apparatus related to one of conduct forms of the present invention.

FIG. 27 shows the global structure of the treatment apparatus related to this conduct form. On therapy field, lesions can be treated by applying high intensity ultrasound, laser, electromagnetic RF wave, electromagnetic micro wave, or by cryotherapy. On these low invasive treatments, degeneration occurs, composition rate in weight changes, and temperature changes. For instance, on living tissues, protein degenerates, and tissue coagulates. The degeneration, change of composition rate, and change of temperature occur together with changes of elastic constants such as shear modulus, Poisson's ratio, etc., visco elastic constants such as visco shear modulus, visco Poisson's ratio, etc., delay times or relaxation times relating these elastic constants and visco elastic constants, or density.

Thus, by measuring lesion's absolute or relative shear modulus, absolute or relative Poisson's ratio, absolute or relative visco shear modulus, absolute or relative visco Poisson's ratio, absolute or relative delay times or absolute or relative relaxation times, or absolute or relative density, etc., and by observing these time courses or these frequency variances, effectiveness of the treatments can be low invasively monitored. Based on conversion data for each tissue obtained from theories, simulations and measurements, changes of measured shear modulus, Poisson's ratio, visco shear modulus, visco Poisson's ratio, delay time, relaxation time, density, strain, strain rate, can be converted into consumed electric energy, time course of electric energy, temperature, or time course of temperature. From the measured consumed electric energy, the time course of electric energy, the temperature, or the time course of temperature, effectiveness of the treatment can be confirmed.

The consumed electric energy, the time course of electric energy can also be measured by using electric power meter and tissue physical parameters (tissue electric impedance, mechanical impedance, etc.). The temperature, or the time course of temperature can also be measured by using usual temperature monitoring method, thermo coupler, etc. By measuring these spatial distributions, not only effectiveness of treatment can be monitored, but also safety and reliability can be obtained. These monitoring data can be utilized for dynamic electronic digital control or mechanical control of beam focus position, treatment interval, ultrasound beam power, ultrasound beam strength, transmit term, transmit interval, beam shape (apodization), etc. Thus, these monitoring data can be utilized to improve the efficiency of the treatment.

FIG. 27 shows the treatment apparatus which transmits high intensity ultrasounds to lesion. The treatment apparatus can be equipped with ultrasound diagnosis equipment and elasticity and visco-elasticity constants measurement apparatus. As shown in FIG. 27, the treatment probe 11 possesses the ultrasound transducer 12 and treatment transducer 13 (treatment transducer can also serve as the ultrasound transducer 12), supporter 14. As utilized on the ultrasonic diagnosis equipment (for instance, convex type transducer), the ultrasound transducer 12 arrays plural oscillators. The treatment transducer 13 also arrays plural oscillators. In the figure, concavity type treatment probe 11 is shown. The supporter 14 can be held by hand or position controller 4, by which the position of the treatment probe 11 can be controlled.

To the treatment transducer 13, the ultrasound pulse generated at the treatment pulse generator 21 is provided through the treatment wave delay circuit 22 and amplifier 23. That is, at the treatment wave delay circuit 22 the delay time of the transmit ultrasound pulse is controlled for each oscillator, by which the focus position of the synthesized ultrasound beam is controllable.

To the oscillators of the ultrasound transducer 12, the ultrasound pulses generated at the ultrasound pulse generator 31 are provided through the transmit and receive separator 34 after being focused at the transmit delay circuit and being amplified at the amplifier 33. The echo signals received at the oscillators of the ultrasound transducer 12 are amplified at the amplifier 35 after passing through the transmit and receive separator, and the phases of the echo signals are matched at the phase matcher 36. The outputs of the phase matcher 36 are used to reconstruct image at the signal processor 37, and the image data is converted to diagnosis image at the DSC (digital scan converter) 38, and the diagnosis image is displayed at the monitor 39. Known ultrasound diagnosis equipment can be used for this diagnosis equipment.

The elastic constants and visco elastic constants measurement part 40 related to this conduct form can measure shear modulus, Poisson's ratio, visco shear modulus, visco Poisson's ratio, density, delay times or relaxation times relating these elastic constants and visco elastic constants, density, etc., using the echo signals output from phase matcher 36. The measured data and calculated results are stored at the data storage equipped with 40.

Commands of the controller 41 control the treatment pulse generator 21, the treatment wave delay circuit 22, the ultrasound pulse generator 31, the transmit delay circuit 32, the phase matcher 36, the signal processor 37, the DSC 38, and the elastic constants and visco elastic constants measurement part 40. The operator can input commands and conditions from the operation part 42 into the controller 41, by which the operator can set various operation conditions and treatment conditions. The signal processor 37, elastic constants and visco elastic constants measurement part 40, operation part 42, controller 41 are comprised of computers.

Next explanation is how this like ultrasound treatment equipment is utilized. The treatment probe 11 is contacted onto body surface, and is supported such that the ROI include the target lesion. Occasionally, by using water tank, the treatment probe 11 is supported without contacting onto the body surface. At first, to image the lesion part, the command to start imaging is input from the operation part 42, by which as the response the controller 41 outputs the commands to the ultrasound pulse generator 31 and the transmit delay circuit 32. Then, the ultrasound beam is transmitted from the ultrasound transducer 12. This ultrasound beam scans the ROI. The echo signals are received at the oscillators of the ultrasound transducer, the phases of the echo signals are matched at the phase matcher 36. The outputs of the phase matcher 36 are used to reconstruct image at the signal processor 37, and the image data is converted to diagnosis 2D image at the DSC (digital scan converter) 38, and the diagnosis image is displayed at the monitor 39. Thus, during observing the images and diagnosing tissues, when the lesion part can be detected, treatment is carried out.

That is, when the lesion is detected, the treatment probe is held at the present position. From the image memorized at the DSC 38, the controller 41 obtains the delay time to provide the drive pulse to each oscillator of the treatment transducer. Then, the controller outputs the obtained time delays into the treatment wave delay circuit 22, by which the lesion part is focused. The strength of the ultrasound beam can be controlled. The lesion part is heated. The lesion part degenerates. The treatment can also be carried out by observing 3D ultrasound image. Controlled of treatment ultrasound beam can be beam focus position, treatment interval, ultrasound beam power, ultrasound beam strength, transmit term, transmit interval, beam shape (apodization), etc.

Figure 28:
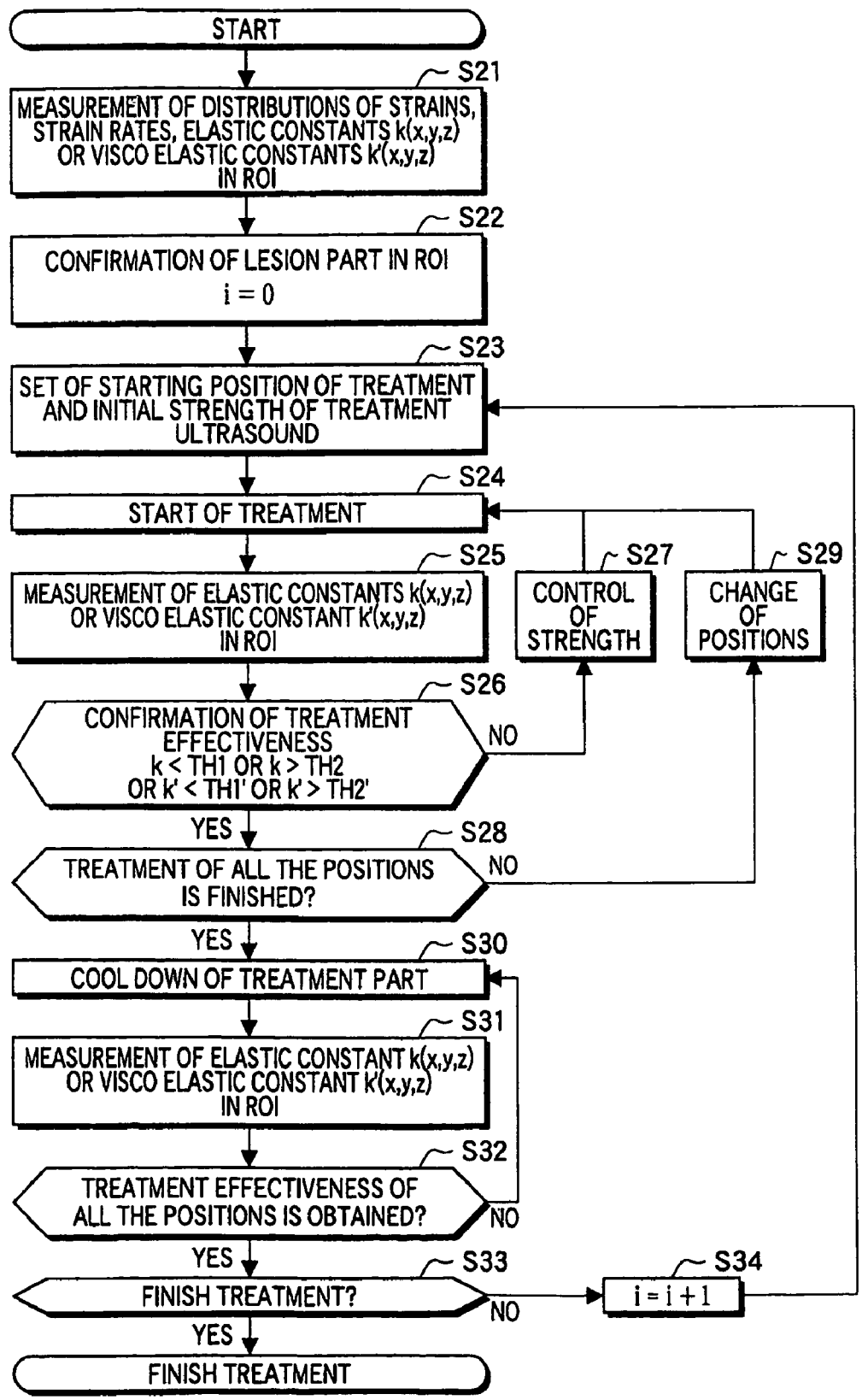
FIG. 28 shows flowchart of control procedure of the elasticity and visco-elasticity constants measurement apparatus-based treatment apparatus (FIG. 27).

Next explanation is the procedure of treatment and measurement of shear modulus, Poisson's ratio, visco shear modulus, visco Poisson's ratio, time delay, relaxation time density, etc. for monitoring the treatment effectiveness. Flowchart of FIG. 28 is referred to. At first, before the treatment, measured in the ROI are shear modulus distribution $\mu(x,y,z)$, Poisson's ratio $\nu(x,y,z)$, visco shear modulus $\mu'(x,y,z)$, visco Poisson's ratio $\nu'(x,y,z)$, delay time $\tau(x,y,z)$, relaxation time $\tau'(x,y,z)$, density $\rho(x,y,z)$ (S21). Command is sent from the operator part 42 to the controller 41, after which the ultrasounds are transmitted from the ultrasound transducer 12. Subsequently, the controller 41 sends command to the elastic constants and visco elastic constants measurement part 40, by which using echo signals output from the phase matcher 36 the strain tensor field or strain rate tensor field are measured. From the measured strain tensor field or strain rate tensor field, calculated are shear modulus distribution $\mu(x,y,z)$, Poisson's ratio $\nu(x,y,z)$, visco shear modulus $\mu'(x,y,z)$, visco Poisson's ratio $\nu'(x,y,z)$, delay time $\tau(x,y,z)$, relaxation time $\tau'(x,y,z)$, density $\rho(x,y,z)$, etc.

Next, if the lesion part is confirmed, the treatment process counter I is initialized (I=0) (S22). The starting position of the treatment and the initial strength of the treatment ultrasound are set (S23), and the treatment is started (S24). At every treatment, measured are shear modulus distribution $\mu(x,y,z)$, Poisson's ratio distribution $\nu(x,y,z)$, visco shear modulus distribution $\mu'(x,y,z)$, visco Poisson's ratio distribution $\nu'(x,y,z)$, delay time distribution $\tau(x,y,z)$, relaxation time distribution $\tau'(x,y,z)$, density distribution $\rho(x,y,z)$, etc. (S25). The measured elastic constants, visco elastic constants, delay times, relaxation times can be absolute values or spatially relative values or temporally relative values. Then, to confirm the effectiveness of the treatment, comparison can be carried out between shear modulus value $\mu(x,y,z)$, Poisson's ratio value $\nu(x,y,z)$, visco shear modulus value $\mu'(x,y,z)$, visco Poisson's ratio value $\nu'(x,y,z)$, etc., and their respective thresholds TH1 (softened case) and TH2 (hardened case), etc. (S26). Moreover, comparison can be carried out between delay time value $\tau(x,y,z)$, relaxation time value $\tau'(x,y,z)$, density value $\rho(x,y,z)$ and their respective thresholds. The thresholds TH1, TH2, etc., can be set from the information of the tissue properties etc. The thresholds TH1, TH2, etc. are the functions of the time t, the position (x,y,z), ultrasound parameters such as shooting counter etc., degeneration information, etc. The thresholds can be set before the treatment, or can be updated during the treatment. If desired effectiveness cannot be confirmed, the ultrasound strength is controlled to be higher (S27), after which the treatment is carried out again (S24). If the desired effectiveness can be confirmed, it is judged if the treatments of all the positions are finished (S28). If the treatments of all the positions are not finished yet, the treatment position is changed (S29), and the treatment is carried out again (S24).

If the treatments of all the positions are finished, the treated part is naturally or compulsively cooled down (S30). After the treatment, measured are shear modulus distribution $\mu(x,y,z)$, Poisson's ratio distribution $\nu(x,y,z)$, visco shear modulus distribution $\mu'(x,y,z)$, visco Poisson's ratio distribution $\nu'(x,y,z)$, delay time distribution $\tau(x,y,z)$, relaxation time distribution $\tau'(x,y,z)$, density distribution $\rho(x,y,z)$, etc. (S31). It is judged if desired effectiveness can be obtained at all the positions (S32). If the desired effectiveness can not be confirmed at all the positions, till the effectiveness can be confirmed, the treated part is cooled down (from S30 to S32). If the desired effectiveness is confirmed at all the positions, it is judged if this treatment process is finished (S33). When the treatment process is not finished, the treatment process counter I is incremented, and steps from S23 to S33 are iteratively carried out. The maximum number of the treatment process can be set. The treatment position can be set in order from deep position or peripheral position, or the treatment position can be set where the treatment effectiveness is not confirmed.

As described above, using the treatment apparatus of FIG. 27, during the ultrasound treatment, we can observe the treatment effectiveness in real time and then we can properly carry out the treatment. Moreover, by confirming the treatment effectiveness in real time, the ultrasound strength, the shoot number, etc. can be controlled.

The treatment apparatus of FIG. 27 can also be used for the other treatments such as laser treatment, electromagnetic RF wave treatment, electromagnetic micro wave treatment, or cryotherapy. In this case, the low invasive treatment modalities are substituted for the treatment probe 11, the treatment pulse generator 21, the treatment wave delay circuit 22, the amplifier 23.

As the ultrasound transducer 12, for instance, utilized can be 2D array aperture type applicator, 1D array aperture type applicator, concavity type applicator. For instance, when carrying out cryotherapy or radio therapeutics (applying high intensity focus ultrasound, laser, electromagnetic RF wave, microwave, etc.) on living things or the in vitro tissues through skin, mouth, vagina, anus, opened body, body surface, monitored can be degeneration, change of composition rate in weight, and change of temperature. Measured shear modulus, Poisson's ratio, visco shear modulus, visco Poisson's ratio delay time, relaxation time, density, etc., can be utilized as index to dynamically control beam position (focus), treatment interval, beam power, beam strength, transmit term, transmit interval, beam shape (apodization), etc.

Before, during, after the treatment, the followings can be displayed on monitor 39 as static or motion or time course (difference) image, the values of arbitrary points, the time course (graph), etc., i.e., not only elastic constant distribution or visco elastic constant but also displacement vector distribution, displacement vector component distributions, strain tensor component distributions, strain gradient component distributions, strain rate tensor component distributions, strain rate gradient component, acceleration vector component distributions, or velocity vector component distributions, etc.

Moreover, by utilizing ultrasound diagnosis apparatus together, spatial variations of bulk modulus and density of tissues can be measured and displayed in real-time. On the ultrasound image, as measurement results, superimposed and displayed can be static or motion or time course (difference) images of the displacement vector distribution, displacement vector component distributions, strain tensor component distributions, strain gradient component distributions, strain rate tensor component distributions, strain rate gradient component, acceleration vector component distributions, velocity vector component distributions, etc.

Particularly when the applicator has an arrayed aperture, beam focus position, treatment interval, beam power, beam strength, transmit term, transmit interval, beam shape (apodization), etc. are electronically digital controlled, while when the applicator has a concavity aperture, the focus position is mechanically controlled. The flowchart of FIG. 28 can be applied to the control program, for instance. That is, to control beam focus position, treatment interval, beam power, beam strength, transmit term, transmit interval, beam shape (apodization), etc., utilized can be absolute or relative shear modulus distribution, absolute or relative Poisson's ratio distribution, absolute or relative visco shear modulus distribution, absolute or relative visco Poisson's ratio distribution, absolute or relative delay time distributions, absolute or relative relaxation time distributions, absolute or relative density distribution, temporally absolute or relative changes of these elastic constants, visco elastic constants, delay times, relaxation times, density, etc. measured before, during, after transmitting the energies.

The above-explained measurement technique of displacement vector field, strain tensor field, etc., and measurement technique of elastic constants, visco elastic constants, density, etc., can be utilized together with interstitial needle, catheter, etc. when carrying out cryotherapy or radio therapeutics (applying high intensity focus ultrasound, laser, electromagnetic RF wave, microwave, etc.) or when non-destructive examining living things or substances or materials (cases included during producing or growing.).

For instance, on interstitial cryotherapy, interstitial radio therapeutics (applying high intensity focus ultrasound, laser, electromagnetic RF wave, micro wave, etc. utilizing needles and plate, only needles, mono needle, etc), etc., the followings can also be displayed on monitor before, during, after the treatment as static or motion or time course (difference image) image, the values of arbitrary points, the time course (graph), etc., i.e., not only elastic constant distribution or visco elastic constant but also displacement vector distribution, displacement vector component distributions, strain tensor component distributions, strain gradient component distributions, strain rate tensor component distributions, strain rate gradient component, acceleration vector component distributions, or velocity vector component distributions, etc. Moreover, by utilizing ultrasound diagnosis apparatus together, spatial variations of bulk modulus and density of tissues can also be measured and displayed in real-time. On the ultrasound image, as measurement results, superimposed and displayed can also be static or motion or time course (difference) images of the displacement vector distribution, displacement vector component distributions, strain tensor component distributions, strain gradient component distributions, strain rate tensor component distributions, strain rate gradient component, acceleration vector component distributions, velocity vector component distributions, etc. The followings can be displayed in vector style as well, i.e., the displacement vector distribution, acceleration vector, velocity vector.

To obtain safety when carrying out treatment, by setting the upper values and lower values of shear modulus, Poisson's ratio, visco shear modulus, visco Poisson's ratio, delay times, relaxation times, density, etc., and by setting the upper values of absolute or relative changes of these, beam position (focus), treatment interval, beam power, beam strength, transmit term, transmit interval, beam shape (apodization), etc. should be controlled such that these physical parameter values do not change more than necessary.

The treatment effectiveness can also be evaluated by measuring temperature and temporal change of temperature as above-explained from strain (tensor) distribution, strain rate (tensor) distribution, shear modulus distribution, Poisson's ratio distribution, visco shear modulus distribution, visco Poisson's ratio distribution, density distribution, temporal changes of these, etc. measured before, during, after transmitting the energies. In this case, to obtain safety, by setting the upper values of temperature or change of temperature, beam position (focus), treatment interval, beam power, beam strength, transmit term, transmit interval, beam shape (apodization), etc. should be controlled such that the temperature do not heighten more than necessary. These can also be controlled utilizing shear modulus value $\mu$, Poisson's ratio value $\nu$, visco shear modulus value, visco Poisson's ratio value, density value, delay time values, relaxation time values, strain values, strain rate values, etc. converted from the upper values. Temperature and change of temperature can also be measured utilizing the conventional temperature measurement method or thermo coupler.

In cases where no mechanical source exists, or mechanical sources are not utilized, degeneration, change of composition rate in weight, and change of temperature can also be detected from strain (tensor) distribution, strain rate (tensor) distribution, shear modulus distribution, Poisson's ratio distribution, visco shear modulus distribution, visco Poisson's ratio distribution, density distribution, temporal changes of these, etc. measured before, during, after transmitting the energies. Directly the expansion and shrink can also be detected when strain (tensor) distribution or strain rate (tensor) distribution are measured.

The elasticity and visco-elasticity constants measurement apparatus of the present invention can be utilized to monitor degeneration, change of composition rate in weight, change of temperature due to injection of medicine, putting of medicine, giving of medicine. To control amount the medicine, term, interval, position, etc., utilized can be absolute or relative shear modulus distribution, absolute or relative Poisson's ratio distribution, absolute or relative visco shear modulus distribution, absolute or relative visco Poisson's ratio distribution, absolute or relative delay time distributions, absolute or relative relaxation time distributions, absolute or relative density distribution, temporally absolute or relative changes of these elastic constants, visco elastic constants, delay times, relaxation times, density, etc. measured before, during, after the treatment. Anticancer drug can be utilized as the medicine.

That is, to monitor the treatment effectiveness (including change of temperature) of anticancer drug and to control the treatment, the followings can also be displayed on monitor before, during, after the treatment as static or motion or time course (difference) image, the values of arbitrary points, the time course (graph), etc., i.e., not only elastic constant distribution or visco elastic constant but also displacement vector distribution, displacement vector component distributions, strain tensor component distributions, strain gradient component distributions, strain rate tensor component distributions, strain rate gradient component, acceleration vector component distributions, or velocity vector component distributions, etc. Moreover, by utilizing ultrasound diagnosis apparatus together, spatial variations of bulk modulus and density of tissues can also be measured and displayed in real-time. On the ultrasound image, as measurement results, superimposed and displayed can also be static or motion or time course (difference) images of the displacement vector distribution, displacement vector component distributions, strain tensor component distributions, strain gradient component distributions, strain rate tensor component distributions, strain rate gradient component, acceleration vector component distributions, velocity vector component distributions, etc. The followings can be displayed in vector style as well, i.e., the displacement vector distribution, acceleration vector, velocity vector. In cases where no mechanical source exists, or mechanical sources are not utilized, degeneration, expansion or shrink, and change of temperature, etc. can also be detected from displacement vector, strain (tensor) distribution, strain rate (tensor) distribution, etc.

The elastic constants, visco elastic constants, density, high order data expressed from elastic constants, visco elastic constants, density are utilized to obtain non-linear properties of tissues by linear approximation of non-linear phenomena in infinitesimal time space or spatial space. Thus, estimated non-linear elastic constants data, non-linear visco elastic constants data, high order data expressed from non-linear data can be utilized for diagnosis and treatment.

Thus, as explained above, the present invention can realize accurate measurement in 3D space of interest (SOI) or 2D region of interest (ROI) or 1D ROI of displacement vector distribution, strain tensor distribution, the spatio or temporal derivatives of these, generated due to arbitrary mechanical sources. If the target naturally deforms, elastic constant or visco elastic constant can be estimated in the SOI or ROI without disturbing the deformation field from measured deformation data. Moreover, even if there exist another mechanical sources and uncontrollable mechanical sources in the object, for instance, the elastic constant and visco elastic constant measurement apparatus can be utilized, which is applicable for diagnosing the part of interest in the object and for monitoring the treatment effectiveness. Furthermore, low-invasive treatment apparatus can be realized, which is equipped with such elastic constant and visco elastic constant measurement apparatus.

The invention claimed is:

1. A displacement measurement apparatus comprising:
  a sensor for transmitting ultrasounds to a target in accordance with drive signals, and detecting ultrasound echo signals generated in the target to output echo signals;
  driving and processing means for supplying the drive signals to the sensor, and processing the echo signals outputted from the sensor;
  control means for controlling the driving and processing means; and
  data processing means for yielding a local 3D, 2D, or 1D displacement vector and/or local displacement vector components by solving simultaneous equations, coefficients of said simultaneous equations being expressed at each position by temporal change of a phase of the echo signal at the position and frequencies of the respective directions at the position derived by applying specified processing to complex analytic signals obtained from the echo signals acquired by transmitting ultrasounds more than one time to a region of interest within the target.

2. The displacement measurement apparatus according to claim 1, further comprising:
  means for steering an ultrasound beam such that axial displacements measured by using the respective steered beams are used for synthesizing an accurate displacement vector measurement.

3. The displacement measurement apparatus according to claim 1, wherein said data processing means utilizes at least one of ultrasound echo basic wave components and ultrasound echo harmonic wave components included in the ultrasound echo signals.

4. The displacement measurement apparatus according to claim 1, further comprising:
  means for shifting the echo signals by using estimated displacement data in order to allow combinational use of other displacement measurement methods or improve measurement accuracy.

5. The displacement measurement apparatus according to claim 1, further comprising:
  means for utilizing priori information about one of (i) magnitude, (ii) spatial and temporal continuity, and (iii) differentiability of displacement and/or displacement distribution.

6. The displacement measurement apparatus according to claim 1, further comprising:
  means for yielding at least one of strain tensor components, strain rate tensor components, velocity vector components, and acceleration vector components by applying a spatial or temporal differential filter with a cut off frequency in one of spatial domain and frequency domain to the yielded local 3D, 2D or 1D displacement vector.

7. The displacement measurement apparatus according to claim 1, further comprising:
  means for yielding image data of at least one of displacement vector, strain tensor, strain rate tensor, gradients thereof, Laplacians thereof, first temporal derivatives thereof, second temporal derivatives thereof, frequency variances thereof, temporal relative changes thereof, and temporal absolute changes thereof; and
  display means for displaying an image based on the image data.

8. The displacement measurement apparatus according to claim 1, further comprising:
  means for yielding image data of at least one of displacement vector, strain tensor, strain rate tensor, gradients thereof, Laplacians thereof, first temporal derivatives thereof, second temporal derivatives thereof, frequency variances thereof, temporal relative changes thereof, and temporal absolute changes thereof, which is superimposed on one of a conventional ultrasound image and magnetic resonance images; and
  display means for displaying an image based on the image data.

9. A displacement measurement apparatus comprising:
  a sensor for transmitting ultrasounds to a target in accordance with drive signals, and detecting ultrasound echo signals generated in the target to output echo signals;

driving and processing means for supplying the drive signals to the sensor, and processing the echo signals outputted from the sensor;

control means for controlling the driving and processing means; and data processing means for directly measuring a local strain tensor and/or local strain tensor components specified on the basis of phases of the echo signals acquired by transmitting ultrasounds more than one time to a region of interest within the target.

10. A displacement measurement apparatus comprising:

a sensor for transmitting ultrasounds to a target in accordance with drive signals, and detecting ultrasound echo signals generated in the target to output echo signals;

driving and processing means for supplying the drive signals to the sensor, and processing the echo signals outputted from the sensor;

control means for controlling the driving and processing means; and data processing means for yielding a local 3D, 2D, or 1D displacement vector and/or local displacement vector components by estimating gradient of a phase of a local cross-spectrum obtained from the echo signals acquired by transmitting ultrasounds more than one time to a region of interest within the target, said echo signals being thinned out to increase echo data intervals in respective directions such that aliasing of the phase does not occur for a large displacement vector.

* * * * *

UNITED STATES PATENT AND TRADEMARK OFFICE
CERTIFICATE OF CORRECTION

PATENT NO. : 7,775,980 B2
APPLICATION NO. : 11/312591
DATED : August 17, 2010
INVENTOR(S) : Chikayoshi Sumi It is certified that error appears in the above-identified patent and that said Letters Patent is hereby corrected as shown below:

On the Title page, insert after Prior Publication Data, the following Related U.S. Application Data:

Item --(63) This is a Continuation of Application No. 10/326,526 filed December 23, 2002.--

Signed and Sealed this
Thirtieth Day of April, 2013

Teresa Stanek Rea
*Acting Director of the United States Patent and Trademark Office*